United States Patent [19]

Shimizu et al.

[11] Patent Number: 5,356,561

[45] Date of Patent: * Oct. 18, 1994

[54] CARBOXYLATE COMPOUNDS, LIQUID CRYSTAL COMPOSITIONS AND LIQUID CRYSTAL ELEMENTS CONTAINING SAID COMPOUNDS AND METHOD OF OPTICAL MODULATION USING SAID ELEMENTS

[75] Inventors: Toyoji Shimizu, Tokyo; Shinichi Nishiyama, Kimitsu; Nobuyuki Doi, Kimitsu; Shoichi Miyakoshi, Kimitsu; Tooru Yamanaka, Kimitsu; Katsuo Taniguchi, Ichihara; Hideo Hama, Kimitsu, all of Japan

[73] Assignee: Mitsui Petrochemical Industries, Ltd., Tokyo, Japan

[*] Notice: The portion of the term of this patent subsequent to Sep. 21, 2010 has been disclaimed.

[21] Appl. No.: 813,032

[22] Filed: Dec. 24, 1991

Related U.S. Application Data

[63] Continuation-in-part of Ser. No. 623,557, Dec. 7, 1990, abandoned.

[30] Foreign Application Priority Data

| Dec. 7, 1989 [JP] | Japan | 1-318456 |
| Feb. 23, 1990 [JP] | Japan | 2-43533 |
| Feb. 23, 1990 [JP] | Japan | 2-43534 |
| Jun. 25, 1990 [JP] | Japan | 2-166393 |

[51] Int. Cl.$^5$ .................... C09K 19/32; C07C 69/76
[52] U.S. Cl. ............ 252/299.62; 252/299.01; 560/56; 560/80; 560/100; 560/119
[58] Field of Search .......... 252/299.01, 299.62, 252/299.64, 299.65, 299.66, 299.67; 560/8, 56, 59, 80, 100, 102, 116, 119

[56] References Cited

U.S. PATENT DOCUMENTS

| 4,341,652 | 7/1982 | Takei et al. | 252/299.5 |
| 4,386,007 | 5/1983 | Krause et al. | 252/299.62 |
| 4,613,209 | 9/1986 | Goodby et al. | 252/299.62 |
| 4,680,137 | 7/1987 | Isoyama et al. | 252/299.62 |
| 4,759,869 | 7/1988 | Ohno et al. | 252/299.67 |
| 4,886,620 | 12/1989 | Hopf et al. | 252/299.01 |
| 5,246,622 | 9/1993 | Shimizu et al. | 252/299.62 |

FOREIGN PATENT DOCUMENTS

| 0205340 | 12/1986 | European Pat. Off. |
| 0341922 | 11/1989 | European Pat. Off. |
| 56-46855 | 4/1981 | Japan |
| 56-108740 | 8/1981 | Japan |

*Primary Examiner*—Shean Wu
*Attorney, Agent, or Firm*—Sherman and Shalloway

[57] ABSTRACT

In accordance with the present invention, there are provided carboxylate compounds represented by the following formula [A] and liquid crystal material comprising said compounds

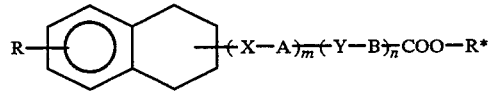

[A]

wherein R is a group selected from the group consisting of alkyl, alkoxy and halogenated alkyl group of 3-20 carbon atoms, X and Y represent each a group selected from the group consisting of —COO—, —OCO—, —CH$_2$CH$_2$—, —CH$_2$O—, —OCH$_2$—, —S—S—,

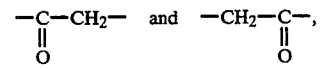

or a single bond, A and B represent each a group selected from the group consisting of specific divalent aromatic and alicyclic group such as phenylene, cyclohexylene and tetrahydronaphthalene and R* is an optically active group of 4-20 carbon atoms containing at least one asymmetric carbon atom (hydrogen atoms attached to the carbon atoms of said optically active group may be substituted with halogen atoms), and m and n are each an integer of 0-2, with the proviso that both m and n do not become 0 at the same time.

27 Claims, 27 Drawing Sheets

1 PITCH

SPONTANEOUS POLARIZATION

VOLTAGE APPLIED
(10Hz TRIANGULAR WAVE)

VOLTAGE APPLIED
(100Hz TRIANGULAR WAVE)

CARBOXYLATE COMPOUNDS, LIQUID CRYSTAL COMPOSITIONS AND LIQUID CRYSTAL ELEMENTS CONTAINING SAID COMPOUNDS AND METHOD OF OPTICAL MODULATION USING SAID ELEMENTS

This application is a continuation-in-part of copending application Ser. No. 07/623,557, filed Dec. 7, 1990.

FIELD OF THE INVENTION

This invention relates to novel carboxylate (carboxylic acid ester) compounds and liquid crystal compositions containing said compounds.

In another aspect, the invention relates to liquid crystal elements containing the novel carboxylate compounds described above, processes for the preparation thereof and methods of light modulation using said elements.

BACKGROUND OF THE INVENTION

Display devices relying on use of liquid crystal compounds which are widely used therefor at present are driven by TN (twisted nematic) mode.

When this TN mode is adopted, however, there are involved such problems that in order to change the image being displayed, the driving time is prolonged, because the position of the molecule of the liquid crystal compound in the element must be changed, and also the voltage necessary for changing the position of the molecules of the liquid crystal compound, that is, the power consumption becomes large.

In distinction to switching elements utilizing TN mode or STN mode, the switching elements using ferroelectric liquid crystal compounds are able to function as switching elements only by changing the direction of molecular orientation of said liquid crystal compounds and hence the switching time required for operating the switching elements is markedly shortened. Further, because a value of Ps×E obtained from a spontaneous polarization (Ps) of the ferroelectric liquid crystal compound and intensity of the electric field (E) applied is an effective energy output for changing the direction of molecular orientation of said liquid crystal compound, power consumption required therefor can also be markedly minimized. Such ferroelectric liquid crystal compounds as mentioned above are suitable particularly as display devices for moving picture, because they have two steady states depending upon the direction of electric field applied, that is, bistability and also very favorable switching threshold value characteristics.

When these ferroelectric liquid crystal compounds are intended to use in optical switching elements, they are required to have such characteristics as an operating temperature in the vicinity of ordinary temperature or below, a wide operating temperature zone, a high switching speed and an appropriate switching threshold value voltage. Particularly, of these characteristics, the operating temperature range is especially important when the ferroelectric liquid crystal compounds are used in optical switching elements.

So far as ferroelectric liquid crystal compounds known hitherto are concerned, however, they are generally narrow in operating temperature, and even in ferroelectric liquid crystal compounds having a wide operating temperature range, said operating temperature range is in a high temperature zone excluding room temperature, as disclosed in R. B. Meyer et al., J. de Phys., Vol. 36 L, p. 69 (1975) and a paper reported by M. Taguchi and T. Harada, "Proceedings of Eleventh Conference on Liquid Crystal", p. 168 (1985). Thus, no ferroelectric liquid crystal compounds which are satisfactory from the standpoint of practical use are available yet.

Hopf discloses in U.S. Pat. No. 4,886,620 the compounds represented by the following formula I;

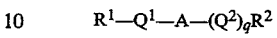

wherein $R^1$ may be an alkyl group of 1-15 carbon atoms (column 1, lines 11—13) or an alkoxy group of 3-12 carbon atoms (column 5, lines 4-8), $Q^1$ and $Q^2$ are independently represented by —($A^0$—$Z^0$)— (column 1, lines 61-62) in which $A^0$ may be hydroxynaphthalene (column 2, lines 16—17), $Z^0$ may be —COO—, —OCO—or —$CH_2CH_2$—, A may be cyclohexylene or hydroxynaphthalene (column 1, lines 25—35), $R^2$ may be —X—Q— C*(Y)H—R . in which X may be —COO—, —OCO— or a single bond, Q is alkylene containing 1 to 5 carbon atoms, Y may be a methyl group, R is an alkyl group differing from Y and containing 1 to 18 carbon atoms wherein one or two nonadjacent $CH_2$ groups may be replaced by such divalent group other than alkylene as —COO— and the like.

As disclosed in this reference, the above type of the compounds indicating smectic phases has been considered to be required of having at least one of the groups of $Z^0$, $Z^1$ and $Z^2$ being substituted by —CN group (See the reference at column 2, lines 24—44) in the prior art.

By the way, there have heretofore been made various proposals for light modulation elements using such ferroelectric liquid crystal compounds as mentioned above.

For example, these light modulation elements may be driven by a method using a liquid crystal cell composed of two transparent substrates being arranged so as to face each other, leaving a gap of about 2 μm between said substrates, said gap being filled with a ferroelectric liquid crystal assuming a chiral smetic phase C.

The ferroelectric crystal has a layer structure in the chiral smetic phase C, and in this layer a major axis of molecule is oriented so that this axis forms a practically definite angle θ (called a tilt angle). In this state, as shown in FIG. 4, the major axis of liquid crystal molecule 41 gradually turns owing to interaction between the molecules to a different direction and comes to form a helical structure (FIG. 4).

However, when a gap of about 2 μm formed by two glass substrates is filled with a liquid crystal material, the oriented state of the liquid crystal material is influenced by the glass substrates to release its helical structure, and the liquid crystal molecule 51 comes to exhibit two forms of steady state when viewed from above the transparent substrate 50 as shown in FIG. 5. In the steady state as mentioned above, because the major axis of liquid crystal molecule and a dipole perpendicular thereto take the direction opposite to each other in the two forms of steady state, the steady state of the liquid crystal material can be transferred between the above-mentioned two steady states by applying an electric field thereto.

In that case, the amount of transmitted light can be controlled by arranging the above-mentioned liquid crystal cell between two polarizing plates wherein the directions of polarized light cross at right angles so that the cell becomes dark (the amount of transmitted light decreases) when the liquid crystal in the cell takes one form of the two forms of steady state.

In the process as mentioned above, theoretically it is said that the steady state of liquid crystal material present in the cell involves only two forms as aforesaid. Therefore, it is said that when the liquid crystal material in the cell is once brought to the steady state by allocation thereto of an electric field, said liquid crystal material will not be transferred to another form of the steady state even when the electric field applied is eliminated therefrom, and accordingly the light modulation element comprising the above-mentioned liquid crystal cell comes to have a memory effect.

Actually, however, when the liquid crystal material held in a steady state is allowed to stand, as it is, without application thereto of an electric field, parts of the liquid crystal material are transferred sometimes to another form of steady state, and it is difficult to impart a sufficient memory effect to the light modulation element, that is, it is difficult to maintain the liquid crystal material in a definite steady state at its steady state for a long period of time with application thereto of an electric field. Therefore, in order to maintain the steady state of liquid crystal material, that is, a bright state and a dark state of the light modulation element, it is necessary to apply an electric field thereto to a certain degree.

In the conventional process as mentioned above, the application of an electric field is necessary for attaining even a dark state, and in most cases it was difficult to attain a dark state having a sufficient darkness. On that account, it has been unsuccessful in obtaining a sufficient brightness ratio of a bright state to a dark state, that is, a sufficient contrast.

OBJECT OF THE INVENTION

The present invention has-been made in view of the prior art as mentioned above, and an object of the invention is to provide novel carboxylate compounds usable as a liquid crystal compound or liquid crystal modifying agent together with other liquid crystal compound capable of forming display devices having such excellent characteristics as broad operating temperature range, high switching speed, appropriate switching threshold value voltage, operability with very small power consumption and high contrast.

Another object of the invention is to provide liquid crystal materials comprising the above-mentioned novel carboxylate compounds and having excellent characteristics.

A still further object of the invention is to provide novel liquid crystal elements having excellent characteristics using the above-mentioned novel carboxylate compounds, processes for the preparation thereof, and methods of light modulation using said elements.

SUMMARY OF THE INVENTION

The novel carboxylate compounds according to the present invention are represented by the following formula [A].

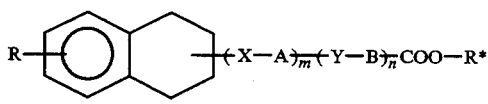

[A]

wherein R is a group selected from the group consisting of alkyl of 3–20 carbon atoms, alkoxy of 3–20 carbon atoms and halogenated alkyl of 3–20 carbon atoms, X and Y each represent a group selected from the group consisting of —COO—, —OCO—, —CH$_2$CH$_2$—, —CH$_2$O—, OCH$_2$—, —S—S—,

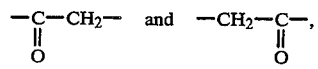

or a single bond, A and B each represents a group selected from the group consisting of

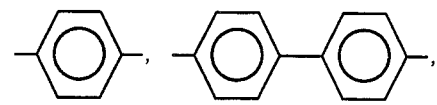

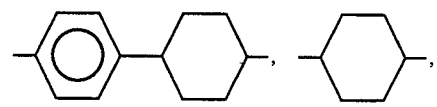

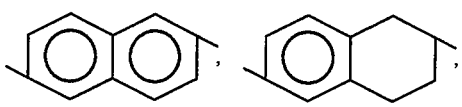

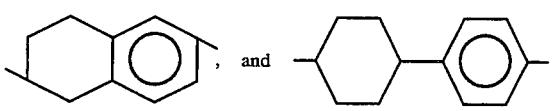

and R* is an optically active gruop of 4–20 carbon atoms containing at least one asymmetric carbon atom (hydrogen atoms attached to the carbon atoms of said optically active group may be substituted with halogen atoms), and m and n are each an integer of 0–2, with the proviso that both m and n do not become 0 at the same time.

Such novel carboxylate compounds as illustrated above may be used as liquid crystal compounds.

The liquid crystal compositions according to the invention contain the above-mentioned carboxylate compounds.

The first liquid crystal element according to the invention comprises a cell composed of two substrates being arranged so as to face each other leaving a gap between said substrates, said gap being filled with a liquid crystal material which is a liquid crystal composition containing at least one of the above-mentioned carboxylate compounds.

The second liquid crystal element according to the invention comprises a cell composed of two substrates being arranged so as to face each other leaving a gap therebetween, and said gap being filled with a liquid crystal material, wherein each substrate is provided with a transparent electrode on the inner surface thereof, a polarizing plate is provided on the outside of each substrate so that a plane of polarization formed by the polarizing plates has an angle of 70°–110° and the cell filled with the liquid crystal material is arranged between the polarizing plates at an angle of from +10° to −10° C. relative to the position of the cell at which the transmitted light becomes the darkest or the brightest, said liquid crystal material containing the liquid crystal compound represented by the above-mentioned formula [A].

The method of light modulation according to the invention comprises applying an electric field to the above-mentioned second liquid crystal element.

The process according to the invention for the preparation of a liquid crystal element comprising a cell composed of two substrates being arranged so as to face each other leaving a gap therebetween, said gap being filled with a liquid crystal material, which process comprises forming the cell by providing an orientation controlling film on the inner surface of at least one substrate, filling the gap with the liquid crystal material containing the carboxylate compound represented by the above-mentioned formula [A], and heating said liquid crystal material contained in the cell to a temperature not lower than the temperature at which said material exhibits an isotropic liquid, followed by cooling to a temperature not higher than the temperature at which said material exhibits a liquid crystal.

By virtue of using the above-mentioned carboxylate compounds as liquid crystal compounds, there can be obtained various display devices having such excellent characteristics as broad operating temperature range, high switching speed, very small power consumption and stable contrast.

DETAILED DESCRIPTION OF THE INVENTION

Figure 1:
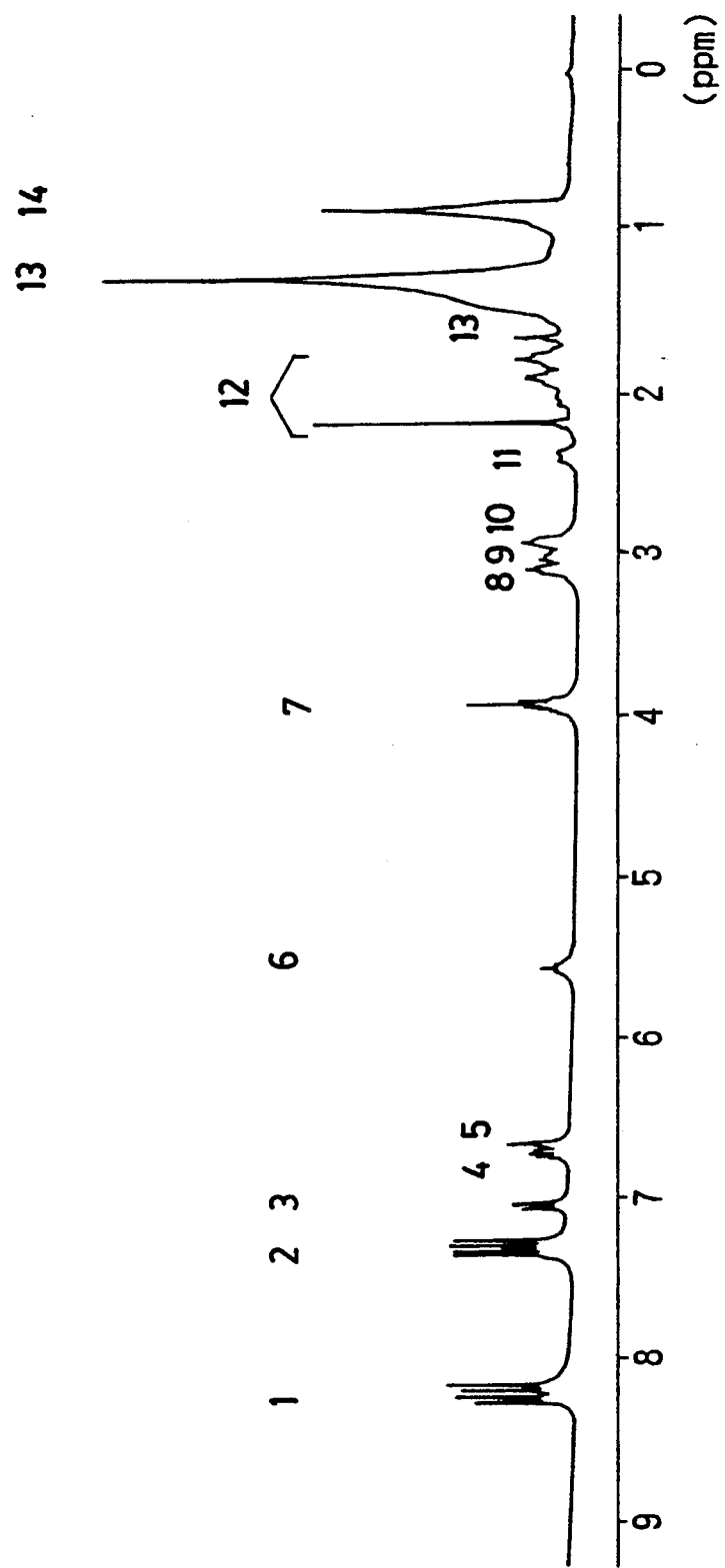
FIG. 1 is a chart showing $^1$H-NMR spectrum of R-1'''-trifluoromethylheptyl 4-[4'-(1'',2'',3'',4''-tetrahydro-6''-n-decyloxy-2''-naphthoyloxy) benzoyloxy] benzoate.

The carboxylate compounds according to the present invention, liquid crystal compositions and liquid crystal elements containing the same, and methods of light modulation using said elements are illustrated below in detail.

First, the novel carboxylate compounds of the invention are illustrated.

The novel carboxylate compounds and liquid crystal compounds according to the invention may be represented by the following formula [A].

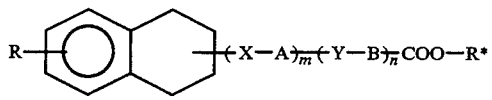
[A]

In the formula [A], R represents a group selected from the group consisting of alkyl of 3–20 carbon atoms, alkoxy of 3–20 carbon atoms, and halogenated alkyl of 3–20 carbon atoms.

In the above formula [A], when R is alkyl of 3–20 carbon atoms, the alkyl may be any of straight-chain, branched and alicyclic ones. Of the carboxylate compounds of the formula [A], those in which R is straight-chain alkyl, however, exhibit excellent liquid crystal properties, because their molecules assume a rigid structure extending in a straight line. Examples of such straight-chain alkyl includes hexyl, heptyl, octyl, nonyl, decyl, undecyl, dodecyl, tetradecyl, hexadecyl and octadecyl.

When R is halogenated alkyl in the formula [A], examples of such halogenated alkyl include the above-mentioned straight-chain alkyl in which at least a part of the hydrogen atoms has been substituted with a halogen atom such as F, Cl, Br or I.

When R is alkoxy in the above-mentioned formula [A], examples of such alkoxy include alkoxy having the above-mentioned straight-chain alkyl, for example, hexoxy, heptoxy, octyloxy, nonyloxy, tetradecyloxy, heptadecyloxy, hexadecyloxy and octadecyloxy, undecyloxy.

Of the compounds of the above formula [A], those in which R is alkoxy exhibit particularly excellent liquid crystal properties.

In the formula [A] mentioned above, X and Y each represents a group selected from among —COO—, —OCO—, —CH₂CH₂—, —CH₂O—, OCH₂—, —S—S—,

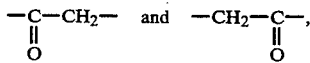

or a single bond. In the case of the carboxylate compounds of the above formula [A] of the invention used as liquid crystal compounds, X and Y are each selected desirably from among —COO—, —OCO—, —CH₂CH₂—, —CH₂O—, and OCH₂—, and particularly when linearity of the molecule is taken into account, at least one of X and Y is —COO—, preferably both X and Y are —COO—.

In the above-mentioned formula [A], A and B each represent a group selected from the group consisting of

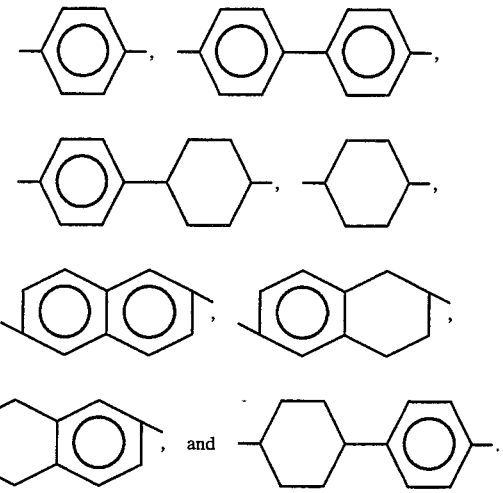

In the case of the carboxylate compound of the above formula [A] of the invention are used as liquid crystal compounds, when characteristics of liquid crystal material are taken into account, A and B are each preferably the group

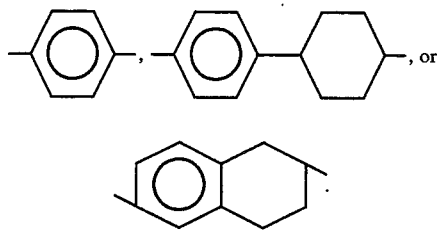

Of these groups, particularly preferred is phenylene.

In the above formula [A], R* represents an optically active group of 4–20 carbon atoms having at least one asymmetric carbon atom. The hydrogen atoms attached to the carbon atoms constituting this optically active group may be substituted with halogen atom such as F, Cl, Br or I, particularly with fluorine atom. Examples of such optically active group include those as mentioned below.

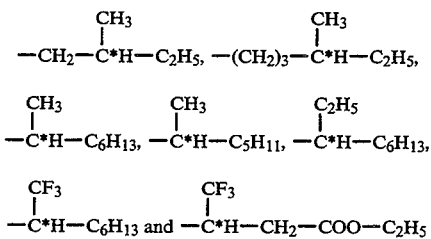

Of the optically active groups as mentioned above, preferred are those including

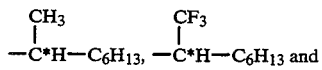

-continued $$-\overset{CF_3}{\underset{|}{C^*H}}-CH_2-COO-C_2H_5.$$

Of these groups, particularly preferred is $$-\overset{CF_3}{\underset{|}{C^*H}}-C_6H_{13}.$$

In the formula [A], m and n each represent an integer of 0-2, with the proviso that both m and n do not become 0 at the same time.

In particular, when the carboxylate compounds of the formula [A] are used as liquid crystal compounds, m is preferably 1 or 2.

In the formula [A] mentioned above, 1,2,3,4-tetrahydronaphthyl group includes 1,2,3,4-tetrahydro-1,5-naphthyl, 1,2,3,4-tetrahydro-1,6-naphthyl, 1,2,3,4-tetrahydro-2,6-naphthyl and 1,2,3,4-tetrahydro-1,7-naphthyl.

Particularly, when the carboxylate compounds of the invention are used as liquid crystal compounds, it is preferable that the whole molecule be linear, and particularly preferred as 1,2,3,4-tetrahydronaphthyl group is 1,2,3,4-tetrahydro-2,6-naphthyl.

Accordingly, the carboxylate compounds represented by the above-mentioned formula [A] may include concretely those represented by the formulas [1] to [48].

[1] $H_{33}C_{16}-O-\text{(tetrahydronaphthyl)}-COO-\text{(phenyl)}-COO-\text{(phenyl)}-COO-\text{(phenyl)}-COO-C^*H(CH_2)_5CH_3 \; | \; CF_3$

[2] $H_{29}C_{14}-O-\text{(tetrahydronaphthyl)}-COO-\text{(phenyl)}-COO-\text{(phenyl)}-COO-\text{(phenyl)}-COO-C^*H(CH_2)_5CH_3 \; | \; CF_3$

[3] $H_{25}C_{12}-O-\text{(tetrahydronaphthyl)}-COO-\text{(phenyl)}-COO-\text{(phenyl)}-COO-\text{(phenyl)}-COO-C^*H(CH_2)_5CH_3 \; | \; CF_3$

[4] $H_{23}C_{11}-O-\text{(tetrahydronaphthyl)}-COO-\text{(phenyl)}-COO-\text{(phenyl)}-COO-\text{(phenyl)}-COO-C^*H(CH_2)_5CH_3 \; | \; CF_3$

[5] $H_{21}C_{10}-O-\text{(tetrahydronaphthyl)}-COO-\text{(phenyl)}-COO-\text{(phenyl)}-COO-\text{(phenyl)}-COO-C^*H(CH_2)_5CH_3 \; | \; CF_3$

[6] $H_{19}C_{9}-O-\text{(tetrahydronaphthyl)}-COO-\text{(phenyl)}-COO-\text{(phenyl)}-COO-\text{(phenyl)}-COO-C^*H(CH_2)_5CH_3 \; | \; CF_3$

[7] $H_{17}C_{8}-O-\text{(tetrahydronaphthyl)}-COO-\text{(phenyl)}-COO-\text{(phenyl)}-COO-\text{(phenyl)}-COO-C^*H(CH_2)_5CH_3 \; | \; CF_3$

[8] $H_{15}C_{7}-O-\text{(tetrahydronaphthyl)}-COO-\text{(phenyl)}-COO-\text{(phenyl)}-COO-\text{(phenyl)}-COO-C^*H(CH_2)_5CH_3 \; | \; CF_3$

[9] $H_{33}C_{16}-O-\text{(tetrahydronaphthyl)}-COO-\text{(phenyl)}-COO-C^*H-(CH_2)_5-CH_3 \; | \; CF_3$

[10] $H_{29}C_{14}-O-\text{(tetrahydronaphthyl)}-COO-\text{(phenyl)}-COO-C^*H-(CH_2)_5-CH_3 \; | \; CF_3$

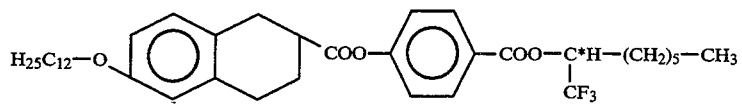
[11]
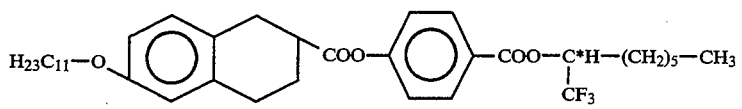
[12]
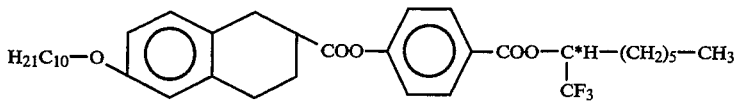
[13]
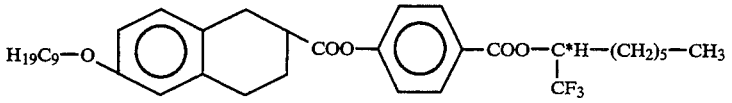
[14]
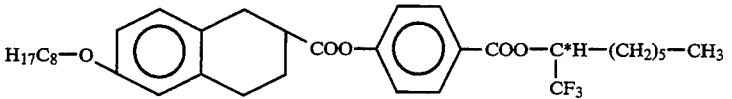
[15]
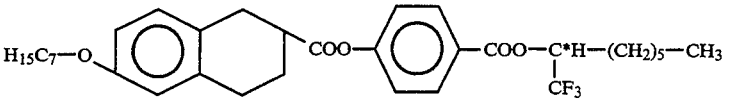
[16]
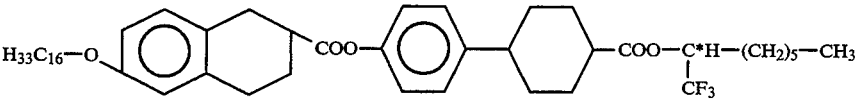
[17]
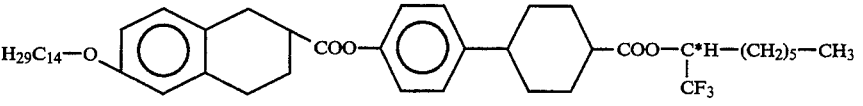
[18]
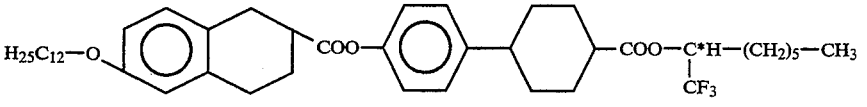
[19]
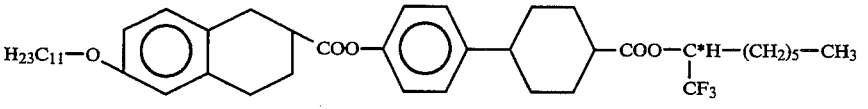
[20]
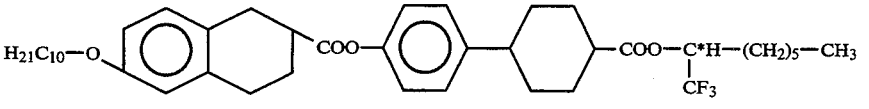
[21]
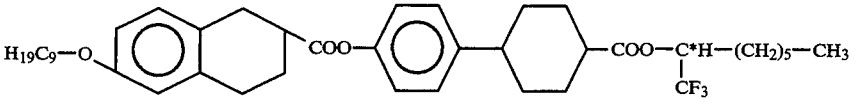
[22]
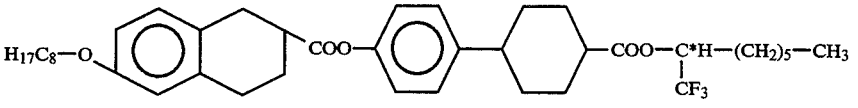
[23]

-continued
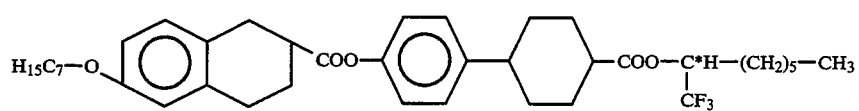
[24]
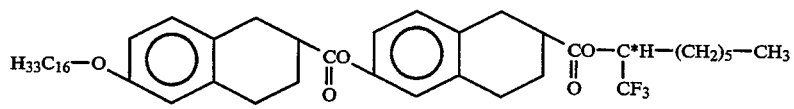
[25]
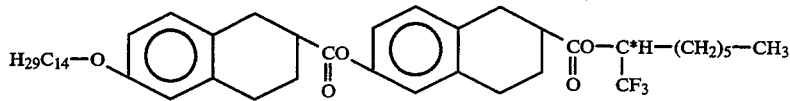
[26]
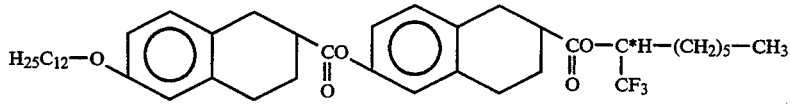
[27]
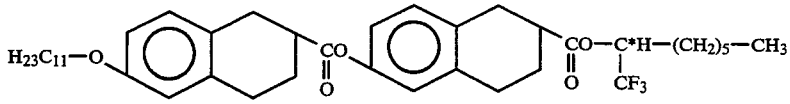
[28]
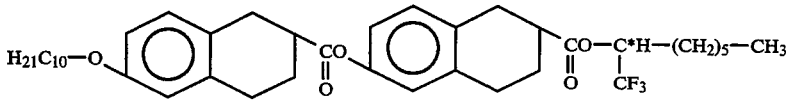
[29]
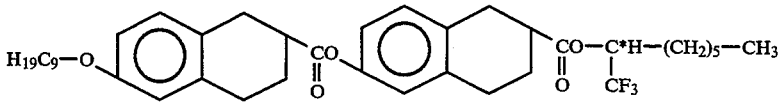
[30]
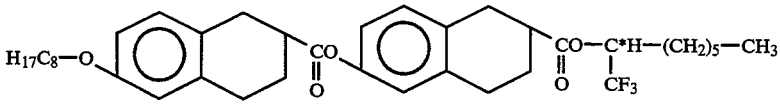
[31]
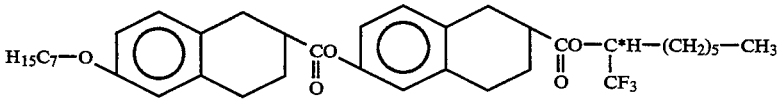
[32]
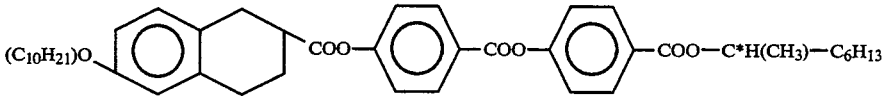
[33]
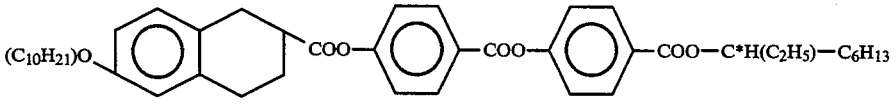
[34]
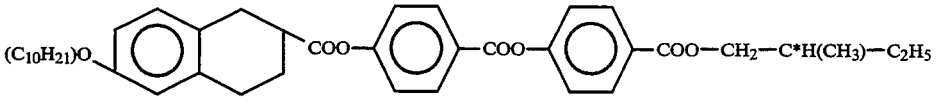
[35]
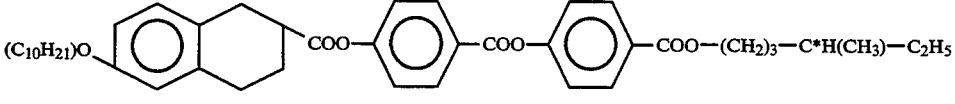
[36]

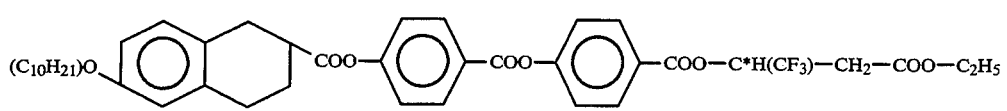
[37]
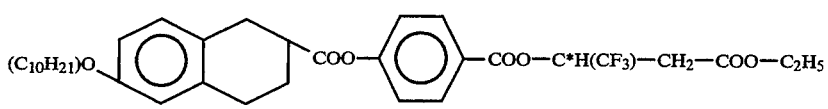
[38]
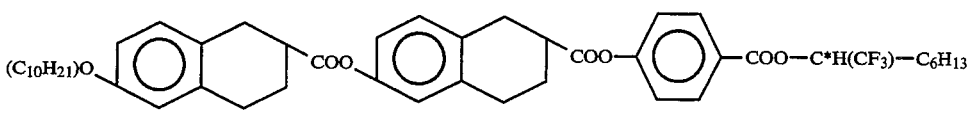
[39]
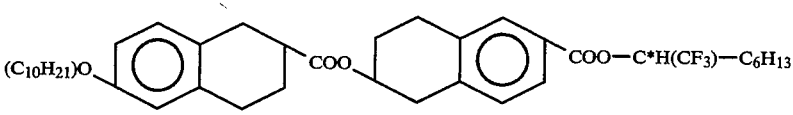
[40]
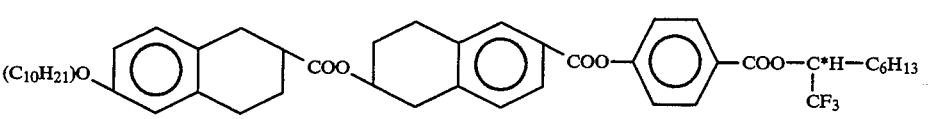
[41]
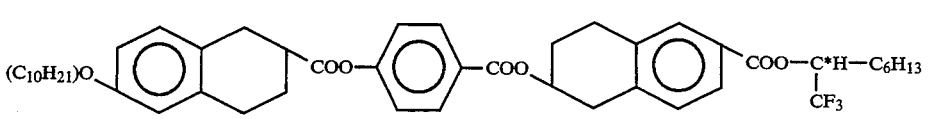
[42]
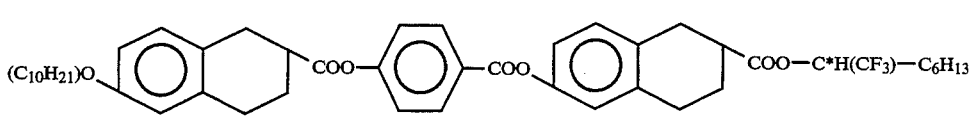
[43]
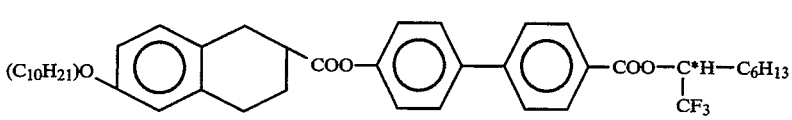
[44]
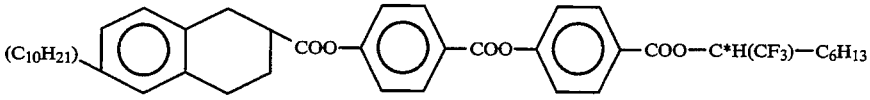
[45]
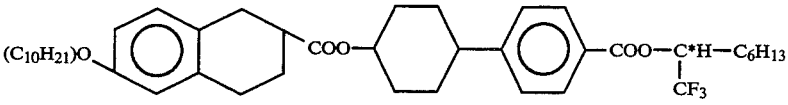
[46]
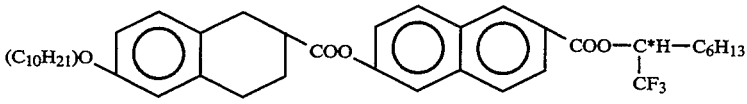
[47]
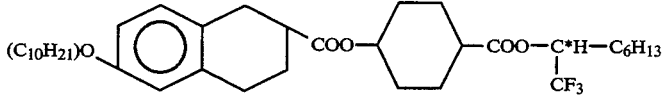
[48]
The carboxylate compounds as exemplified above may be prepared by utilizing a combination of known synthesis techniques.
For example, the above-exemplified carboxylate compounds may be synthesized through such synthesis route as illustrated below.

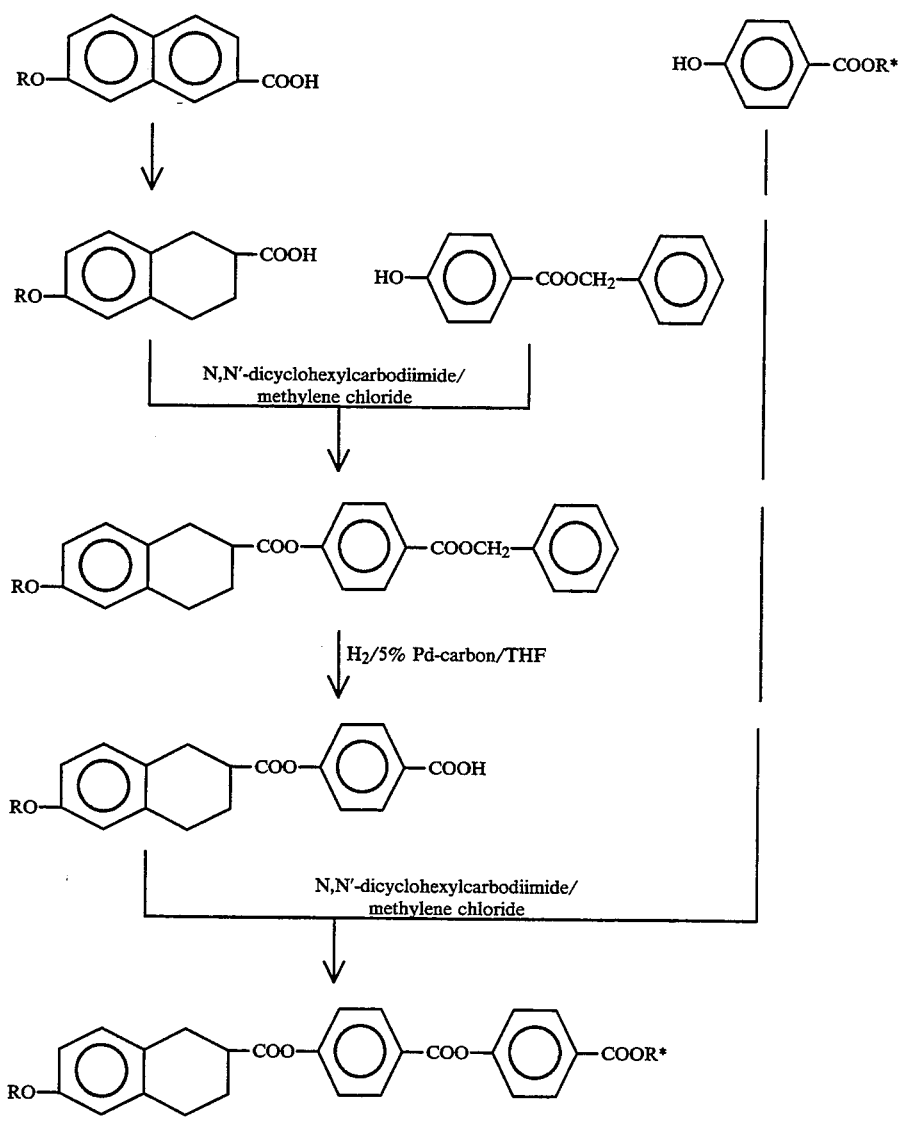

That is, 1,2,3,4-tetrahydro-6-n-alkoxynaphthalene-2-carboxylic acid is obtained, for example, by refluxing a mixture of 6-n-alkoxynaphthalene-2-carboxylic acid and 1,2-ethoxyethane in the presence of metallic sodium while adding dropwise isoamyl alcohol.

The thus obtained 1,2,3,4-tetrahydro-6-n-alkoxynaphthalene-2-carboxylic acid is allowed to react with 4-hydroxybenzoic acid benzyl ester using 4-N,N-dimethylaminopyridine and methylene chloride as solvent while adding dropwise a solution of N,N'-dicyclohexylcarbodiimide to obtain 4-(1',2',3',4'-tetrahydro-6'-n-alkoxy-2'-naphthoyloxy)benzoic acid benzyl ester. The thus obtained 4-(1',2',3',4'-tetrahydro-6'-n-alkoxy-2'-naphthoyloxy) benzoic acid benzyl ester is poured in a solvent such as tetrahydrofuran, and reduced with hydrogen gas in the presence of a reduction catalyst such as a catalyst composed of palladium on carbon to obtain 4-(1',2',3',4'-tetrahydro-6'-n-alkoxy-2'-naphthoyloxy)-benzoic acid.

Subsequently, an ester compound obtained from hydroxybenzoic acid and alcohol haing an asymmetric carbon atom is allowed to react with 4-(1',2',3',4'-tetrahydro-6'-n-alkoxy-2'-naphthoxyloxy)benzoic acid obtained in the above step using 4-N,N-dimethylaminopyridine and methylene chloride as a solvent while adding dropwise a solution of N,N'-dicyclohexylcarbodiimde to obtain the carboxylate compound of the present invention.

The process as mentioned above is given as an example of the processes for preparing the carboxylate compounds of the invention, and it should be construed that the carboxylate compounds of the invention are not limited to the above-mentioned process.

Shown in FIG. 1 is a $^1$H-NMR spectrum chart of R-1'''-trifluoromethylheptyl 4-[4'-(1'',2'',3'',4''-tetrahydro-6''-n-decyloxy-2''-naphthoyloxy) benzoyloxy]benzoate of the following formula selected, for example, out of the carboxylate compounds of the invention prepared by the above-mentioned process.

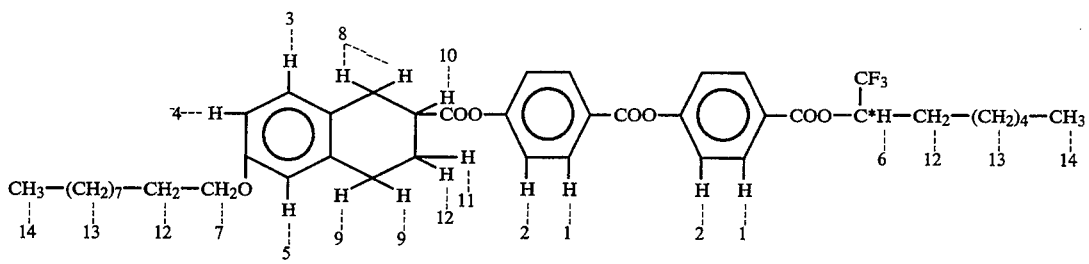

In the above-mentioned formula, numerals 1 to 14 indicate the numbers of hydrogen atoms, and the numbers correspond to numbers attached to the peaks shown in FIG. 1.

Figure 2:
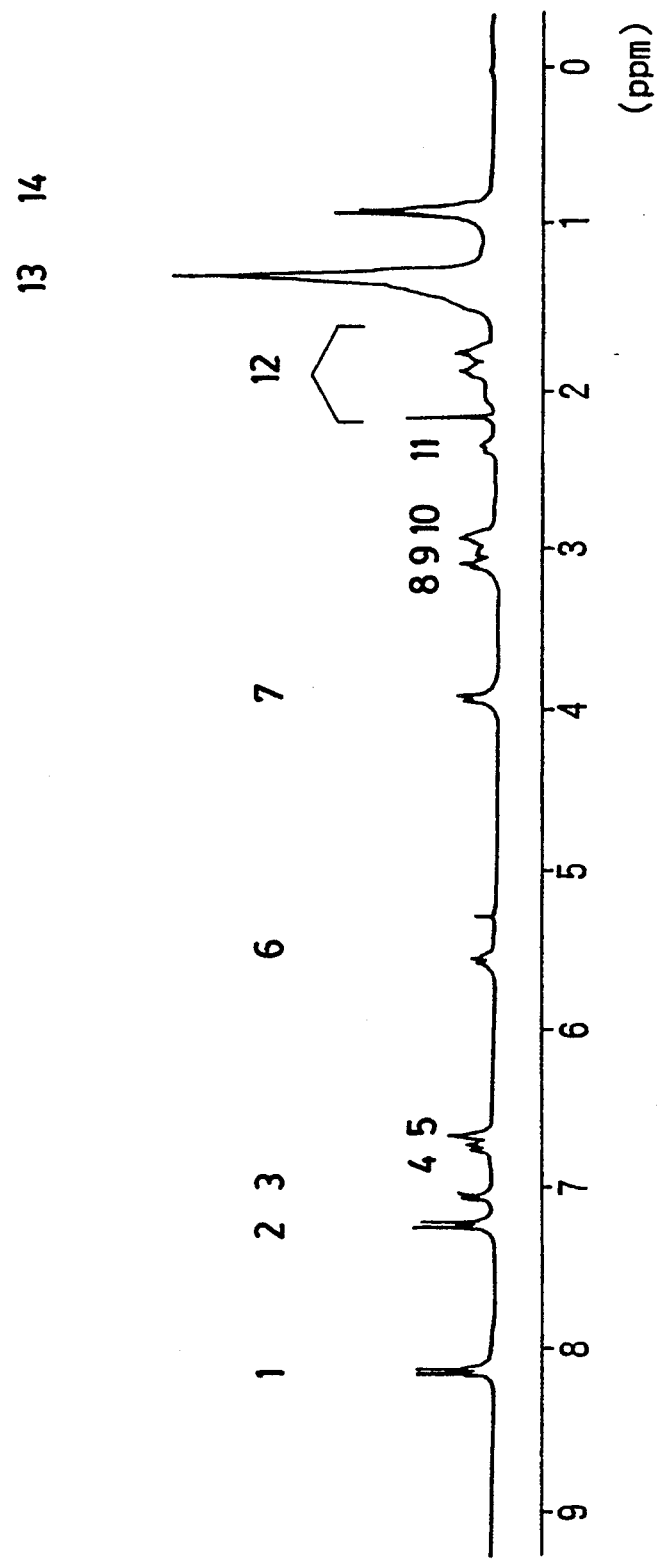
FIG. 2 is a chart showing $^1$H-NMR spectrum of R-1''-trifluoromethylheptyl 4-(1',2',3',4'-tetrahydro-6'-n-decyloxy-2'-naphthoyloxy)-benzoate.

Shown in FIG. 2 is a $^1$H-NMR spectrum chart of R-1″-trifluoromethylheptyl 4-(1′,2′,3′,4′-tetrahydro-6′-n-decyloxy-2′-naphthoyloxy)benzoate of the following formula selected out of the carboxylate compounds of the invention prepared by the above-mentioned process.

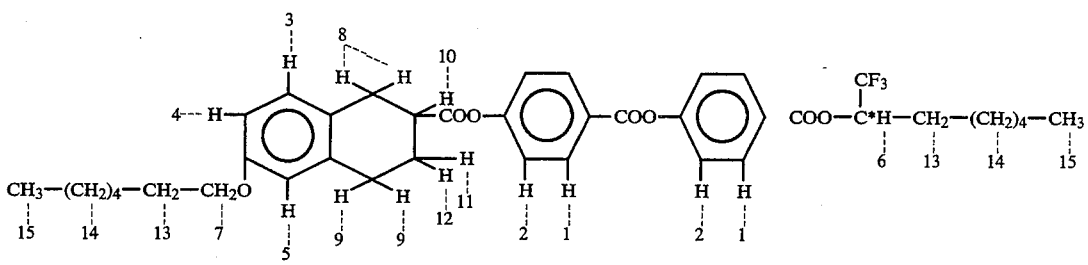

In the above-mentioned formula, numerals 1 to 14 indicate the numbers of hydrogen atoms, and the numbers correspond to numbers attached to the peaks shown in FIG. 2.

Figure 3:
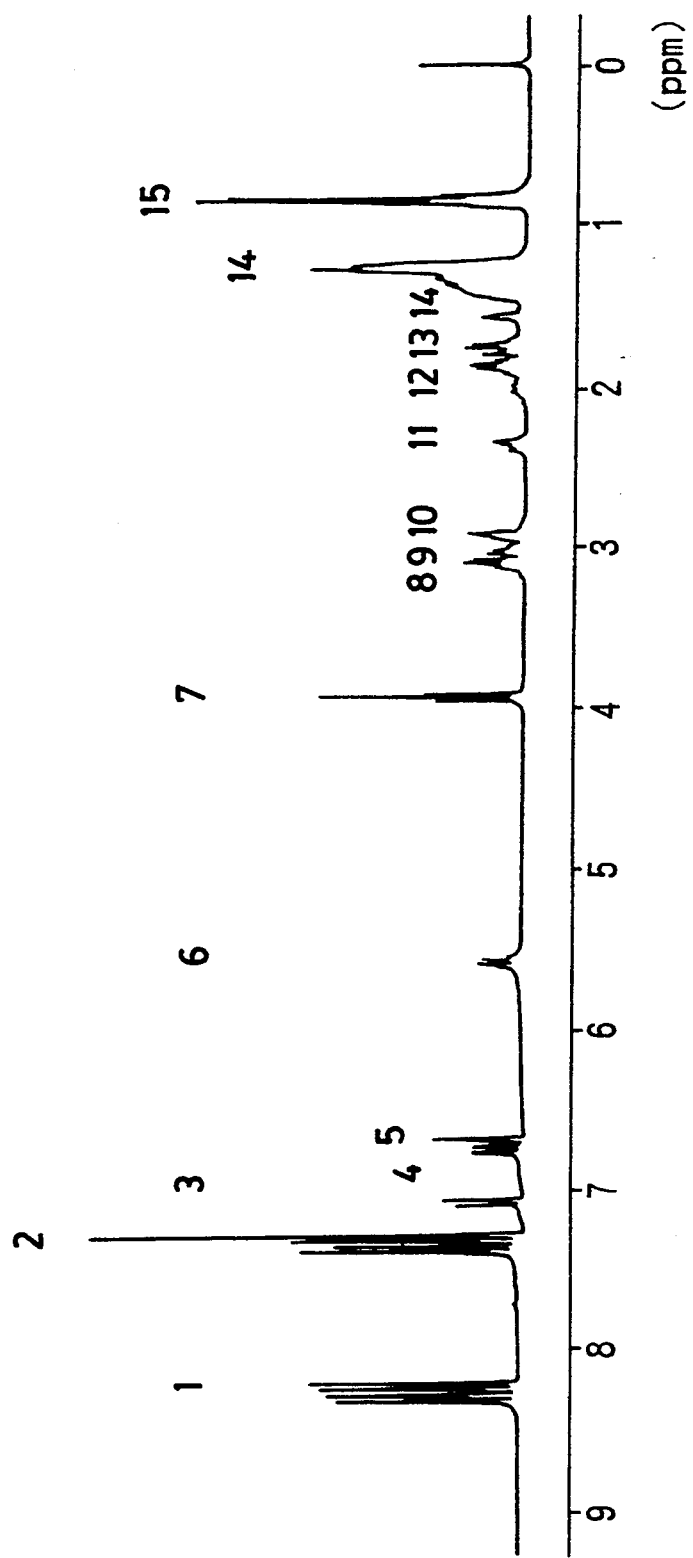
FIG. 3 is a chart showing $^1$H-NMR spectrum of R-1'''-trifluoromethylheptyl 4-[4'-(1'',2'',3'',4''-tetrahydro-6''-n-heptyloxy-2''-naphthoyloxy)benzoyloxy] benzoate.
Figure 4:
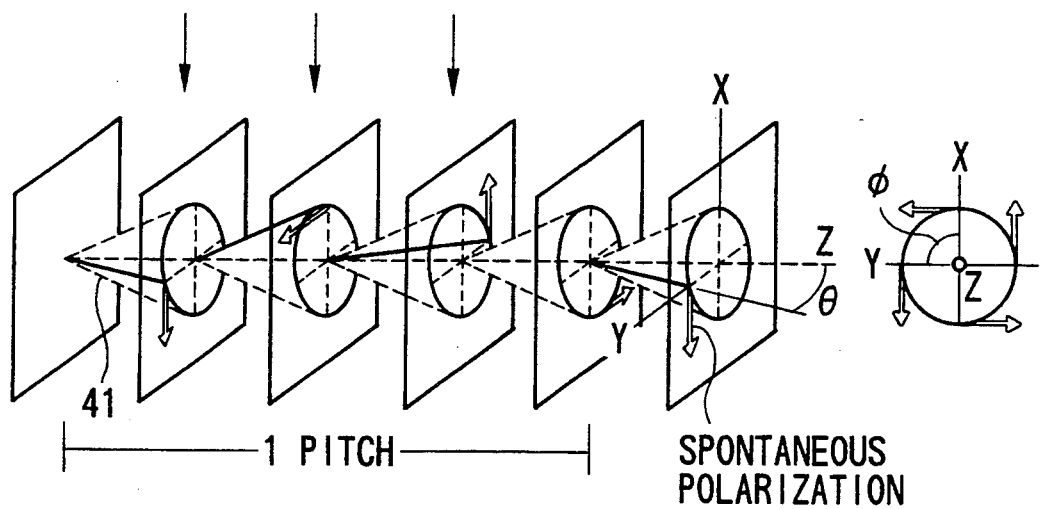
FIG. 4 is a sketch illustrating that each major axis of the molecule of ferroelectric liquid crystal tilts by a tilt angle to the vertical direction of a smetic layer, and the direction of the tilt rotates every smetic layer by a definite angle one by one, thereby assuming a helical structure.
Figure 5:
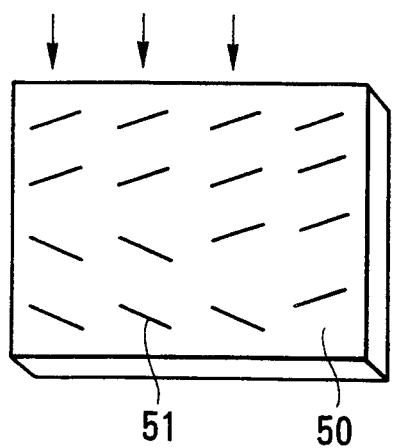
FIG. 5 is a sketch showing the state of a conventional film element wherein two types of the direction of orientation can be attained.

Shown in FIG. 3 is a $^1$H-NMR spectrum chart of R-1‴-trifluoromethylheptyl 4-[4′-(1″,2″,3″,4″-tetrahydro-6″-n-heptyloxy-2″-naphthoyloxy)benzoyloxy]benzoate of the following formula selected out of the carboxylate compounds of the invention prepared by the above-mentioned process.

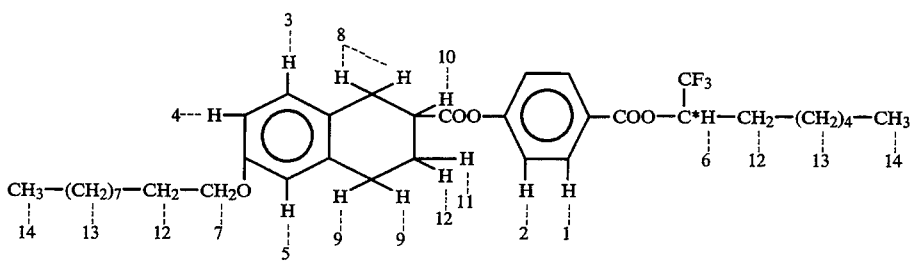

In the above-mentioned formula, nemerals 1 to 15 indicate the number of hydrogen atoms, and the numbers correspond to numbers attached to the peaks shown in FIG. 3.

The carboxylate compounds of the formula [A] obtained in the manner now described may be used, for example, as liquid crystal compounds.

Particularly, the carboxylate compounds having optical activity may be used as ferroelectric or anti-ferroelectric liquid crystal compounds.

Of such carboxylate compounds as mentioned above, those represented by the following formulas [5], [8] and [13] exhibit particlarly excellent liquid crystal properties.

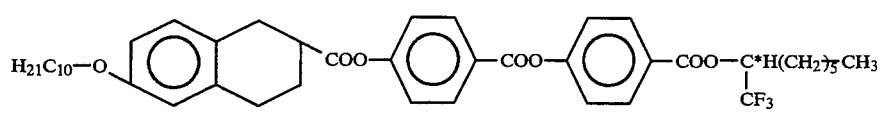

[5]

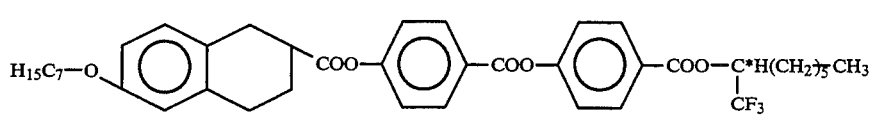

[8]

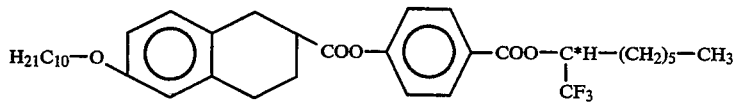

[13]

The phase transition temperatures of the compounds represented respectively by the formulas [5], [8] and [13] which are particularly excellent as liquid crystal compounds are shown in Table 1. In this table, Cry represents a crystal phase, SmC reprsents a chiral smectic phase, SmA represents a smectic A phase, and Iso represents an isotropic liquid.

TABLE 1

| Compound | Phase transition temperature | | |
|---|---|---|---|
| | Cry-SmC or SmA | SmC-SmA | SmA-Iso |
| [1] | 30° C. | | 72° C. |
| [5] | 44° C. | 78° C. | 94° C. |
| [8] | 38° C. | 47° C. | 105° C. |
| [13] | −14° C. | | |

In the liquid crystal compounds of the invention, many compounds assume smectic phase over a wide temprature range as shown in Table 1.

When conventional liquid crystal compounds are used singly, there are scarcely known liquid crystal compounds assuming smectic phase over a wide tempreature range as wide as 100° C. as in the case of the above-mentioned compounds of the invention.

The liquid crystal compounds of the invention assume smectic phase over a wide temperature ranges, and optical-switching elements prepared using such liquid crystal compounds are excellent in high-speed response.

The liquid crystal compounds of the invention may be used singly, and they may also be used as liquid crystal compositions in admixture with other liquid crystal compounds. For example, the liquid crystal compounds of the invention may be used as a principal ingredient in a chiral smectic liquid crystal composition or the compounds may also be used as minor ingredient in a liquid crystal composition containing other compound assuming smectic phase as a principal ingredient.

In either case, at least one of the above-mentioned liquid crystal compounds of the formula [A] is contained in the liquid crystal compositions of the invention.

In the liquid crystal compositions of the invention, the content of the liquid crystal compound of the formula [A] may be 1-99 parts by weight, preferably 5-75 parts by weight based on the total amount of the liquid crystal materials present in the composition, taking the characteristics, of the liquid crystal compound used, the viscosity, operating temperature and application of the composition into consideration.

The liquid crystal compounds used in the invention, either one or two or more, may be incorporated into the liquid crystal composition.

In liquid crystal compounds which exhibit ferroelectricity like the carboxylate compounds used in the invention, an optical switching phenomenon is induced by application of voltage thereto and, therefore, display devices having good response may be prepared therefrom by utilizing this phenomenon.

The ferroelectric liquid crystal compounds used in such display devices as mentioned above are those assuming any one of a chiral smectic C phase, a chiral smectic F phase, a chiral smectic G phase, a chiral smectic H phase, a chiral smectic I phase, a chiral smectic J phase and a chiral smectic K phase. However, display devices using these liquid crystal compounds are generally slow in response speed except the compounds assuming a chiral smectic C phase (SmC* phase). Accordingly, driving with a chiral smectic C phase having a quick response speed has heretofore been considered to be advantageous in practical use.

However, the ferroelectric liquid crystal compositions may be used not only in the chiral smectic C phase but also in the smectic A phase by utilizing a method of driving display devices in the smectic A phase as proposed previously by the present inventors (Japanese Patent Application No.157808/1987).

Because the liquid crystal compounds of the invention exhibit more than two steady states even in liquid phase such as a chiral smectic F phase having a degree of order higher than that of a chiral smectic C phase, they are capable of performing optical switching in the same manner as in the case of a smectic A phase. Accordingly, by using the liquid crystal compositions of the invention containing such carboxylate compounds as mentioned above, there may be obtained liquid crystal elements having a wider liquid crystal temperature range and high-speed electric-optical correspondence.

Table 2 mentioned below shows a case wherein a liquid crystal composition comes to have a wider phase transition temperature range by using such carboxylate compound as mentioned above in the composition. As shown in Table 2, the liquid crystal composition comes to have a wider phase transition tmperature range by using R-1'''-trifluoromethylheptyl 4-[4'-(1'',2'',3'',4''-tetrahydro-6''-decyloxy-2''-naphthoyloxy)benzoyloxy]-benzoate in the composition in combination with a liquid crystal compound represented by the following formula [B].

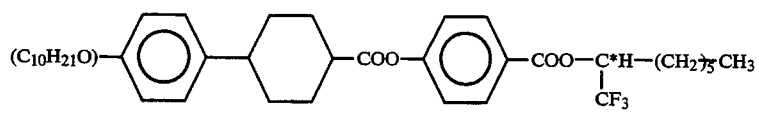

[B]

Concretely speaking, the phase transition temperature of from the smectic phase to liquid rises from 53° C. to 72° C. while maintaining the transition temperature of Cry-SmC* at −30° C.

TABLE 2

| Compound or Composition | Phase transition temperature | | |
|---|---|---|---|
| | CRY—SmC* or SmA | SmC*—SmA | SmA—Iso |
| [5] | 44° C. | 78° C. | 94° C. |
| [5] 50 wt % + (B) 50 wt % | <−30° C. | 50° C. | 72° C. |
| (B) | 26° C. | 38° C. | 40° C. |

Note:
In the above Table, [5] represents the compound represented by the following formula,

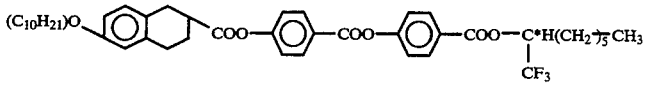

and (B) represents the compound represented by the following formula.

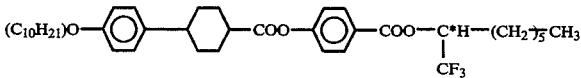

Examples of liquid crystal compounds which can be used together with the carboxylate compounds of the above-mentioned formula [A] in the liquid crystal compositions of the invention include (+)-4′-(2″-methylbutyloxy)phenyl-6-octyloxynaphthalene-2-carboxylic acid ester, 4′-decyloxyphenyl-6-((+)-2″-methylbutyloxy) naphthalene-2-carboxylic acid ester,

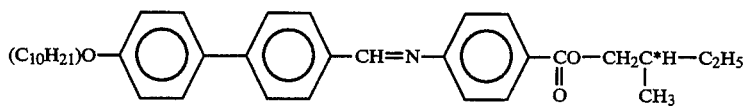

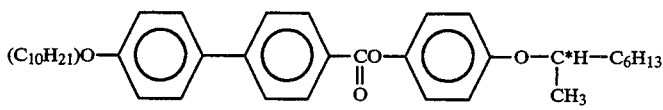

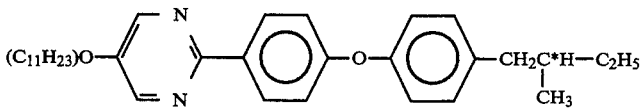

shiff base type liquid crystal compounds such as

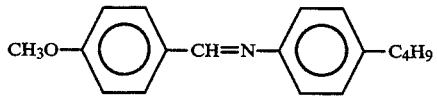

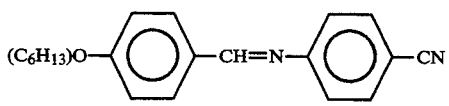

azoxy type liquid crystal compounds such as

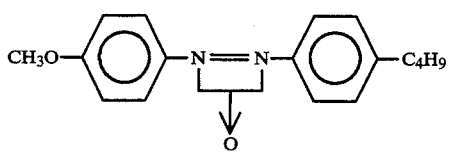

benzoic acid ester type liquid crystal compounds such as

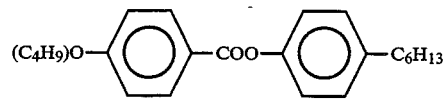

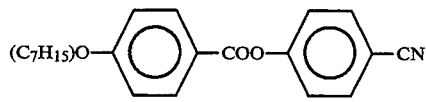

cyclohexylcarboxylic acid ester type liquid crystal compounds such as

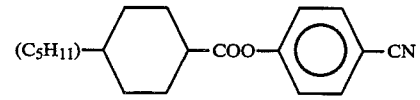

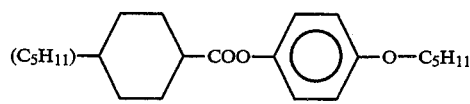

biphenyl type liquid crystal compounds such as

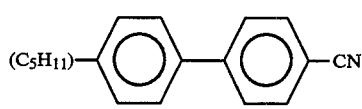

terphenyl type liquid crystal compounds such as

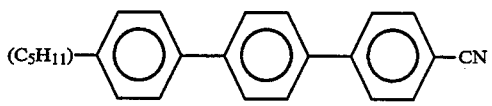

cyclohexyl type liquid crystal compounds such as

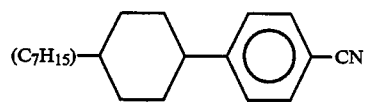

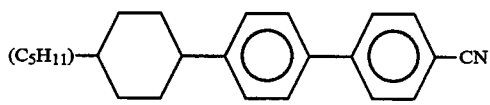

and pyridine type liquid crystal compounds such as

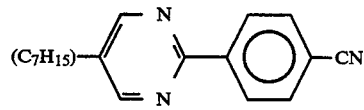

As can be seen from the above Table 2, a liquid crystal material comprising the carboxylate compound of the invention represented by the above-mentioned formula [A] solely or together with the other liquid crystal compound indicates smectic phase over a wide temperature range, that is to say that the carboxylate compound of the invention can be used as a liquid crystal compound or liquid crystal modifying agent used together with other liquid crystal compound.

When display elements for example, those as will be mentioned later, are formed by using the liquid crystal compositions of the invention, additives which can be incorporated into ordinary liquid crystal compositions, for example, conductivity imparting agents and lifetime improving agents, may be added to the present liquid crystal compositions in addition to the above-mentioned carboxylate compounds and other liquid crystal compounds. Further, dichroic dyes can be incorporated into the liquid crystal compositions of the invention when said liquid crystal compositions are used in liquid crystal elements driven by a driving system utilizing the dichroism of dyes.

The liquid crystal compositions of the invention may be prepared by mixing the above-mentioned carboxylate compounds with other liquid crystal compounds and additives if desired.

Liquid Crystal Element

The liquid crystal elements according to the present invention are now illustrated hereinafter with reference to FIGS. 6(A) and 6(B) each showing a section of one embodiment of liquid crystal elements of the invention.

The first liquid crystal element of the invention comprises basically a cell 63 composed of two sheets of transparent substrates 61a and 61b facing each other, and a liquid crystal material 65 charged into a space 64 formed between said substrates 61a and 61b. In other words, the first liquid crystal element of the invention comprises basically a cell 63 composed of the substrates 61a and 61b (hereinafter simply called the substrate) having formed a space 64 therebetween, and a liquid crystal material 65 charged into the space 64 of the cell 63.

In the substrates as mentioned above, at least one of them must be transparent, and usually such a transparent substrate as used herein is made of glass or a transparent plastic such as polycarbonate, 4-methyl-1-pentene polymer or copolymer, amorphous polyolefin such as copolymer of ethylene and tetracyclo[4,4,0,1$^{2.5}$,1$^{7.10}$]3-dodecene.

When a glass substrate is used in the above case, an under coat layer (an unnecessary component permeation preventing layer) comprising such a material, for example, as silicon oxide or the like may also be provided on the inner surface of the glass substate in order to inhibit deterioration of the liquid crystal material used due to elution of alkali component from said glass substrate.

The transparent substrate, when it is a glass substrate, has a thickness of from 0.01 to 1.2 mm in most cases.

In the present invention, there may also be used transparent flexible substrates as the transparent substrates. In that case, at least one of the transparent substrates may be a flexible transparent substrate or both of them may be flexible transparent substrates.

Useful flexible transparent substrates include, for example, films made of polymer materials.

In these substrates 61a and 61b as illustrated above, usually an electrode 62a and 62b composed of indium-tin oxide are provided on the inner surface thereof, that is, the surface that faces toward the liquid crystal material. In the invention, a transparent electrode substrate composed of a transparent electrode integrally formed on the above mentioned substrate may also be used as the substrate.

The transparent electrode may be formed, for example, by coating indium oxide or tin oxide on the surface of transparent substrate according to the method, per se, known.

The transparent electrode is provided usually to a thickness of from 100 to 2000 Å.

In the liquid crystal element of the invention, it is preferable that an orientation controlling film (orientation layer) is provided on the inner surface of at least one of the two sheets of substrates, particularly on the inner surface of each substrate. FIG. 6(A) shows an embodiment in which two sheets of orientation controlling films 67a and 67b are provided.

The orientation controlling film used in the invention includes organic or inorganic films made of polyimide, silicon oxide, polyvinyl alcohol, polyamide, polyester or the like. Of these films, particularly preferred is a polyimide film.

In preferred embodiments, for example, when one sheet of the orientation controlling film is provided, this one sheet of the orientation controlling film is composed of polyimide, and when two sheets of the orientation controlling film are provided, at least one of them is composed of polyimide, preferably both of them are composed of polyimide.

The polyimide used in that case may be any of polyimides so long as they are polymer materials having imido linkage in the molecule, and such polyimides have preferably those capablity of film forming. Concrete examples of the polyimides include Uprex R (a product of Ube Industries, Ltd.), Sunever 130 (a product of Nissan Chemical Industries, Ltd. ), OPTOMER AL1251, JIA-28 (a product of Japan Synthetic Rubber Co., Ltd.), KERMIMID 601 (a product of Nippon Polyimide Co., Ltd.) and HL-1100, LX-1400 (a product of Hitachi Kasei Kogyo K.K.). However, the polyimides used in the invention are not limited to those mentioned above.

As stated above, the polyimides used in the invention are resins consisting essentially of a polymer material having imido linkage. The orientation controlling film used in the invention, however, may contain other resins such as polyamide in addition to the polyimide in such an amount not to have an adverse effect on characteristics of the polyimide, and such resins may be those containing other structural units in addition to imido structural units.

When one of the orientation controlling films is from a material other than the polyimide, this orientation controlling film composed of other material than the polyimide may be composed of an organic or inorganic material.

Examples of the orientation controlling film composed of other material than the polyimide include those composed of such resins, for example, as polyvinyl alcohol, polyamideimide, polyester, polycarbonate, polyvinyl acetal, polyvinyl chloride, polyvinyl acetate, polyamide, polystyrene, siloxane polyimide, cellulose resin, melamine resin, urea resin, acrylic resin and electrically conductive polymer. Further, the orientation controlling film may be a cured article of cyclized rubber photoresist, phenol novolak photoresist or electron beam photoresist such as polymethyl methacrylate or epoxidized 1,4-polybutadiene. Further, the orientation controlling film may be formed from an inorganic material, for example, $SiO$, $SiO_2$, $GeO$, $Al_2O_3$, $Y_2O_5$, $ZrO_2$, $MgF_2$ or $CeF_3$.

The orientation controlling film may be formed on the inner surface of each substrate in contact with a liquid crystal by various methods depending on the material used for forming said film, such as a method wherein the above-mentioned resin is applied, for example, by means of spin coating, a method wherein the thus coated resin is heat treated, a method wherein a resin film is laminated, a method wherein a photosensitive resin is applied and then cured by irradiation with an energy ray, and a method wherein an inorganic material is deposited.

Furthermore, the orientation controlling film (orientation layer) may be formed, for example, by chemical adsorption of an organosilane coupling agent or a polynuclear complex of carboxylic acid, or by rhombic deposition of silicon oxide or the like. The orientation layer may also be formed by applying a polyimide resin on the transparent electrode, followed by rubbing the coated polyimide resin in a definite direction.

The orientation layer may be so formed as to serve simultaneously as a spacer as will be mentioned later.

Two sheets of the transparent substrates 61a and 61b as illustrated above are arranged in such a manner that two sheets of the transparent electrodes 62a and 62b are formed on the two sheets of transparent substrates, respectively, so that said two sheets of the transparent electrodes face each other, and that a space into which a liquid crystal material is charged is formed by these two sheets of the substrate.

The width of the space thus formed between the substrates is usually 1 to 10 µm, preferably 1 to 5 µm. Such a space as mentioned above may readily be formed, for example, by arranging two sheets of the substrate in position so that the spacer is held between said substrates.

The thickness of the orientation controlling film as illustrated above is in the range of usually 0.005 to 0.25 µm, preferably 0.01 to 0.15 µm.

In the present invention, it is desirable that the above-mentioned two sheets of the orientation controlling film are provided respectively on the inner surface of the substrates so that the orientation direction of a liquid crystal material controlled by one of the orientation controlling film and that of the liquid crystal material controlled by the other are nearly parallel to each other, and the orientation directions of said crystal material are in the same direction or in the opposite direction from each other. However, the arrangement of the orientation controlling films as mentioned above is not critical. The orientation controlling films 67a and 67b have the function in orientating the liquid crystal material in the desired direction. Accordingly, the initial orientation of the liquid crystal material is improved and a liquid crystal element excellent in contrast, etc., is obtained by orientating the liquid crystal material by means of the orientation controlling films so arranged that the orientation directions of said liquid materiel controlled by said orientation controlling films are parallel to each other in the same or opposite direction, as compared with the case wherein the orientation controlling films are arranged is disorderedly.

In the present invention, the orientation controlling film is subjected preferably to orientation treatment. The orientation treatment as referred to herein is intended to designate the treatment for orientating the liquid crystal molecule in the predetermined direction, for example, a polyimide film may be orientated by rubbing said film with cloth or the like in a given direction.

The cell used in the invention comprises two sheets of the transparent substrates 61a and 61b provided, if necessary, with the orientation controlling films 67a and 67b, respectively, in the manner now described, and a space 64 into which the liquid crystal material is charged. The space 64 may be formed, for example, by putting spacers 68 as inner sidewalls between the substrates 61a and 61b. By virtue of providing the spacers 68 in this manner, the space 64 to be filled with the liquid crystal material can be secured and the liquid crystal material charged into the space 64 can be prevented from leaking. The space 64 can be formed by using the above-mentioned spacers capable of forming sidewalls. Alternatively, the space can also be formed by mixing particles (internal spacer) having the predetermined particle diameter with the liquid crystal material.

Useful spacer (internal spacer) as referred to above includes, for example, a polyimide type polymer material obtained by patterning of a photosensitive polyimide precursor. By virtue of using such a spacer as mentioned above, a monodomain is formed by interfacial effect of this spacer with the liquid crystal material. The orientation film and spacer can also be integrated into one system by using a concentric circular or comb-like spacer which is serviciable as an orientation film.

In addition to the use of the above-mentioned spacers, a given space can be formed between the substrates by mixing fiber with the liquid crystal material so that the substrates form the given space therebetween by the presence of this fiber.

In that case, moreover, the liquid crystal material can be mixed with particles (internal spacer) in place of the fiber, or may be mixed with the fiber together with the particles.

The particles as referred to above include those made of melamine resin, urea resin or benzoguanamine resin having a particle diameter of from 1 to 10 μm.

The width of the thus formed space between the substrates is usually from 1 to 10 μm, preferably from 1 to 5 μm and especially from 1.6 to 5 μm.

In two sheets of the transparent substrate so arranged as to form a space therebetween by means of a spacer in the manner described above, the peripheries of said substrates are sealed usually with a sealing compound. Such a sealing compound includes epoxy resin, silicone resin, ultraviolet ray curing resin, etc. which may be modified with acrylic material or silicone rubber.

In the liquid crystal element of the invention, various thin films such as a photoconductive film, light screening film, light reflecting film or the like may be provided on the opposite surface of the orientation controlling film formed on the substrate.

In the liquid crystal element, the liquid crystal material 65 is charged into the space 64 of the cell as mentioned above.

The liquid crystal materials used in the invention include carboxylate compounds represented by the aforementioned formula [A]. In the invention, in particular, it is desirable to use liquid crystal compositions containing at least one carboxylate compound of the formula [A], though the carboxylate compound of the formula [A] may also be used singly.

The liquid crystal element of the invention as illustrated above is markedly excellent in contrast, etc., and so may be favorably used as a surface stabilized ferroelectric liquid crystal element, helically strained type element, transient scattering type element, guest-host type element and vertical orientation liquid crystal element.

Using the liquid crystal elements according to the invention, various liquid crystal display devices and electrooptical display devices can be prepared.

Of the liquid crystal elements of the invention, those comprising a cell filled with a liquid crystal composition assuming a smectic phase can be used as memory liquid crystal display devices such as heat writing display element, and laser writing display element. Liquid crystal display devices or electrooptical display devices can be prepared by using such liquid crystal elements, and crystal display devices or electrooptical display devices can be prepared by using such-liquid crystal elements.

In addition to the above-mentioned applications, the liquid crystal element of the invention in which a liquid crystal composition containing a carboxylate compound having ferroelectricity is contained can be used as liquid crystal elements such as optical switching elements, e.g., optical shutter and liquid crystal printer, piezoelectric elements and pyroelectric elements, and liquid crystal display devices or electrooptical display devices may be prepared by using such liquid crystal elements.

Namely, when a chiral smectic C phase is formed by using the liquid crystal materials used in the invention, the chiral smectic C phase thus formed exhibits double state stability. Accordingly, when electric field is inverted between bi-stable states, optical switching and display can be performed by using such liquid crystal element as containing a ferroelectric liquid crystal material assuming a chiral smectic C phase.

Further, because such ferroelectric liquid crystal material as assuming a chiral smectic C phase has spontaneous polarization, when voltage is once applied to a cell of liquid crystal element containing said material, the cell will come to have a memory effect even after the electric field is erased. By utilizing this memory effect, therefore, a power consumption of the display device comprising such liquid crystal element can be reduced. In this case, moreover, the contrast of the display device is stabilized and becomes very clear.

The switching element using this chiral smectic liquid crystal compound or composition can be driven at low voltage, because switching can be performed only by changing the direction of molecular orientation of the chiral smectic liquid crystal compound and also because the primary strength of electric field applied to the driving.

When this switching element is used, a high speed response of not more than scores of micro second can be attained. Accordingly, the scanning time of the element can be greatly shortened and a large screen display (liquid crystal display device) having a number of scanning lines can be prepared. Moreover, because this display can be operated at room temperature or lower, scanning can be easily made without using any auxiliary means for temperature control.

Further, the molecules of the liquid crystal materials used in the liquid crystal elements of the invention are tilted causatively even in the state of a smectic A phase exhibiting no double state stability when an electric field is applied, hence optical switching can be conducted by utilizing this property.

Process for Preparing Liquid Crystal Element

A process for preparing the above-mentioned liquid crystal element is illustrated below in detail.

The liquid crystal element of the present invention may be prepared by filling the above-mentioned space between the transparent substrates of the cell with a liquid crystal material including the above-mentioned carboxylate compound.

The liquid crystal material is heated usually to a molten state and then filled (injected) in the above-mentioned space evacuated in advance.

After filling the space with the liquid crystal material, usually the cell is sealed. Subsequently, the liquid crystal material thus filled in the cell is usually subjected to initial orientation. The initial orientation of the liquid crystal material may be performed, for example, by heating the thus sealed cell so that the liquid crystal material present in the cell is heated up to a temperature not lower than the temperature at which said liquid crystal material exhibits an isotropic phase and then cooled to the temperature at which said liquid material exhibit a liquid crystal phase.

In that case, the liquid crystal material is cooled preferably at a rate of not higher than 2° C./min. In particular, this rate of temperature drop employed is preferably in the range of from 0.1° to 2.0° C./min, especially from 0.1° to 0.5° C./min. By cooling the cell at a cooling rate within the range of as defined above, there is obtained a liquid crystal element which is excellent in initial orientation and has a liquid crystal phase. The term initial orientation as used herein refers to the state of arrangement of the liquid crystal material before orientation vector of the liquid crystal material is changed by applying voltage to the liquid crystal element.

Further, the initial orientation of the liquid crystal material thus filled in the space of the liquid crystal cell may be performed, for example, by the temperature gradient method utilizing a spacer edge or the monoaxial orientation controlling method such as surface treatment using an orientation film. In the present invention, moreover, the initial orientation of the liquid crystal material can also be performed by applying an electric field using direct current bias voltage to the liquid crystal material being heated.

The liquid crystal cell thus filled with the liquid crystal material and initially orientated is placed between two polarizing plates, and the two polarizing plates are arranged so that a plane of polarization formed by the polarizing plates has an angle of 70°–110°. Preferably, these two polarizing plates are arranged so that the polarization directions of the polarizing plates meet at right angle, that is, the above-mentioned angle becomes 90°.

Useful as the above-mentioned polarizing plates are polarizing films prepared by stretching such resin film, for example, as polyvinyl alcohol resin film or polyvinyl butyrale resin film in the presence of iodine or the like so as to impart polarization to the stretched films. The polarizing film as illustrated above may also be laminated on the surface with other resin so as to have a multi-layer construction.

In the present invention, the liquid cell can be placed between the polarizing plates as arranged in the manner now described, so that the cell is placed in a state to form an angle (rotation angle) within the range of from +10° to −10° (hereinafter abbreviated to ±10°) from the state wherein the amount of transmitted light is the smallest (i.e. the darkest state), preferably in the darkest state. Alternatively, the liquid crystal cell can be placed in a state to form an angle (rotation angle) within the range of ±10° from the state wherein the amount of transmitted light is the largest (i.e. the brightest state), preferably in the brightest state.

Driving (Display) Method of Liquid Crystal Element

Driving (displaying) the liquid crystal element of the present invention having such structure as mentioned above may be performed, for example, by applying an electric field to said liquid crystal element.

Namely, the liquid crystal element is driven, for example, by applying thereto an electric current of usually 1 Hz–100 KHz, preferably 10 Hz–10 KHz, and an electric field controlled to have a strength of usually 0.01–60 (Vp-p)/$\mu m^2$, preferably 0.05–30 (Vp-p)/$\mu m^2$.

When the liquid crystal element is driven by application of an electric field, the amount of light that transmits this element comes to exhibit two kinds of hysteresis curves by changing a wave form (driving wave) of the electric field applied. That is, the present inventor has been successful in exhibiting memorization in one liquid crystal element by employing two kinds of driving methods. Of the two driving methods, one is to utilize so-called double state stability, and the other is to utilize so-called triple state stability.

A liquid crystal element using MHPOBC as a liquid crystal material is known to exhibit triple state stability, but it exhibits practically no double state stability.

It can be first realized by the liquid crystal element of the present invention that either double state stability or triple state stability can be selected in one kind of liquid crystal element only by operation of changing the wave form (driving wave) of the electric field applied thereto.

Figure 7:
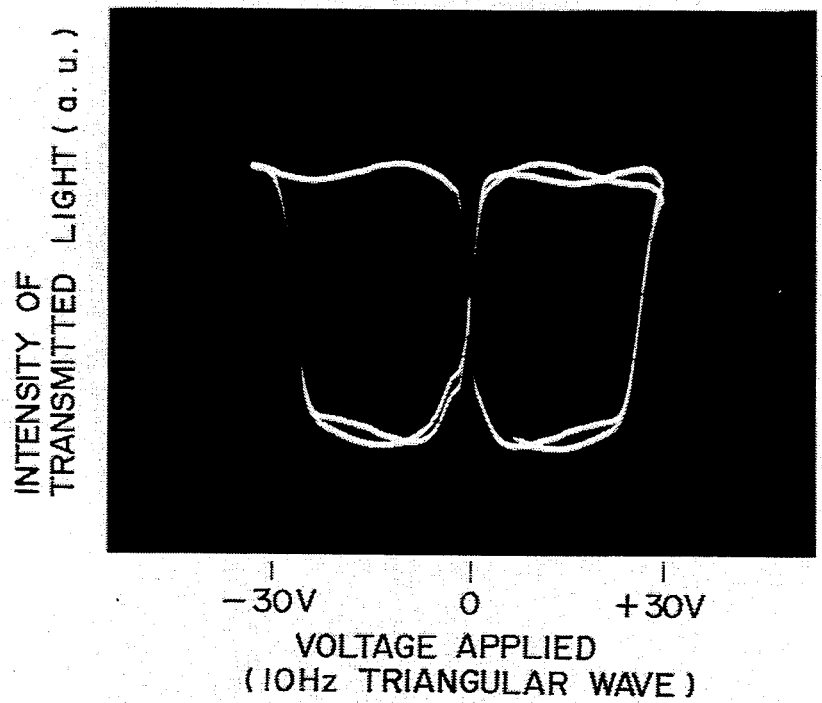
FIGS. 7 and 8 are each a photograph of oscillographic wave showing the relation between a voltage applied at the time when a triangular wave voltage is applied to the liquid crystal element of the present invention in which a liquid crystal cell is arranged so as to obtain the darkest state and an intensity of transmitted light.
Figure 8:
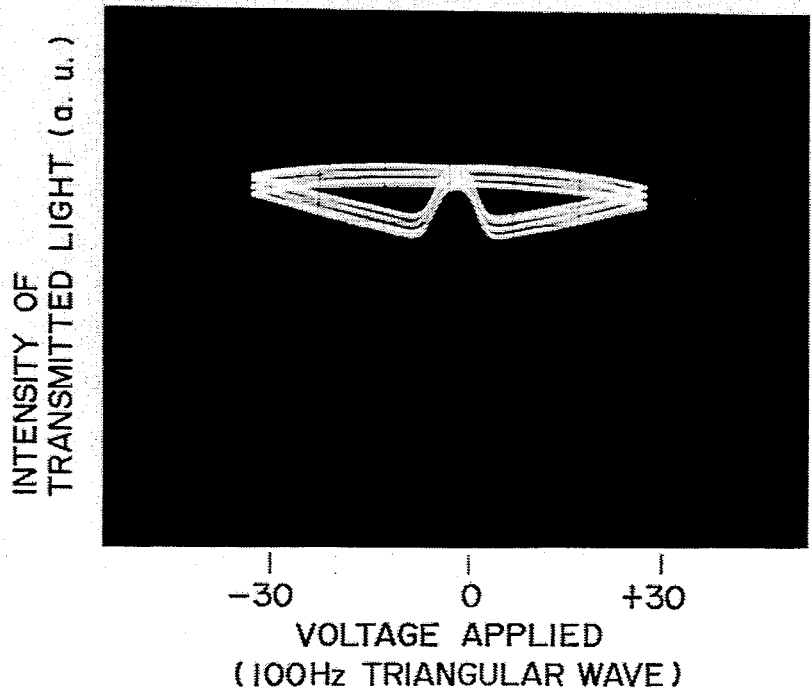

FIG. 7 is an oscillograph of an oscillowave form showing the relation between the amount of transmitted light and applied voltage in a liquid crystal element exhibiting triple state stability, and FIG. 8 is also an oscillograph of an oscillowave form showing said relation in a liquid crystal element exhibiting double state stability.

In the liquid crystal element, used herein, a liquid crystal cell filled with a liquid crystal material is placed between two polarizing plates so arranged that the planes of polarization thereof meet at right angles, so that the darkest state of the element is attained without applying an electric field thereto. FIG. 7 shows an oscillowave form obtained at the time when a triangular wave of 10 Hz is applied to this liquid crystal element, and FIG. 8 shows an oscillowave form obtained at the time when a triangular wave of 100 Hz is applied to this.

In the liquid crystal element where the liquid crystal cell and polarizing plates are arranged so as to obtain the darkest state in the element, a favorable tri-stable state can be realized by application of an electric field of a relatively low frequency, for example, 0.001–50 Hz, preferably 0.1–30 Hz to the element. The oscillowave form is gradually transformed into the bi-stable state as shown in FIG. 8 with increasing frequency of the electric field applied and a favorable bi-stable state can be realized, for example, by applying an electric field having a frequency of 50 Hz–100 KHz, preferably 70 Hz–10 KHz to the liquid crystal element.

In the liquid crystal element as mentioned above, for example, as shown in FIG. 7, a dark state can be attained when the applied voltage is 0(Vp-p), and in this case the contrast obtained becomes markedly high.

Figure 9:
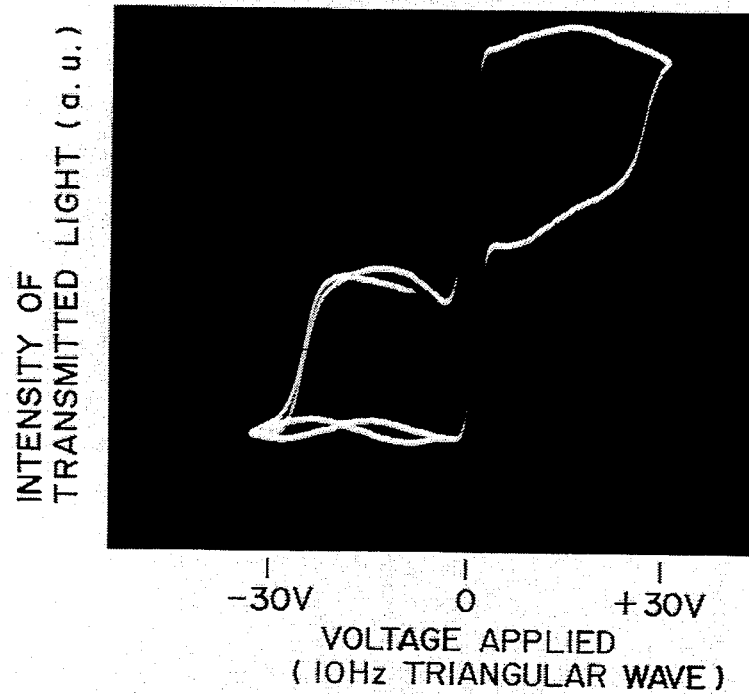
FIGS. 9 and 10 are each photograph of oscillographic wave showing the relation between a voltage applied at the time when a triangular wave voltage is applied to the liquid crystal element of the present invention in which a liquid crystal cell is arranged so as to obtain the brightest state and an intensity of transmitted light.
Figure 10:
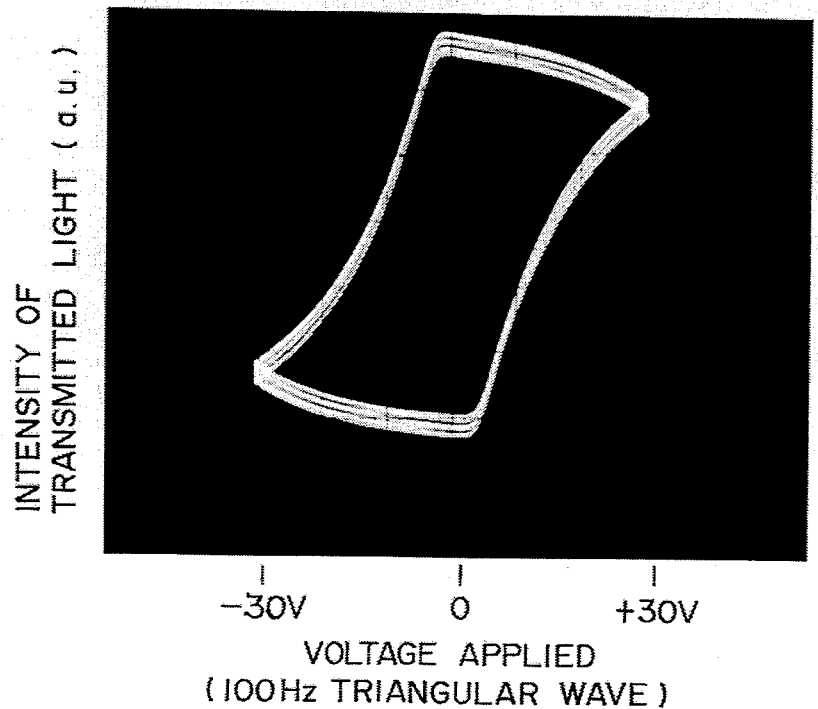

FIGS. 9 and 10 respectively show an oscillowave form of a liquid crystal element in which a liquid crystal cell filled with a liquid crystal material is placed between two polarizing plates whose planes of polarization meet at right angle, so that the brightest state of the element is attained. FIG. 9 shows an oscillowave form obtained when a triangular wave of 10 Hz is applied to the liquid crystal element, and FIG. 10 shows an oscillowave form obtained when a triangular wave of 100 Hz is applied to the liquid crystal element. In this liquid crystal element, there is a tendency similar to that in the liquid crystal element used in FIGS. 7 and 8, for example, a bi-stable state is attained by applying an electric field having a relatively high frequency.

The electric field applied to the above-mentioned liquid crystal elements is preferably selected from among a rectangular wave (or pulse wave), triangular wave, sinusoidal wave and a combination thereof. When a rectangular wave (or pulse wave or a combination of both) is applied to the liquid crystal element, a rate driving the liquid crystal element can be increased by reducing the width of the applied electric field to not more than 10 millisecond, preferably in the range of from 0.01 to 10 millisecond, and in this region, the liquid crystal element of the invention may be used as a bi-stable state type liquid crystal element. Further, by employing this electric field having the width of larger than 10 millisecond, preferably in the range of from 33 to 1000 millisecond, the liquid crystal element of the invention may be used as a tri-stable state type liquid crystal element in the region where no so high driving is required. The width of an electric field as used herein is intended to designate, for example, in a rectangular wave, a length (i.e. time) of the electric field maintained at a given voltage.

To this liquid crystal element, an electric field can be applied while varying it between negative voltage and positive voltage through OV. In the driving method for developing such bi-stable state as shown in FIGS. 8 and 10, a hysteresis curve showing a favorable double state stability can be formed, for example, by varying the applied voltage between −30 V and +30 V. In the liquid crystal element showing a triple state stability, an electric field can be applied in the manner similar to that of the above-mentioned case.

Further, to this liquid crystal element may be applied an electric field having the above-mentioned wave form by varying it between 0 and a positive voltage. Namely, a light modulation method utilizing, for example, light transmission properties shown by a hysteresis curve formed at a plus voltage side by application of an electric field varied in voltage by varying a voltage in the range between 0 and +30 V can be employed. Similarly, a light modulation method utilizing light transmission properties shown by a hysteresis curve formed at a minus voltage side by application of an electric field varied in voltage by varying a voltage in the range between 0 to −30 V can be employed.

The liquid crystal element of the invention is superior to the prior art liquid crystal elements in that the present element can be driven by utilizing two kinds of driving methods as mentioned previously, and it can retain its memory effect by suitably selecting a desired driving method out of the two methods according to the conditions under which it is driven.

The liquid crystal element as mentioned above may be used in applications to which ordinary liquid crystal elements are applied, but said liquid crystal element is particularly useful as a display element.

The display element includes, for example, a liquid crystal large frame display, multi-information display for use in car, navigation display for use in car and display for laptop personal computer. These display elements can be driven, according to the purposes for which they are used, by the above-mentioned driving methods as a bi-stable state liquid crystal element or tri-stable state type liquid crystal element.

The following methods may be given as examples of the display or driving method in which the present liquid crystal elements are used.

The first display or driving method is to effect the display by placing the liquid crystal element of the invention between two polarizing plates and applying an external electric field to said element to change the orientation vector of the ferroelectric or anti-ferroelectric liquid crystal composition present in the element, thereby effecting said display by utilizing a birefringence of the two polarizing plates and of the ferroelectric or anti-ferroelectric liquid crystal composition.

The second display or driving method using the liquid crystal element of the invention comprises using as a liquid crystal material a liquid crystal composition containing a dichroic dye and utilizing the dichroism of the dye. This second method is to effect the display by changing light absorption wavelength by means of the dye while changing the orientation direction of the molecules in the ferroelectric or anti-ferroelectric liquid crystal compound. In this case, the dyes used are usually dichroic dyes, and examples of the dichroic dyes include azo dyes, naphthoquinone dyes, cyanine dyes and anthraquinone dyes.

The liquid crystal elements of the invention may be applicable to commonly used display methods in addition to the above-mentioned methods.

The display devices prepared by using the liquid crystal elements of the invention may be driven by various driving methods, for example, electric address display such as static drive, simple matrix drive and composite matrix drive, and photo-address display, heat address display and electron beam address display.

EFFECT OF THE INVENTION

The carboxylate compound of the present invention is a novel compound.

Though this novel carboxylate compound represented by the above-mentioned formula [A] is not substituted by cyano group in any parts of R, A, B and R* as the above-mentioned Hopf's compound, the compound of the invention solely or together with other compound which may be the same or different kind of a liquid crystal compound indicates the smectic phase over a wide temperature range. Accordingly, the liquid crystal material which consists of the carboxylate compound of the invention solely or the liquid crystal compositon comprising this carboxylate compound is preferably used in the liquid crystal element.

Further, liquid crystal elements having a high speed response over a wide temperature range can be obtained by using the above-mentioned liquid crystal compounds or liquid crystal compositions.

Moreover, scanning time is markedly shortened in the liquid crystal display devices prepared by using such elements as mentioned above.

When such display devices are used, power consumption can be reduced, a stable contrast can be obtained and also a low voltage driving can be performed.

By way of the liquid crystal elements of the invention and the light modulation method using said liquid crystal elements, it becomes possible to attain steady state in two forms, i.e. bi-stable state and tri-stable state.

When the liquid crystal elements of the invention are used, a dark state having a sufficient darkness can be attained, and hence a very high contrast between the bright and dark states can be obtained and, at the same time, a favorable memory effect can be secured.

The present invention is illustrated below with reference to examples, but it should be construed that the invention is in no way limited to those examples.

EXAMPLE 1

Synthesis of R-1'''-trifluoromethylheptyl 4-[4'-(1'',2'',3'',4''-tetrahydro-6''-n-decyloxy-2''-naphthoyloxy)benzoyloxy]-benzoate

First Step

To a mixture of 86 g (11.8 mmol) of 6-n-decyloxynaphthalene-2-carboxylic acid and 130 ml of 1,2-diethoxyethane was added in a nitrogen atmosphere at 120° C. with stirring 3.0 g (130 mg atom) of metallic sodium, and the mixture was then heated to a refluxing temperature.

To this mixture was added dropwise 10 g (114 mmol) of iso-amyl alcohol, and the mixture was allowed to undergo reaction for 1 hour under reflux. After cooling the reaction mixture to room temperature, the metallic sodium remaining in the mixture is decomposed by the addition of ethanol, and the reaction mixture was then acidified with 20% hydrochloric acid.

After addition of 100 ml of water to this reaction mixture, an organic layer was separated therefrom, and this organic layer was washed with water.

The organic layer was concentrated under reduced pressure to obtain 4.25 g of a solid. The solid was recrystallized from toluene to obtain 2.95 g (8.89 mmol) of 1,2,3,4-tetrahydro-6-n-decyloxynaphthalene-2-carboxylic acid.

Second step

To a mixture of 1.66 g (5 mmol) of 1,2,3,4-tetrahydro-6-n-decyloxynaphthalene-2-carboxylic acid obtained in the first step, 1.14 g (5 mmol) of benzyl 4-hydroxybenzoate, 0.12 g (1 mmol) of 4-N,N-dimethylaminopyridine and 20 ml of methylene chloride was added dropwise with stirring at room temperature over a period of one hour.

The reaction was carried out at room temperature for additional 10 hours.

The reaction mixture was filtered and the filtrate was concentrated. Using column chromatography, 2.32 g (4.28 mmol) of benzyl 4-(1',2',3',4'-tetrahydro-6'-n-decyloxy-2'-naphthoyloxy)benzoate as a white solid was separated from the concentrate.

Third step

Hydrogen gas was passed through a mixture of 2.17 g (4 mmol) of benzyl 4-(1',2',3',4'-tetrahydro-6'-n-decyloxy-2'-naphthoyloxy)benzoate obtained in the second step, 1 g of 5% palladium supported on carbon and 30 ml of tetrahydrofuran with stirring at room temperature and ordinary pressure for 8 hours. The reaction mixture was filtered by using Celite which is a filtration assistant and the filtrate obtained was concentrated to obtain 1.59 g (3.52 mmol) of 4-(1',2',3',4'-tetrahydro-6'-n-decyloxy-2'-naphthoyloxy)benzoic acid as a white solid.

Fourth step

To a mixture of 0.45 g (1 mmol) of 4-(1',2',3',4'-tetrahydro-6'-n-decyloxy-2'-naphthoyloxy) benzoic acid obtained in the third step, 0.30 g (1 mmol) of R-1'-trifluoromethylheptyl-4-hydroxybenzoate, 0.012 g (0.1 mmol) of 4-N,N-dimethylaminopyridine and 10 ml of methylene chloride was added dropwise 2 ml of methylene chloride solution containing 0.21 g (0.1 mmol) of N,N'-dicyclohexylcarbodiimide with stirring at room temperature over a period of one hour. The mixture was allowed to undergo reaction at room temperature for 8 hours. The reaction mixture was filtered, and the filtrate obtained was concentrated. The concentrate was separated by using column chromatography to obtain 0.52 g of a colorless semi-solid.

FD-mass spectrum of this semi-solid was measured to obtain an M/e value of 738.

FIG. 1 shows a chart of $^1$H-NMR spectrum of this compound.

From these results of the analyses, the compound was identified to be R-1'''-trifluoromethylheptyl 4-[4'-(1'',2'',3'',4''-tetrahydro-6''-n-decyloxy-2''-naphthoyloxy)benzoyloxy]benzoate which was the desired compound [Exemplified compound (5)].

EXAMPLE 2

Synthesis of R-1'''-trifluoromethylheptyl 4-(1',2',3',4'-tetrahydro-6'-n-decyloxy-2'-naphthoyloxy)benzoate

Fifth step

To a mixture of 0.33 g (1 mmol) of 1,2,3,4-tetrahydro-6-n-decyloxy-naphthalene-2-carboxylic acid obtained in the first step, 0.30 g (1 mmol) of R-1'-trifluoromethylheptyl 4-hydroxybenzoate, 0.012 g (0.1 mmol) of 4-N,N-dimethylaminopyridine and 10 ml of methylene chloride was added dropwise 2 ml of methylene chloride solution containing 0.21 g (1 mmol) of N,N-dicyclohexylcarbodiimide with stirring at room temperature over a period of one hour.

The reaction was carried out at room temperature for 8 hours.

The reaction mixture was filtered and the filtrate obtained was concentrated.

The concentrate was separated by using column chromatography to obtain 0.58 g of a colorless viscous liquid.

FD-mass spectrum of this compound was measured to obtain a M/e value of 618.

FIG. 2 shows a chart of $^1$H-NMR spectrum of this compound.

From these results of the analyses, this compound was identified to be R-1''-trifluoromethylheptyl 4-(1',2',3',4'-tetrahydro-6'-n-decyloxy-2'-naphthoyloxy)benzoate which was the desired compound [Exemplified compound (13)].

EXAMPLE 3

Synthesis of R-1'''-trifluoromethylheptyl 4-[4'-(1'',2'',3'',4''-tetrahydro-6''-n-heptyloxy-2''-naphthoyloxy)benzoyloxy]benzoate Example 1 was repeated except that in place of the 6-n-decyloxy-naphthalene-2-carboxylic acid used in the first step, 6-n-heptyloxy-naphthalene-2-carboxylic acid was used to obtain 0.34 g of a colorless semi-solid.

FD-mass spectrum of this semi-solid was measured to obtain an M/e value of 696.

FIG. 3 shows a chart of $^1$H-NMR of this compound.

From these result of the analyses, this compound was identified to be the desired R-1'''-trifluoromethylheptyl 4[4'-(1'',2'',3'',4''-tetrahydro-6''-n-heptyloxy-2''-naphthoyloxy)benzoyloxy]benzoate [Exemplified compound (8)].

EXAMPLE 4

Phase transition temperatures of Exemplified compound (1), (5), (8) and (13) obtained in Examples 1 and 2, respectively were measured.

Results obtained are shown in Table 3.

TABLE 3

| Compound | Phase transition temperature | | |
|---|---|---|---|
| | Cry-SmC* or SmA | SmC*-SmA | SmA-Iso |
| [1] | 30° C. | | 72° C. |
| [5] | 44° C. | 78° C. | 94° C. |
| [8] | 38° C. | 47° C. | 105° C. |
| [13] | −14° C. | | |

In Table 3, Cry represents a crystal phase, SmC* represents a chiral smectic C phase, SmA represents a smectic A phase, and Iso represents an isotropic liquid.

As is clear from Table 3, the compound (5) and compound (13) assumed a liquid crystal phase over a wide temperature range or below room temperature.

Subsequently, the above-mentioned carboxylate compound (5) and a compound represented by the following formula [B] were mixed together in a ratio of 50:50 by weight to prepare a liquid crystal composition according to the present invention.

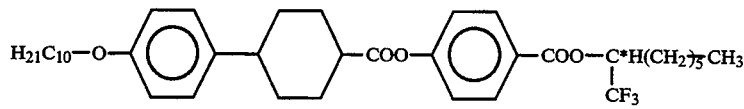

[B]

A phase transition temperature of this composition was measured. Results obtained are shown in Table 4. The phase transition temperature of the above-mentioned compound of the formula [B] is also shown in Table 4.

TABLE 4

| Compound or composition | Phase transition temperature | | |
| --- | --- | --- | --- |
| | CRY—SmC* | SmC*—SmA | SmA—Iso |
| [5] | 44° C. | 78° C. | 94° C. |
| [5] 50 wt % + (B) 50 wt % | <−30° C. | 50° C. | 72° C. |
| (B) | 26° C. | 38° C. | 40° C. |

(Notes)
In the above table, the compound [5] has the following formula

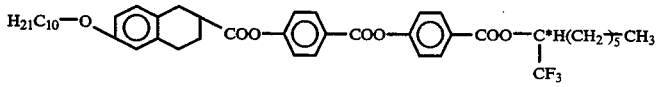

and the compound (B) has the following formula.

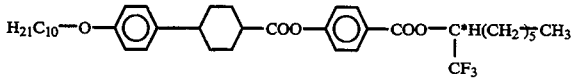

EXAMPLE 5

Figure 6A:
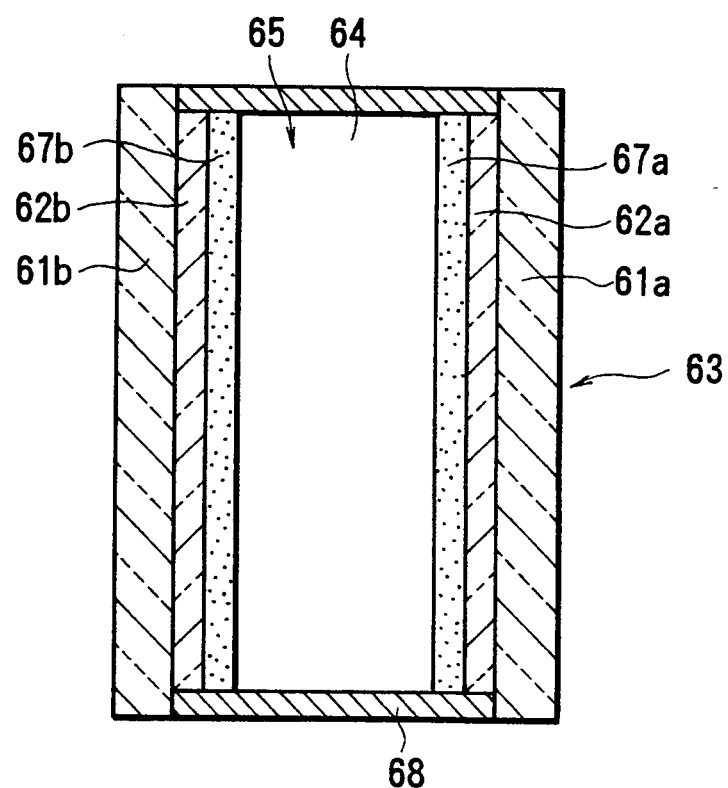
FIGS. 6(A) and 6(B) are each a sectional view showing schematically one embodiment of the liquid crystal elements of the present invention.

A liquid crystal element was prepared by filling the liquid crystal composition into a cell shown in FIG. 6(A).

The operable temperature of the liquid crystal element was from 72° C. to −30° C. and the contrast of the element was stable in the temperature range.

EXAMPLE 6

The carboxylate compound [5] of the formula [2] shown in Table 4 was melted and injected into a gap of a cell, said gap being kept under reduced pressure and said cell being composed of two substrates with ITO transparent electrodes, each substrate being provided with an orientation controlling film (thickness:150 Å) composed of a polyimide (LX1400, a product of Hitachi Kasei Kogyo K.K.) on the inner surface thereof as shown in FIG. 6(A). The polyimide film was rubbed so that orientation directions were nearly parallel to each other and in the same direction. The cell thus filled with the liquid crystal material wad heated to 120° C., kept at 120° C. for 5 minutes and cooled at a rate of 1° C./min to 60° C. to prepare a liquid crystal element.

The contrast of the liquid crystal element was measured. The contrast was 20.

Cell condition:
(a) External size: 2.5 cm long×2.2 cm width×1.5 mm thick
(b) Substrate: 0.7 mm thick, material: glass
(c) Distance between substrates: 2 μm
(d) Sidewall size: 1.8 mm long×0.1 cm width×2 μm thick The above cell used for evaluation of liquid crystal was prepared in the following manner.

Polyimide coating was conducted on a glass substrate with ITO transparent electrode film. That is, the polyimide (LX1400, a product of Hitachi Kasei Kogyo K.K.) was applied on the ITO transparent electrode by a spin coating method. The polyimide was diluted with N-methylpyrrolidone to a 1.2% solution which was then spin-coated at 2000 rpm. The polyimide solution thus coated was cured by heating at 325° C. for 30 minutes, whereupon a polyimide film of 150 to 200 Å in thickness was formed. The polyimide film was then rubbed with a nylon cloth in one direction, thereby imparting an ability of orientating the liquid crystal thereto.

Two sheets of the polyimide film-coated glass substrate thus prepared were put upon each other to prepare a cell for evaluation. An epoxy adhesive was applied to each of the polyimide film-coated glass substrates by means of silk screen printing so that two substrates were bonded to each other and a gap of the cell was controlled. The epoxy adhesive was prepared by mixing an adhesive base (LCB-310B, a product of EHC) with a curing agent (LCB-301B, a product of EHC) and beads (GP-20, a product of EHC) for controlling cell gas in the proportion of 130:30:3. One of the glass substrates mentioned above was coated with the epoxy adhesive and laminated to other glass substrate in such a manner that the polyimide films faced each other. The epoxy adhesive thus coated was cured under such curing conditions that heating was conducted at 50° C. for 15 minutes, at 60° C. for 15 minutes, at 70° C. for 15 minutes, at 80° C. for 15 minutes, at 125° C. for 30 minutes and at 170° C. for 60 minutes.

The liquid crystal material was evaluated by using the thus prepared cell for evaluation having a gap of about 2 μm.

In the present invention, contrast was determined by placing the liquid crystal material between polarizers meeting at right angles, measuring an intencity of transmitted light in the light state and in the dark state by rotating the liquid crystal element, and calculating therefrom the ratio of I (light state)/I (dark state).

EXAMPLE 7

A liquid crystal element was prepared by repeating Example 6 except that the orientation directions of the orientation controlling films composed of polyimide were nearly parallel but in the opposite direction from each other.

The contrast of the thus obtaine liquid crystal element as measured was 18.

EXAMPLE 8

A liquid crystal element was prepared by repeating Example 6 except that one of the substrates was prepared by forming a rhombic deposited film composed of silicon oxide on the glass substrate provided with ITO transparent electrode film.

The rhombic deposited film was formed by heating $SiO_2$ to 400° C. and depositing it on the substrate from the vertical direction, the substrate being inclined at 30° from a horizontal plane.

In the liquid crystal element thus prepared, the orientation direction of the rhombic deposited film and that of the orientation controlling film were nearly parallel but in the opposite direction from each other.

The contrast of the thus obtained liquid crystal element as measured was 17.

EXAMPLE 9

A liquid crystal element was prepared by repeating Example 6 except that the cooling rate was changed to 0.1° C./min.

The contrast of the thus obtained liquid crystal element was 29.

EXAMPLE 10

A liquid crystal element was prepared by repeating Example 6 except that the liquid crystal composition obtained in Example 4 was used in place of the carboxylate compound and the cooling rate was changed to 0.1° C./min.

The contrast of the thus obtained liquid crystal element was 21.

EXAMPLE 11

A liquid crystal element was prepared by repeating Example 6 except that the cooling rate was changed to 10° C./min.

The contrast of the thus obtained liquid crystal element was 9. Because of rapid cooling rate employed, it was observed that the contrast was apt to be somewhat low.

EXAMPLE 12

Figure 6B:
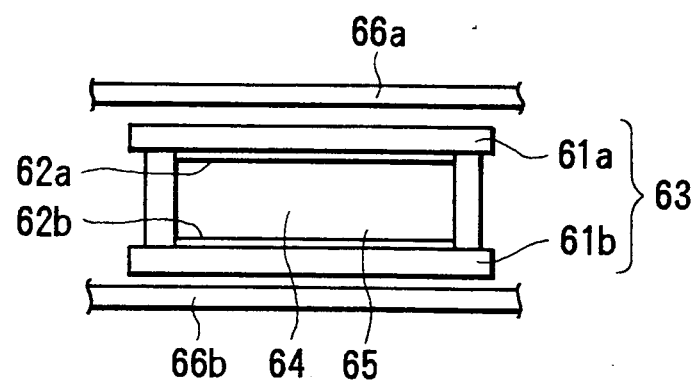

The carboxylate compound [5] of the formula [5] shown in Table 4 was molten and injected into a gap of a cell, said gap being kept under reduced pressure and said cell being composed of two substrates with ITO transparent electrodes, each substrate being provided with an orientation controlling film (thickness: 150 Å) composed of a polyimide (LX1400, a product of Hitachi Kasei Kogyo K.K.) on the inner surface thereof as shown in FIG. 6(B). The polyimide film was rubbed so that orientation directions were nearly parallel to each other and in the same direction. The cell thus filled with the liquid crystal material was heated to 120° C., kept at 120° C. for 5 minutes and cooled to 60° C. at a rate of 1° C./min to prepare a liquid crystal element.

Cell condition:
(a) External size: 2.5 cm long×2.2 cm width×1.5 mm thick
(b) Substrate: 0.7 mm thick, material: glass
(c) Distance between substrates: 2 $\mu$m
(d) Sidewall size: 1.8 mm long×2.2 mm width×1.5 $\mu$m thick The above-mentioned cell was prepared in the same manner as in Example 6.

A liquid crystal element was prepared by placing the above-mentioned liquid crystal cell filled with the liquid crystal material between two polarizing plates whose planes of polarization meet at right angles so that the darkest state is attained in the element.

The intencity of transmitted light was measured by applying a triangular wave of 30 $V_{p-p}$, whereupon the oscillowave shown in FIG. 7 was obtained by application of a frequency of 10 Hz, and the oscillowave shown in FIG. 8 was obtained by application of a frequency of 100 Hz.

As is clear from FIG. 7, this liquid crystal element attained the contrast of 34 between the time when 0 IV was applied and the time when +30 V (or −30 V) was applied by application of a triangular wave of 10 Hz.

As is clear from FIG. 8, this liquid crystal element attained the contrast of 15 between the time when −12 V was applied and the time when +12 V was applied by application a triangular wave of 100 Hz.

In the liquid crystal element of the invention in which the liquid crystal cell is placed between two polarizing plates whose planes of polarization meet at right angles so that the darkest state is attained in the element, the dark state can be attained by applying a voltage of 0 V using a low frequency, in particular.

The contrast mentioned above was determined by measuring the intencity of the transmitted light in the light state and in the dark state while changing a voltage applied to the liquid crystal element, and calculating therefrom the ratio of I (light state)/I (dark state).

Subsequently, a liquid crystal element was prepared by placing the above-mentioned liquid crystal cell filled with the liquid crystal material between two polarizing plates whose planes of polarization meet at right angles so that the lightest state is attained in the element.

The intencity of transmitted light was measured by applying a triangular wave of 30 $V_{p-p}$, whereupon the oscillowave shown in FIG. 9 was obtained by application of a frequency of 10 Hz, and the oscillowave shown in FIG. 10 was obtained by application of a frequency of 100 Hz.

From the above results, it was found that the liquid crystal element in which the liquid crystal cell is placed between two polarizing plates whose planes of polarization meet at right angles so that the lightest state is attained in the element could secure a favorable memory effect using a high frequency, in particular.

EXAMPLE 13

Synthesis of R-1'''-trifluoromethylheptyl 4-[4'-(1'',2'',3'',4''-tetrahydro-6''-n-octyloxy-2''-naphthoyloxy)benzoyloxy]benzoate

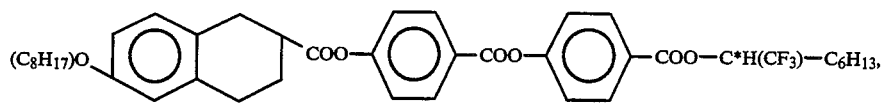

exemplified compound [7]

First step

To a mixture of 3.86 g (11.8 mmol) of 6-n-decyloxynaphthalene-2-carboxylic acid and 130 ml of 1,2-diethoxyethane was added in a nitrogen atmosphere at 120° C. with stirring 3.0 g (130 mg atom) of metallic sodium, and the mixture was then heated to a refluxing temperature.

To this mixture was added dropwise 10 g (114 mmol) of isoamyl alcohol over a period of 1 hour, and the mixture was allowed to undergo reaction for 11 hours under reflux. After cooling the reaction mixture to room temperature, the metallic sodium remaining in the mixture was decomposed by the addition of ethanol, and the reaction mixture was acidified with 20% hydrochloric acid.

After addition of 100 ml of water to the reaction mixture, an organic layer was separated therefrom, and the organic layer was washed with water.

The organic layer was concentrated under reduced pressure to obtain 4.25 g of a solid. The solid was recrystallized from toluene to obtain 2.95 g (8.89 mmol) of 1,2,3,4-tetrahydro-6-n-decyloxynaphthalene-2-carboxylic acid.

Second step

A mixture of 6.60 g (20.0 mmol) of 1,2,3,4-tetrahydro-6-n-decyloxynaphthalene-2-carboxylic acid, 100 ml of acetic acid, and 34.5 g of 47% hydrobromic acid was refluxed by heating at 130° C. for 11 hours. After the reaction, distilled water was added to the refluxed mixture, and the mixture was concentrated. The concentrate was washed with warmed hexane, and dried to obtain 3.90 g (20.0 mmol) of 1,2,3,4-tetrahydro-6-n-hydroxynaphthalene-2-caroxylic acid which was the desired compound.

Third step

A mixture of 0.48 g (2.5 mmol) of 1,2,3,4-tetrahydro-6-n-hydroxynaphthalene-2-carboxylic acid obtained in the second step, 0.77 g (4 mmol) of octyl bromide, 0.04 g (0.25 mmol) of sodium iodide, 0.33 g (5 mmol) of 85% potassium hydroxide-containing aqueous solution, 30 g of ethanol and 5 g of distilled water was refluxed for 8 hours by heating. To the mixture was added 2.5 ml of 10% potassium hydroxide, and the resultant mixture was further refluxed by heating for 8 hours.

The reaction mixture was cooled to room temperature, and poured into 100 ml of distilled water. The mixture was acidified with hydrochloric acid, and 0.32 g (1.05 mmol) of 1,2,3,4-tetrahydro-6-n-octyloxynaphthalene-2-carboxylic acid was obtained by adding toluene and recrystallizing.

Fourth step

To a mixture of 1.14 g (5 mmol) of 4-benzyloxybenzoic acid, 1.52 g (5 mmol) of R-1'-trifluoromethylheptyl 4-hydroxybenzoate, 0.06 g of 4-N,N-dimethylaminopyridine and 10 ml of methylene chloride was added dropwise 5 ml of a methylene chloride solution containing 1.03 g (5 mmol) of N,N-dicyclohexylcarbodiimide with stirring at room temperature over a period of 0.5 hour.

The reaction was carried out at room temperature for additional 7 hours.

The reaction mixture was filtered, and the filtrate was concentrated. Using column chromatography, 2.06 g (4.0 mmol) of R-1''-trifluoromethylhexyl 4-(4'-benzyloxybenzoyl) benzoate, a white solid, was separated from the concentrate.

Fifth step

Hydrogen gas was passed through a mixture of 2.06 g (4.01 mmol) R-1''-trifluoromethylheptyl 4-(4'-benzyloxybenzoyl) benzoate, obtained in the fourth step, 0.1 g of a catalyst containing of 5% palladium supported on carbon and 10 ml of tetrahydrofuran with stirring at room temperature and atmospheric pressure for 8 hours. The reaction mixture was filtered with Celite, a filter aid, and the filtrate obtained was concentrated to obtain 1.86 g (4.01 mmol) of R-1'''-trifluoromethylheptyl 4-(4'-hydroxybenzoyl) benzoate, a white solid.

Sixth step

To a mixture of 0.30 g (1.0 mmol) of 1,2,3,4-tetrahydro-6-n-octyloxynaphthalene-2-carboxylic acid obtained in the third step, 0.42 g (10 mmol) of R-1''-trifluoromethylhexyl 4-(4'-hydroxybenzoyl)benzoate obtained in the fifth step, 0.012 g (0.1 mmol) of 4-N,N-dimethylaminopyridine and 10 ml of methylene chloride was added dropwise 2 ml of a methylene chloride solution containing 0.2 g (1 mmol) of N, N-dicyclohexylcarbodiimide with stirring at room temperature over a period of 2.5 hours.

The reaction was carried out at room temperature for additional 4 hours.

The reaction mixture was filtered, and the filtrate was concentrated. Using column chromatography, 0.34 g of a semi-solid was obtained from the concentrate.

FD-mass spectrum of this semi-solid was measured to obtain an M/e value of 710.

Figure 11:
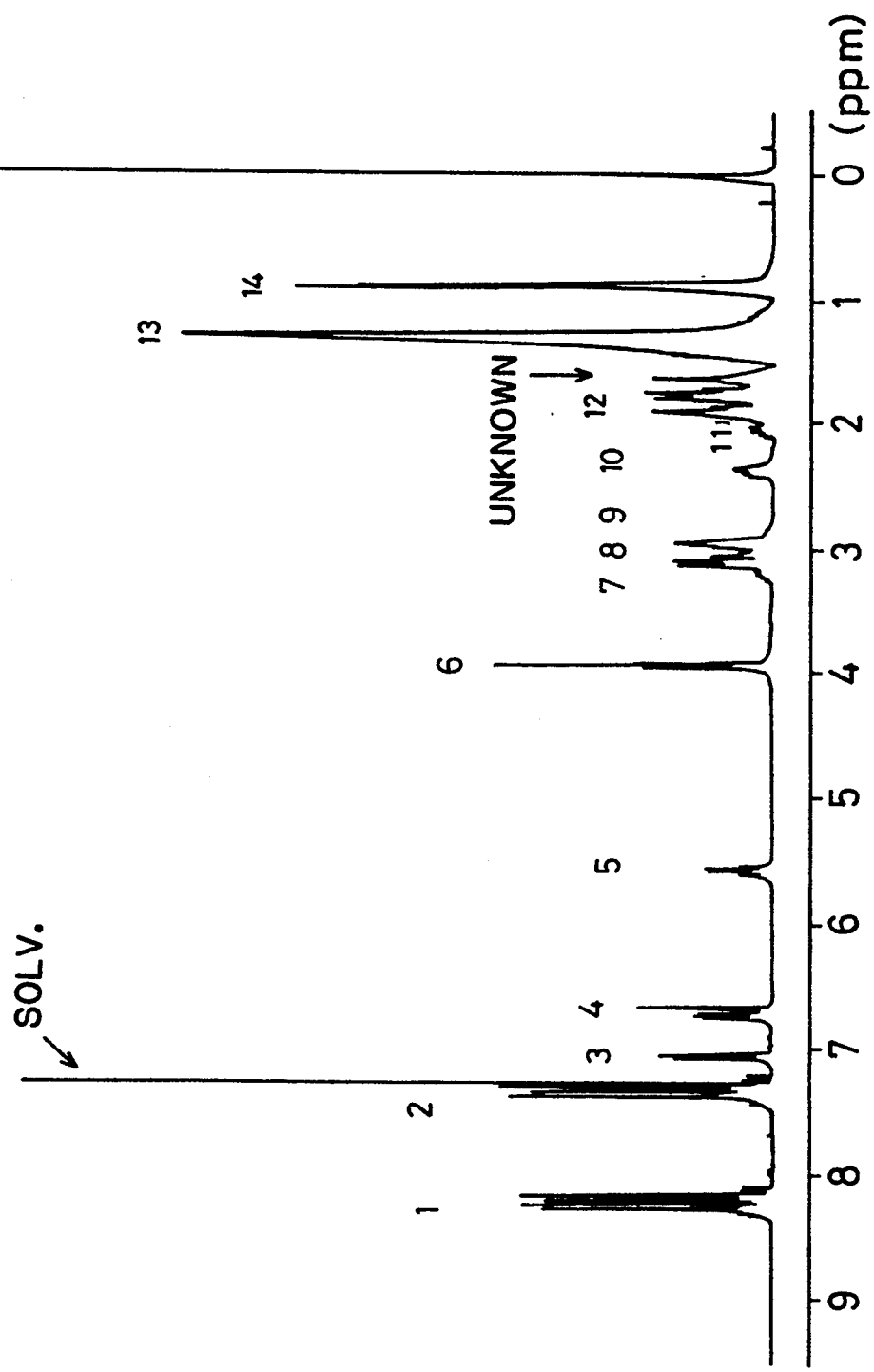
FIG. 11 is a chart showing $^1$H-NMR spectrum of R-1'''-trifluoromethylheptyl 4-[4'-(1'',2'',3'',4''-tetrahydro-6''-n-octyloxy-2''-naphthoyloxy) benzoyloxy]benzoate.

FIG. 11 shows a chart of 1H-NMR spectrum of this compound.

From the results of the analyses, the compound was identified to be R-1'''-trifluoromethylheptyl 4-[4'(1'',2'',3'',4''-tetrahydro-6''-n-octyloxy-2''-naphthoyloxy) benzoyloxy]benzoate of the following formula which was the desired compound.

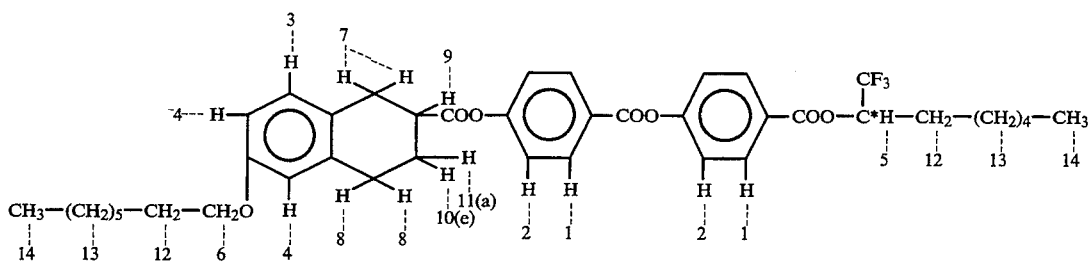

In the above formula, the symbol (a) means axial conformation and the symbol (e) means equatorial conformation.

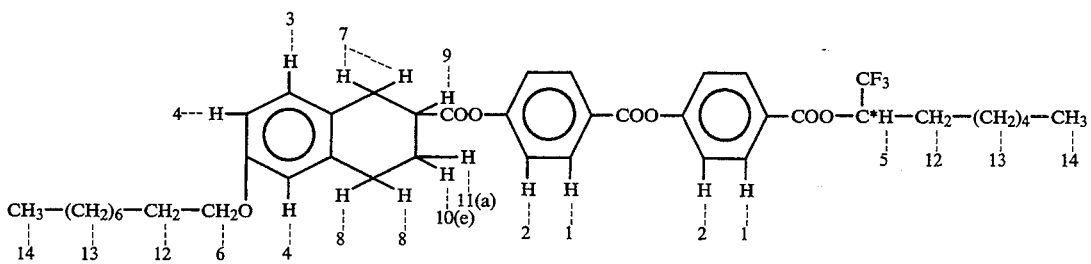

Notes: (a) and (e) being as defined in Example 13.

EXAMPLE 14

Synthesis of R-1'''-trifluoromethylheptyl 4-[4'-(1'',2'',3'',4''-tetrahydro-6''-n-nonyloxy-2''-naphthoyloxy) benzoyloxy]benzoate

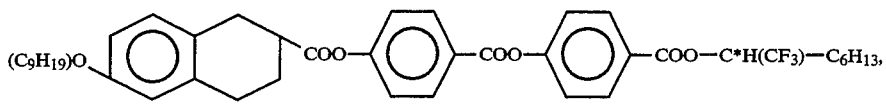

exemplified compound [6]

A colorless semi-solid was obtained in an amount of 0.49 g by repeating Example 13 except that nonylbromide was used in place of octyl bromide used in the third step in Example 13.

FD-mass spectrum of this semi-solid was measured to obtain an M/e value of 724.

Figure 12:
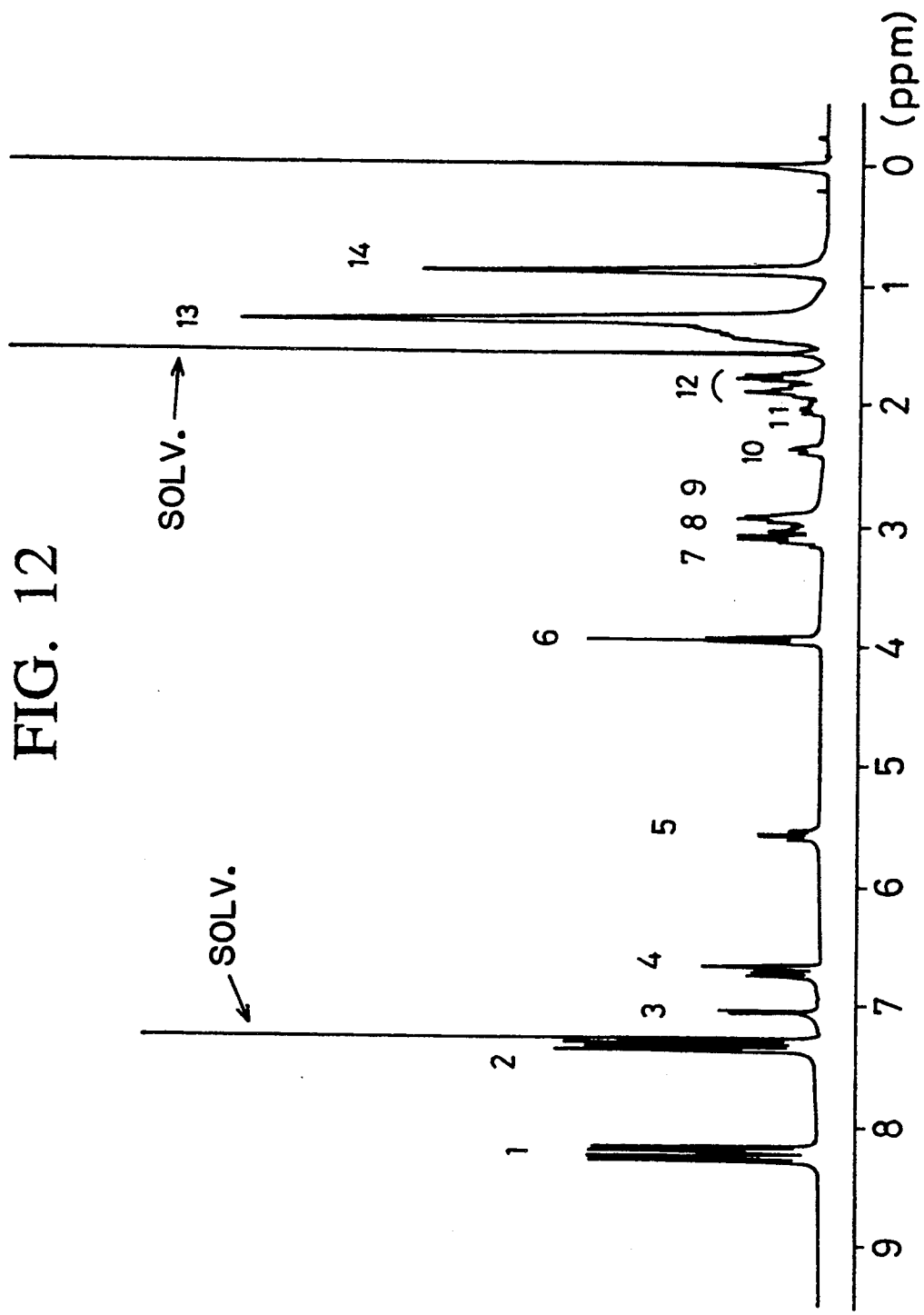
FIG. 12 is a chart showing $^1$H-NMR spectrum of R-1'''-trifluoromethylheptyl 4-[4'-(1'',2'',3'',4''-tetrahydro-6''-n-nonyloxy-2''-naphthoyloxy) benzoyloxy]benzoate.

FIG. 12 shows a chart of 1H-NMR spectrum of this compound.

From the results of the analyses, the compound was identified to be R-1'''-trifluoromethylheptyl 4-[4'-(1'',2'',3'',4''-tetrahydro-6''-n-nonyloxy-2''-naphthoyloxy) benzoyloxy]benzoate of the following formula which was the desired compound.

EXAMPLE 15

Synthesis of R-1'''-trifluoromethylheptyl 4-[4'-(1'',2'',3'',4''-tetrahydro-6''-n-undecyloxy-2''-naphthoyloxy) benzoyloxy]benzoate

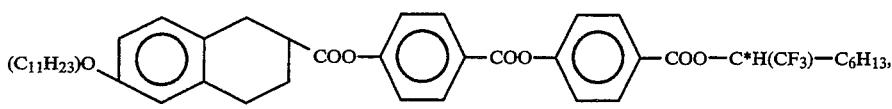

exemplified compound [4]

A colorless semi-solid in an amount of 0.44 g was obtained by repeating Example 13 except that undecyl bromide was used in place of octyl bromide used in the third step in Example 13.

FD-mass spectrum of this semi-solid was measured to obtain an M/e value of 752.

Figure 13:
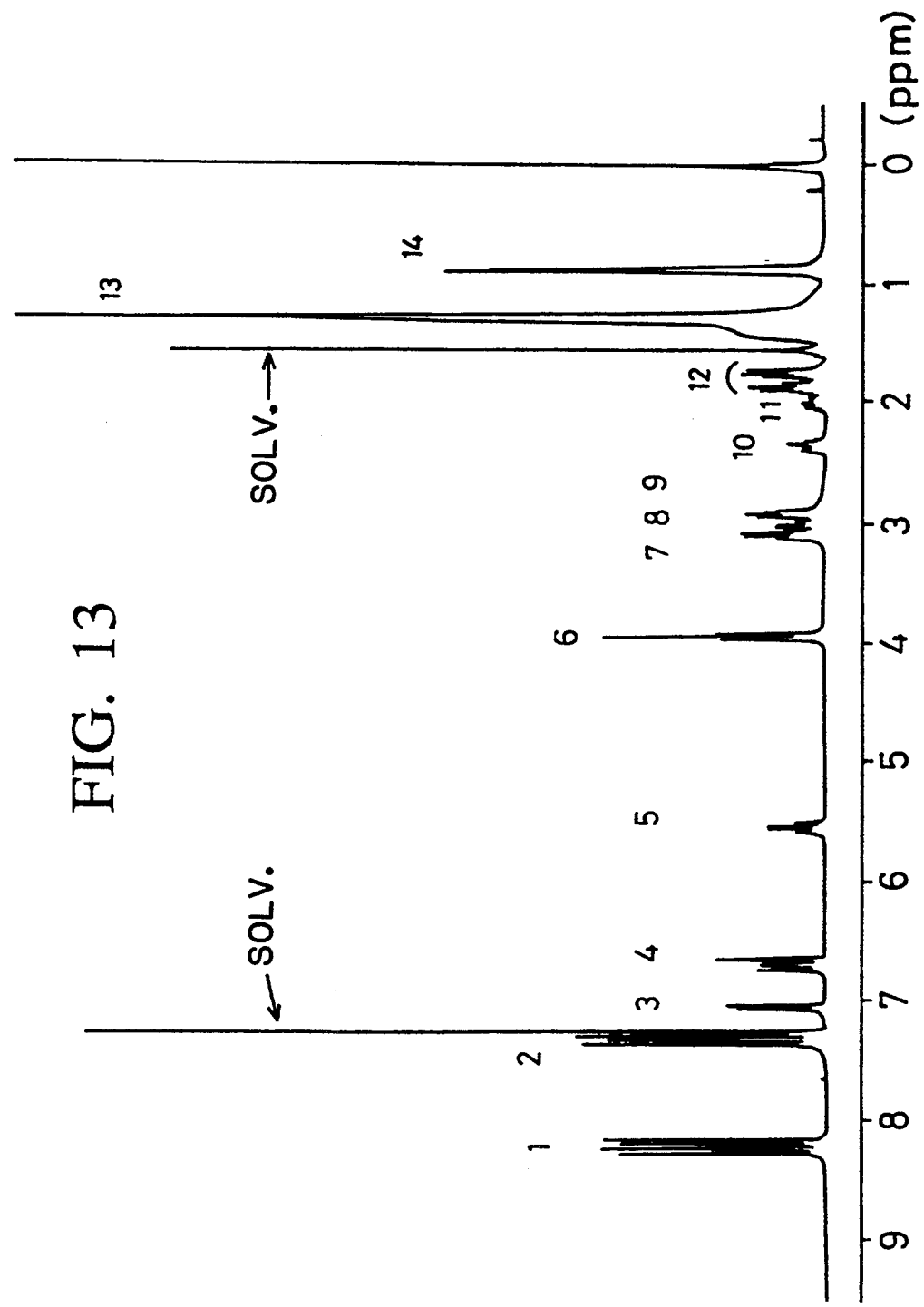
FIG. 13 is a chart showing $^1$H-NMR spectrum of R-1'''-trifluoromethylheptyl 4-[4'-(1'',2'',3'',4''-tetrahydro-6''-n-undecyloxy-2''-naphthoyloxy) benzoyloxy]benzoate.

FIG. 13 shows a chart of 1H-NMR spectrum of this compound.

From the results of the analyses, the compound was identified to be R-1'''-trifluoromethylheptyl 4-[4'-(1'',2'',3'',4''-tetrahydro-6''-n-undecyloxy-2''-naphthoyloxy) benzoyloxy]benzoate of the following formula which was the desired compound.

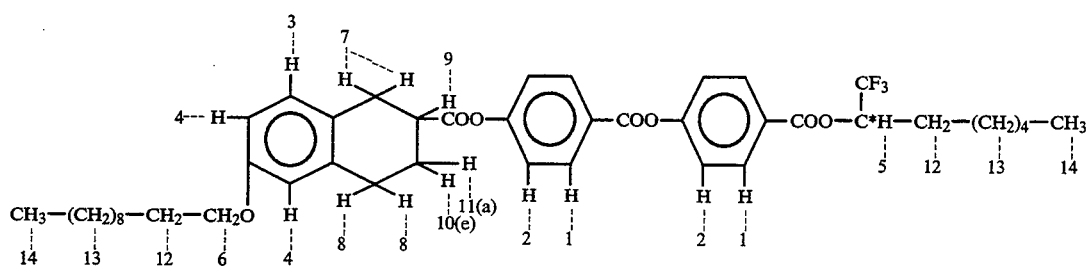

Notes: (a) and (e) being as defined in Example 13.

EXAMPLE 16

Synthesis of R-1'''-trifluoromethylheptyl 4-[4'-(1'',2'',3'',4''-tetrahydro-6''-n-dodecyloxy-2''-naphthoyloxy) benzoyloxy]benzoate

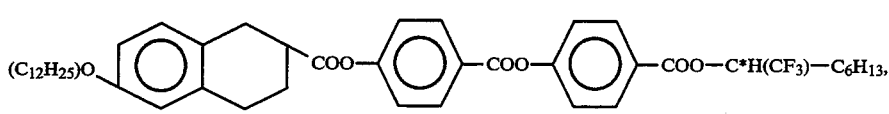

exemplified compound [3]

A colorless semi-solid in an amount of 1.1 g was obtained by repeating Example 13 except that dodecyl bromide was used in place of octyl bromide used in the third step in Example 13.

FD-mass spectrum of this semi-solid was measured to obtain an M/e value of 766.

Figure 14:
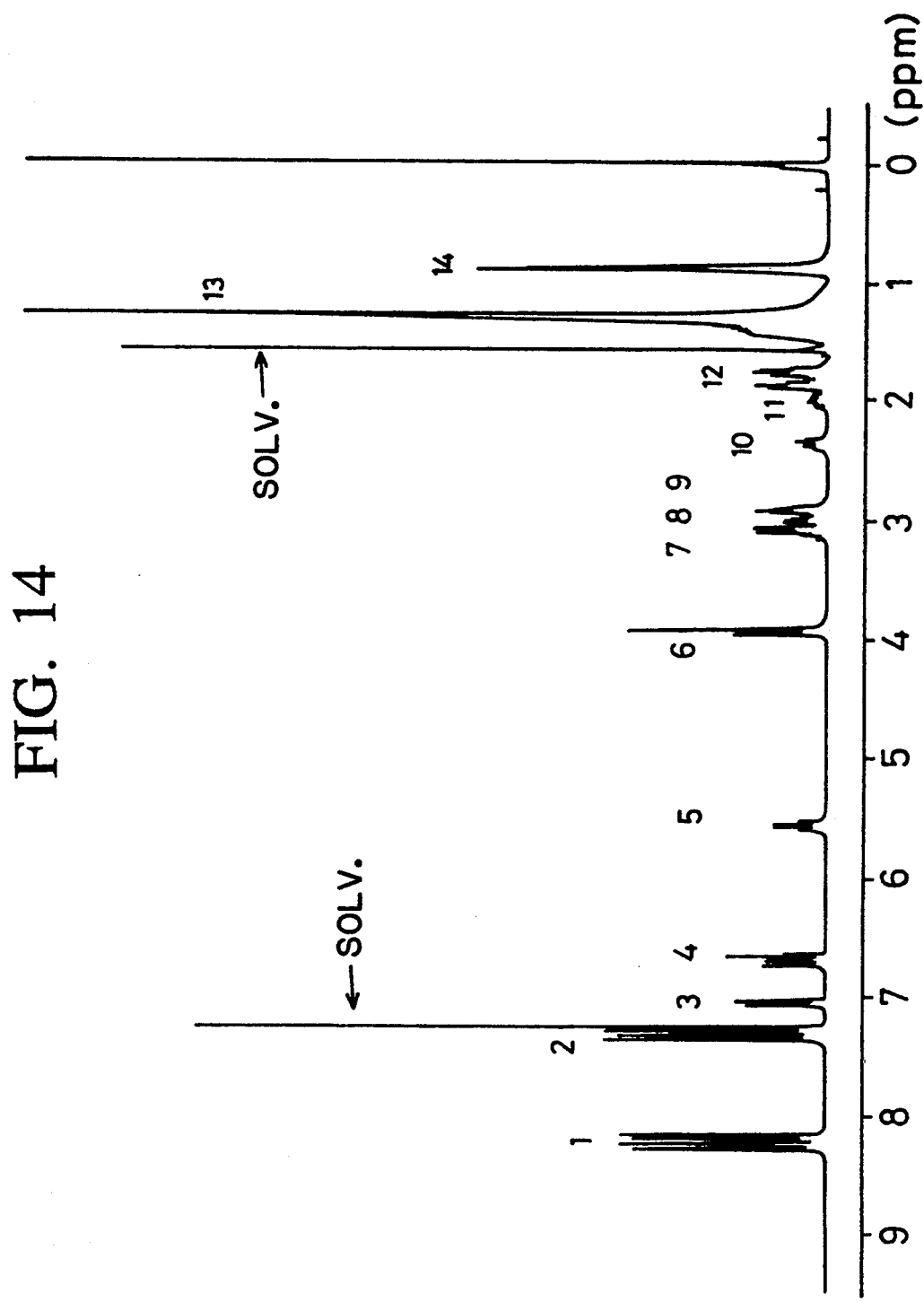
FIG. 14 is a chart showing $^1$H-NMR spectrum of R-1'''-trifluoromethylheptyl 4-[4'-(1'',2'',3'',4''-tetrahydro-6''-n-dodecyloxy 2''-naphthoyloxy) benzoyloxy]benzoate.

FIG. 14 shows a chart of 1H-NMR spectrum of this compound.

This compound was identified to be R-1'''-trifluoromethylheptyl 4-[4'-(1'',2'',3'',4''-tetrahydro-6''-n-dodecyloxy-2''-naphthoyloxy)benzoyloxy]benzoate of the following formula which was the desired compound.

First step

The first step of Example 13 was repeated to obtain 2.95 g (8.89 mmol) of 1,2,3,4-tetrahydro-6-n-decyloxynaphthalene-2-carboxylic acid.

Second step

To a mixture of 1.66 g (5 mmol) of 1,2,3,4-tetrahydro-6-n-decyloxynaphthalene-2-carboxylic acid obtained in the first step, 1.14 g (5 mmol) of benzyl 4-hydroxybenzoate, 0.12 g (1 mmol) of 4-N,N-dimethylaminopyridine and 20 ml of methylene chloride was added dropwise 10 ml of a methylene chloride solution containing 1.03 g (5 mmol) of N,N'-dicyclohexylcarbodiimide at room temperature with stirring over a period of 1 hour.

The reaction was carried out at room temperature for additional 10 hours.

The reaction mixture was filtered, and the filtrate was concentrated. Using column chromatography, 2.32 g

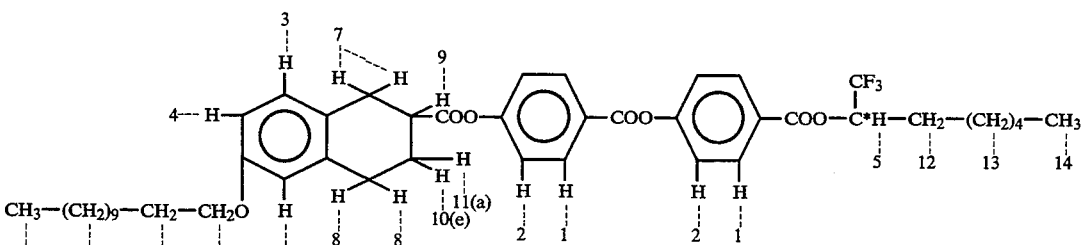

Notes: (a) and (e) being as defined in Example 13.

EXAMPLE 17

Synthesis of S-2'''-methylbutyl 4-[4'-(1'',2'',3'',4''-tetrahydro-6''-n-decyloxy-2''-naphthoyloxy) benzoyloxy]benzoate

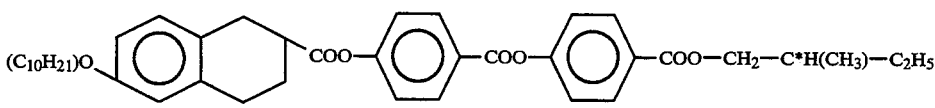

exemplified compound [35]

(4.28 mmol) of benzyl 4-(1',2',3',4'-tetrahydro-6'-n-decyloxy-2'-naphthoyloxy)benzoate, a white solid, was separated from the concentrate.

Third step

Hydrogen gas was passed through a mixture of 2.17 g (4 mmol) of benzyl 4-(1',2',3',4'-tetrahydro-6'-n-decyloxy-2'-naphthoyloxy)benzoate obtained in the second step, 1 g of a catalyst containing 5% palladium supported on carbon and 30 ml of tetrahydrofuran with stirring at room temperature and atmospheric pressure for 8 hours. The reaction mixture was filtered with Celite, a filter aid, and the filtrate obtained was concentrated to obtain 1.59 g (3.52 mmol) of 4-(1',2',3',4'-tetrahydro-6'-n-decyloxy-2'-naphthoyloxy) benzoic acid, a

EXAMPLE 18

Synthesis of R-1'''-methylheptyl 4-[4'-(1'',2'',3'',4''-tetrahydro-6''-n-decyloxy-2''-naphthoyloxy)benzoyloxy]benzoate

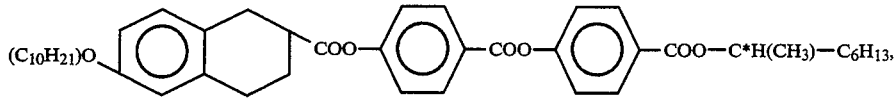

white solid.

Fourth step

To a mixture of 0.45 g (1 mmol) of 4-(1',2',3',4'-tetrahydro-6'-n-decyloxy-2'-naphthoyloxy)benzoic acid obtained in the third step, 0.30 g (1 mmol) of S-2'-methylbutyl 4-hydroxybenzoate, 0.012 g (0.1 mmol) of 4-N,N-dimethylaminopyridine and 10 ml of methylene chloride was added dropwise 2 ml of a methylene chloride solution containing 0.21 g (1 mmol) of N,N'-dicyclohexylcarbodiimide with stirring at room temperature over a period of one hour. The reaction was carried out at room temperature for additional 8 hours. The reaction mixture was filtered, and the filtrate was concentrated. Using column chromatography, 0.52 g of a colorless semi-solid was separated from the concentrate.

FD-mass spectrum of this semi-solid was measured to obtain an M/e value of 642.

Figure 15:
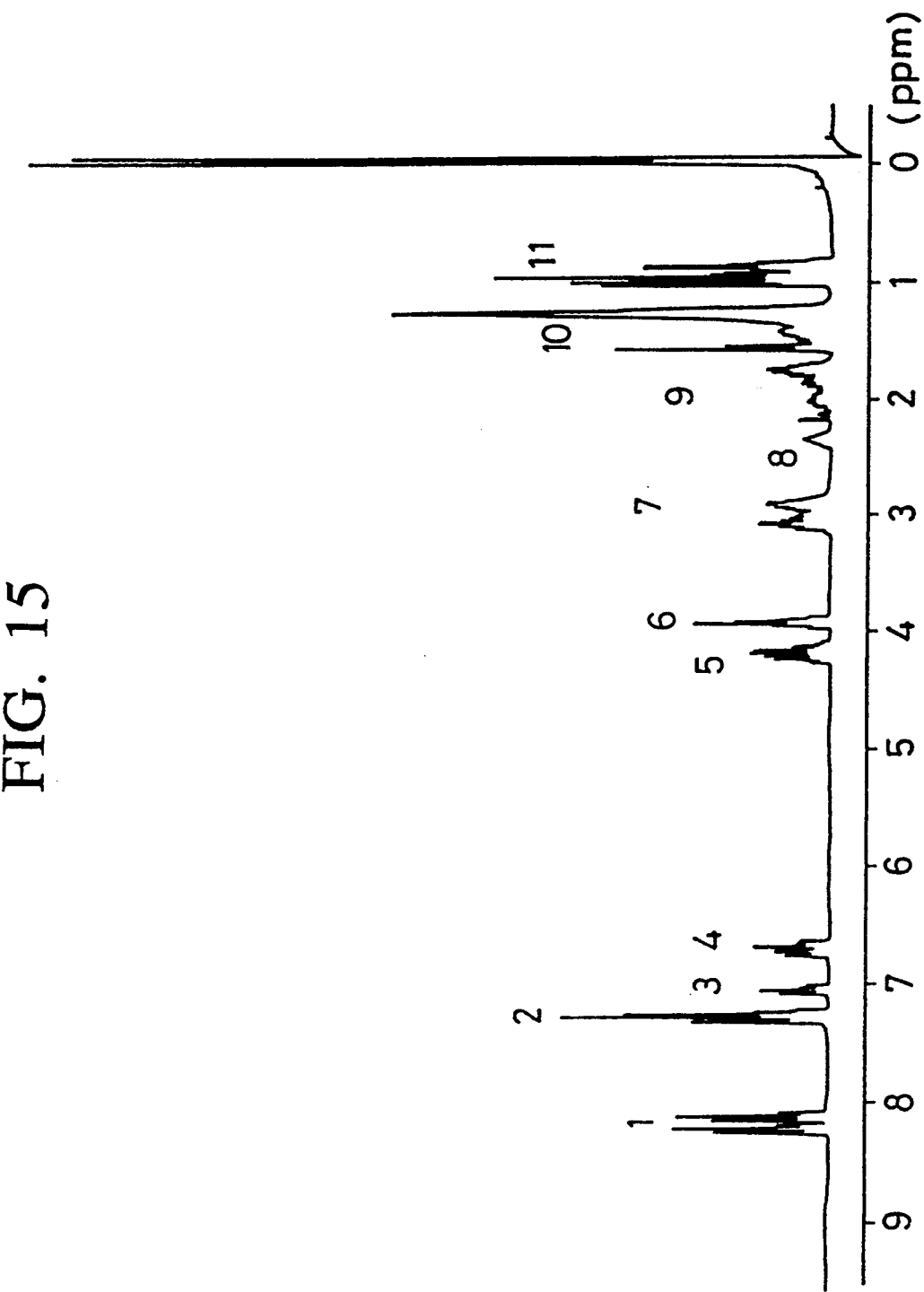
FIG. 15 is a chart showing $^1$H-NMR spectrum of S-2'''-methylbutyl 4-[4'-(1'',2'',3'',4''-tetrahydro-6''-n-decyloxy-2''-naphthoyloxy)benzoyloxy]benzoate.

FIG. 15 shows a chart of $^1$H-NMR spectrum of this compound.

From the results of the analyses, the compound was identified to be S-2'''-methylbutyl 4-[4'-(1'',2'',3'',4''-tetrahydro-6''-n-decyloxy-2''-naphthoyloxy)benzoyloxy]benzoate which was the desired compound.

exemplified compound [33]

Example 17 was repeated except that R-1'-methylbutyl 4-hydroxybenzoate was used in place of S-2'-methylbutyl 4-hydroxybenzoate used in the fourth step in Example 17 to obtain a colorless semisolid in an amount of 0.29 g.

FD-mass spectrum of this compound (semi-solid) was measured to obtain an M/e value of 684.

Figure 16:
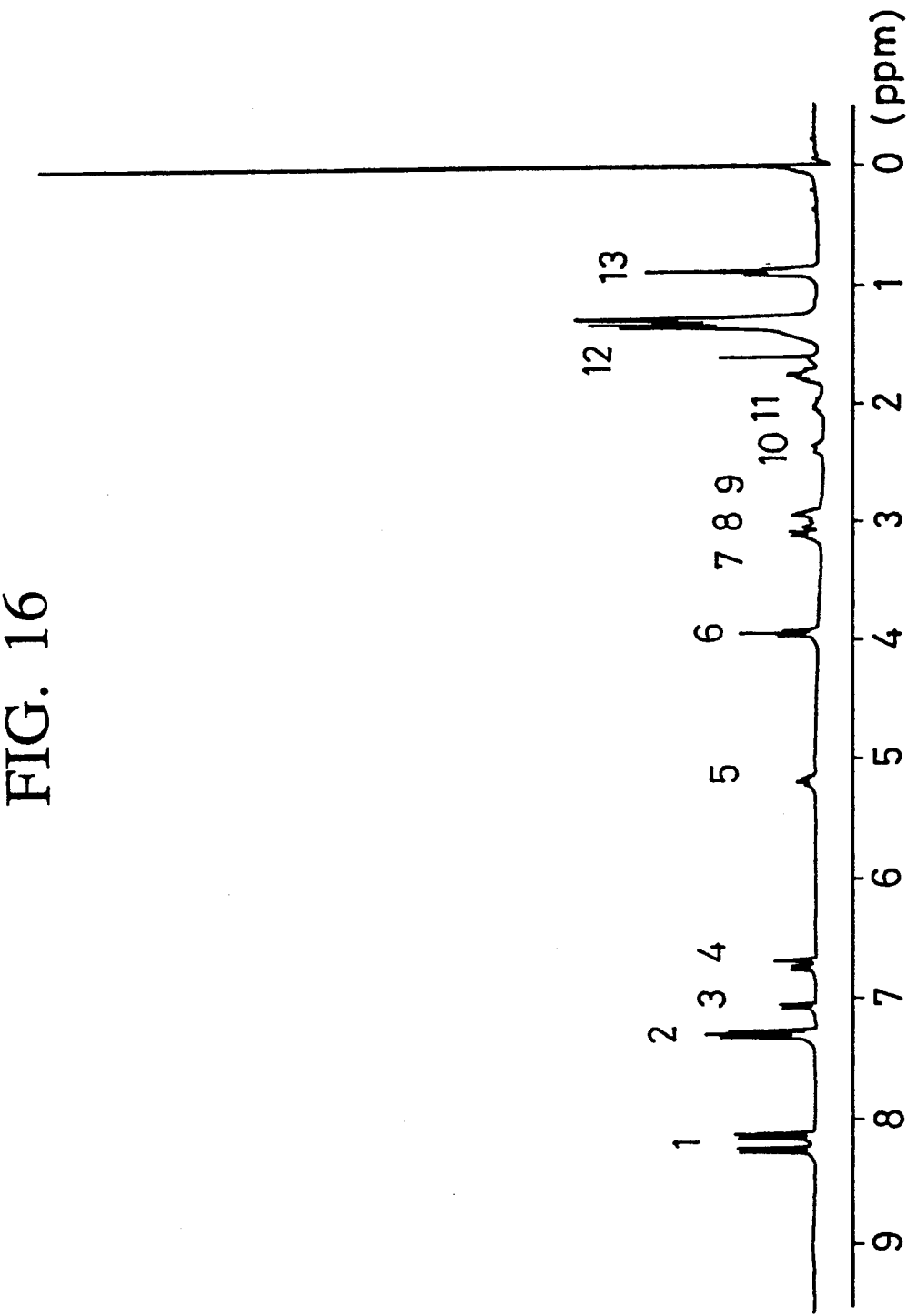
FIG. 16 is a chart showing $^1$H-NMR spectrum of R-1'''-methylheptyl 4-[4'-(1'',2'',3'',4''-tetrahydro-6''-n-decyloxy-2''-naphthoyloxy)benzoyloxy]benzoate.

FIG. 16 shows a chart of $^1$H-NMR spectrum of this compound.

From the results of the analyses, the compound was identified to be R-1'''-methylheptyl 4-[4'-(1'',2'',3'',4''-tetrahydro-6''-n-decyloxy-2''-naphthoyloxy)benzoyloxy]benzoate which was the desired compound.

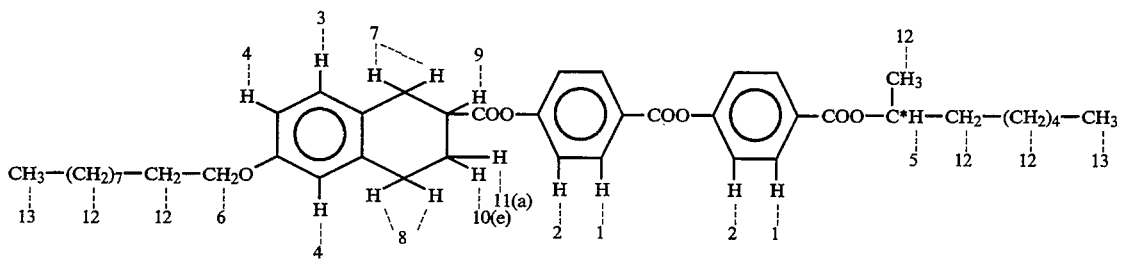

EXAMPLE 19

Synthesis of R-1'''-ethylheptyl 4-[4'-(1'',2'',3'',4''-tetrahydro-6''-n-decyloxy-2''-naphthoyloxy)benzoyloxy]benzoate

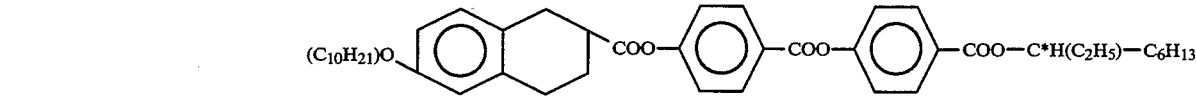

compound.

From the results of the analyses, the compound was identified to be S-2'''-methylbutyl 4-[4'-(1'',2'',3'',4''-tetrahydro-6''-n-decyloxy-2''-naphthoyloxy)benzoyloxy]benzoate which was the desired compound.

exemplified compound [34]

Example 17 was repeated except that R-1'-ethylheptyl 4-hydroxybenzoate was used in place of S-2'-methylbutyl 4-hydroxybenzoate used in the fourth step in Example 17 to obtain a colorless semisolid in an amount of 0.34 g.

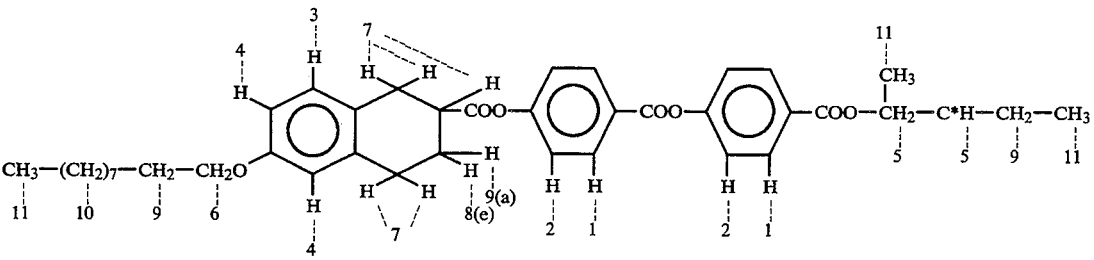

FD-mass spectrum of this semi-solid was measured to obtain an M/e value of 698.

Figure 17:
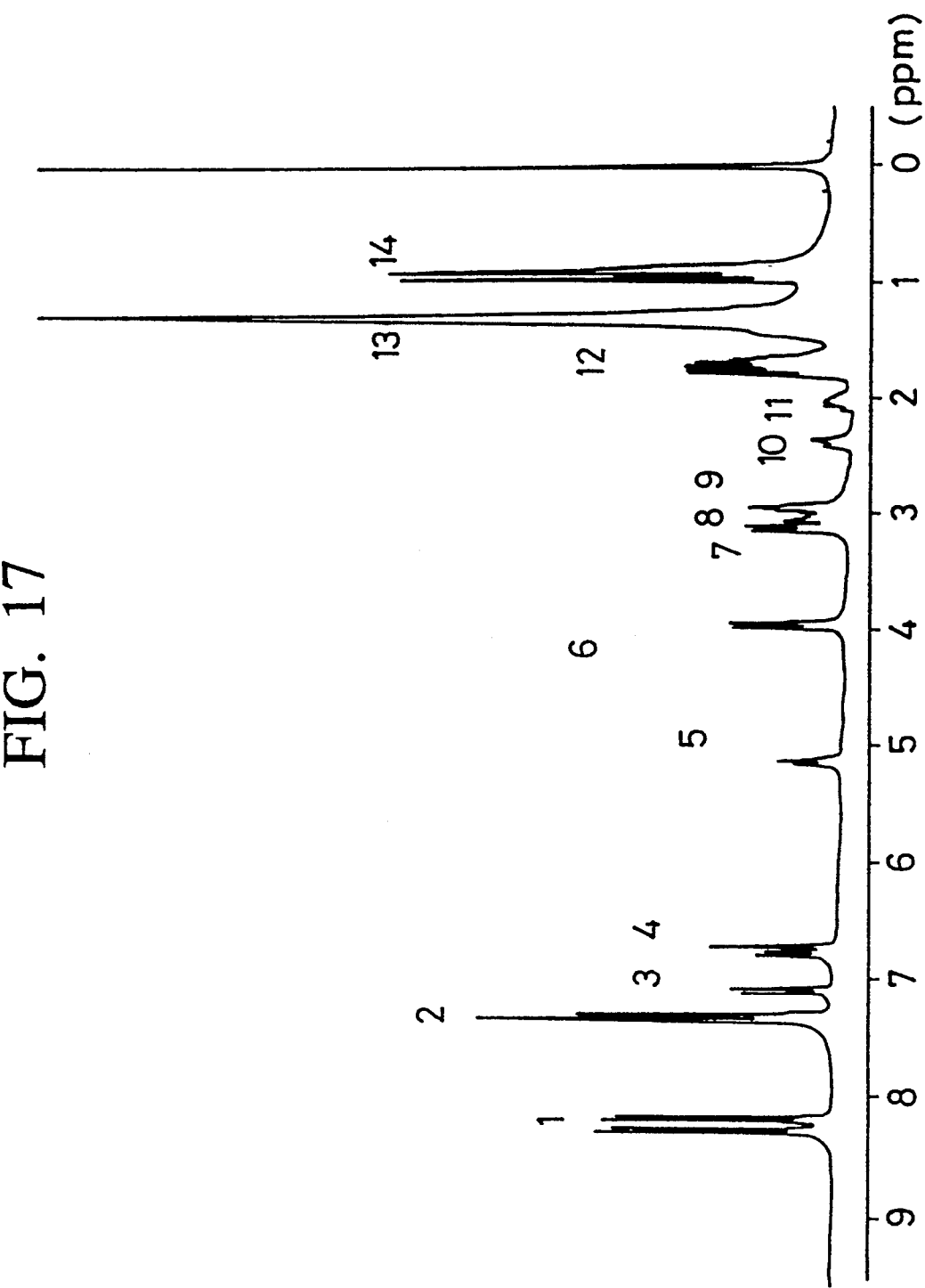
FIG. 17 is a chart showing $^1$H-NMR spectrum of R-1'''-ethylheptyl 4-[4'-(1'',2'',3'',4''-tetrahydro-6''-n-decyloxy-2''-naphthoyloxy)benzoyloxy]benzoate.

FIG. 17 shows a chart of $^1$H-NMR spectrum of this compound.

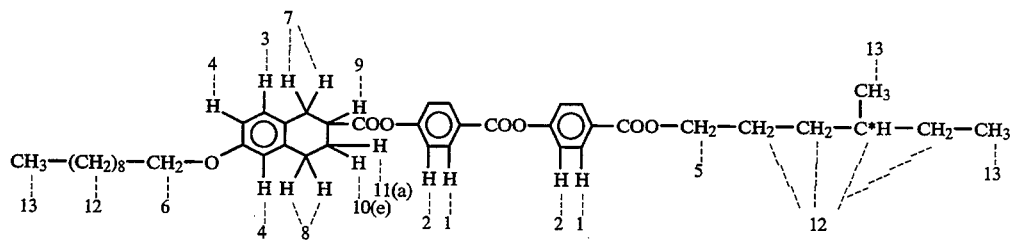

From the results of the analyses, the compound was identified to be R-1'''-ethylheptyl 4-[4'-(1'',2'',3'',4''-tetrahydro-6''-n-decyloxy-2''-naphthoyloxy)benzoyloxy]benzoate which was the desired compound.

EXAMPLE 20

Synthesis of S-4'''-methylhexyl 4-[4'-(1'',2'',3'',4''-tetrahydro-6''-n-decyloxy-2''-naphthoyloxy)benzoyloxy]benzoate

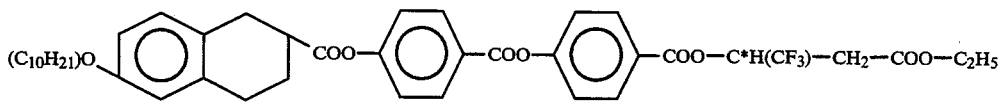

exemplified compound [36]

Example 17 was repeated except that S-4'-methylhexyl 4-hydroxybenzoate was used in place of S-2'-methylbutyl 4-hydroxybenzoate used in the fourth step in Example 17 to obtain a colorless semisolid in an amount of 0.48 g.

FD-mass spectrum of this semi-solid was measured to obtain an M/e value of 684.

Figure 18:
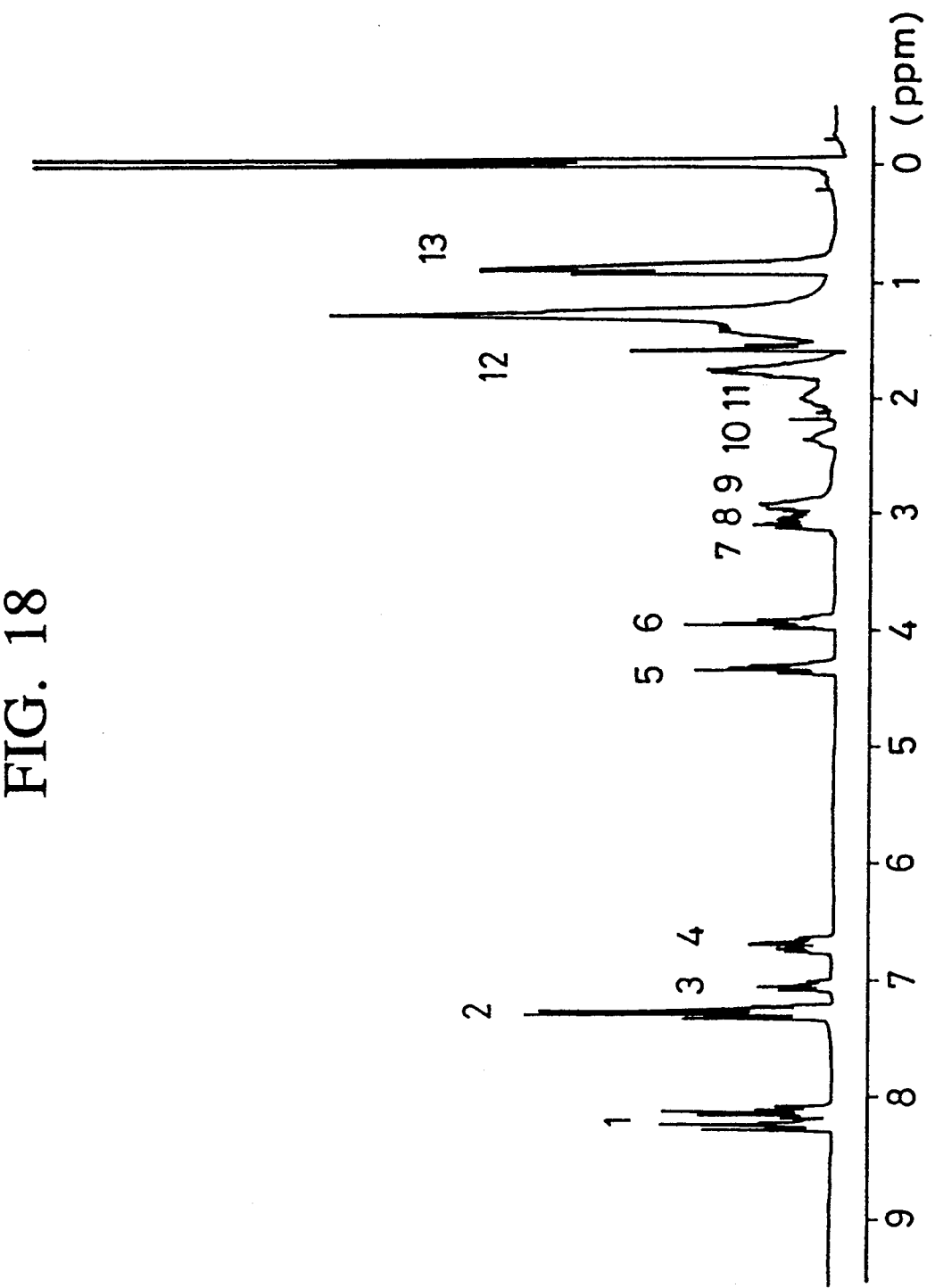
FIG. 18 is a chart showing $^1$H-NMR spectrum of S-4'''-methylhexyl 4-[4'-(1'',2'',3'',4''-tetrahydro-6''-n-decyloxy-2''-naphthoyloxy)benzoyloxy]benzoate.

FIG. 18 shows a chart of 1H-NMR spectrum of this compound.

From the results of the analyses, the compound was identified to be S-4'''-methylhexyl 4-[4'-(1'',2'',3'',4''-tetrahydro-6''-n-decyloxy-2''-naphthoyloxy)benzoyloxy]benzoate which was the desired compound.

EXAMPLE 21

Synthesis of R-2'''-ethyloxycarbonyl-1'''-trifluoromethylethyl 4-[4'-(1'',2'',3'',4''-tetrahydro-6''-n-decyloxy-2''-naphthoyloxy)benzoyloxy]benzoate

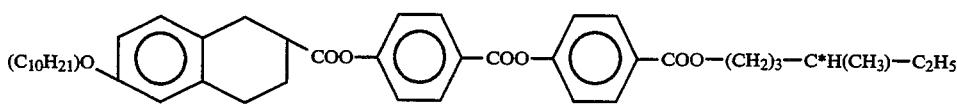

exemplified compound [37]

Example 17 was repeated except that R-1'-trifluoroethyl-oxycarbonylethyl 4-hydroxybenzoate was used in place of S-2'-methylbutyl 4-hydroxybenzoate used in the fourth step in Example 17 to obtain a colorless semisolid in an amount of 0.51 g.

FD-mass spectrum of this semi-solid was measured to obtain an M/e value of 740.

Figure 19:
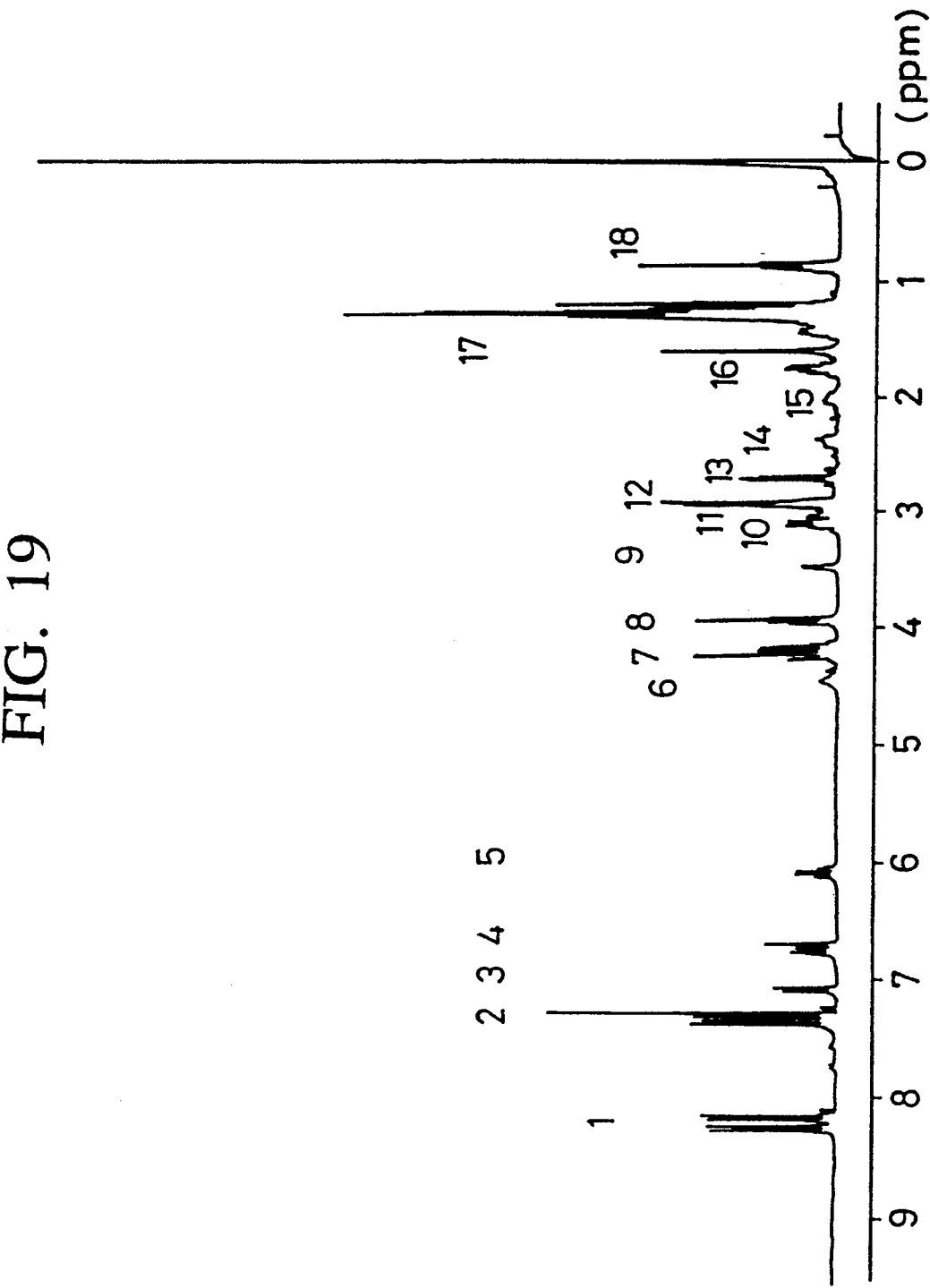
FIG. 19 is a chart showing $^1$H-NMR spectrum of R-2'''-ethyloxycarbonyl-1'''-trifluoromethylethyl 4-[4(1'',2'',3'',4''-tetrahydro-6''-n-decyloxy-2''-naphthoyloxy)benzoyloxy]benzoate.

FIG. 19 shows a chart of $^1$H-NMR spectrum of this compound.

From the results of the analyses, the compound was identified to be R-2'''-ethyloxycarbonyl-1'''-trifluoromethylethyl 4-[4'-(1'',2'',3'',4''-tetrahydro-6''-n-decyloxy-2''-naphthoyloxy)benzoyloxy]benzoate which was the desired compound.

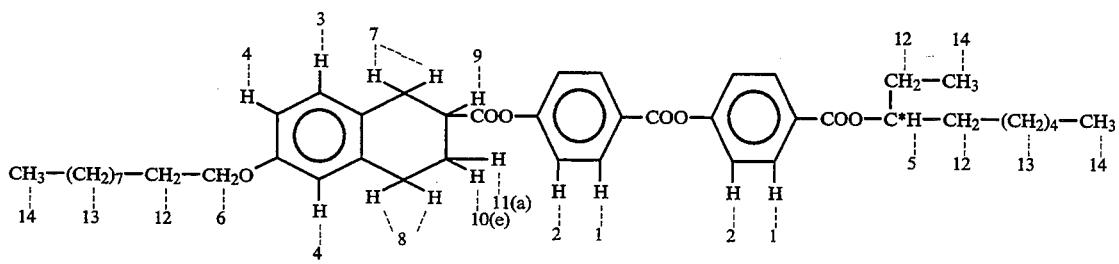

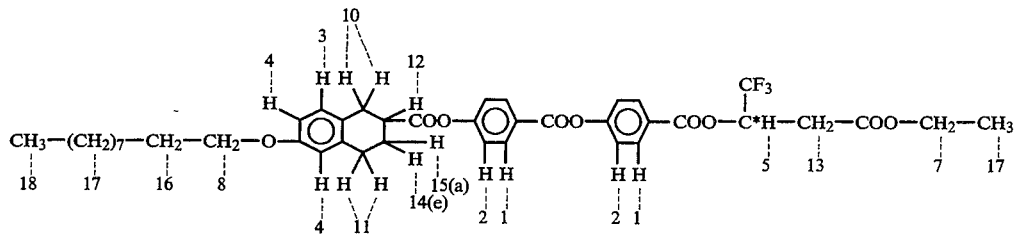

EXAMPLE 22

Synthesis of
R-2''-ethyloxycarbonyl-1''-trifluoromethylethyl
4-(1',2',3',4'-tetrahydro-6'-n-decyloxy-2'-naphthoyloxy)benzoate

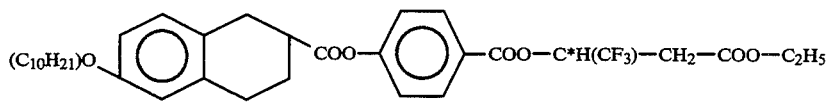

exemplified compound [38]

Example 17 was repeated except that R-2'-ethyloxycarbonyl-1'-trifluoromethylethanol was used in place of S-2'-methylbutyl 4-hydroxybenzoate used in the fourth step in Example 17 to obtain a colorless semi-solid was in an amount of 0.42 g.

FD-mass spectrum of this semi-solid was measured to obtain an M/e value of 620.

Figure 20:
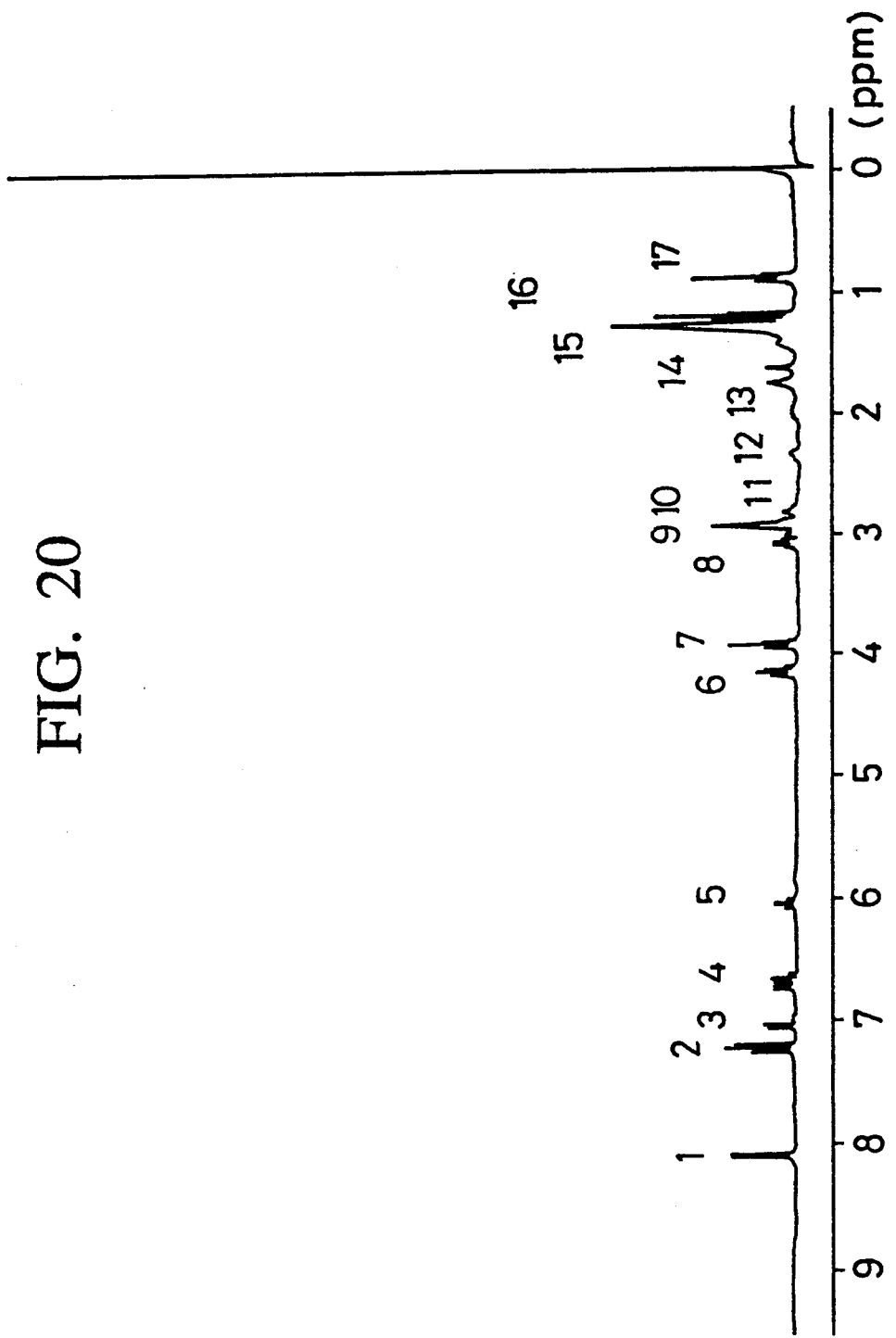
FIG. 20 is a chart showing $^1$H-NMR spectrum of R-2''-ethyloxycarbonyl-1''-trifluoromethylethyl 4-(1',2',3',4'-tetrahydro-6'-n-decyloxy-2'-naphthoyloxy) benzoate.

FIG. 20 shows a chart of $^1$H-NMR spectrum of the semi-solid.

From the results of the analyses, the compound was identified to be R-2''-ethyloxycarbonyl-1''-trifluoromethylethyl 4-(1',2',3',4'-tetrahydro-6'-n-decyloxy-2''-naphthoyloxy)benzoate which was the desired compound.

First step

The first step of Example 13 was repeated to obtain 2.95 g (8.89 mmol) of 1,2,3,4-tetrahydro-6-n-decyloxynaphthalene-2-carboxylic acid.

Second step

A mixture of 2.20 g (10 mmol)-of trans-4-(4'-hydroxyphenyl)cyclohexanecarboxlic acid, 6.84 g (40 mmol) of benzyl bromide, 5.53 g (40 mmol) of potassium carbonate and 50 ml of dimethylformamide was heated at 120° C. with stirring for 4 hours.

The mixture was stirred at room temperature for additional 4 hours.

The reaction mixture solution was poured into 450 ml of water to precipitate a viscous material. The viscous material was separated from the solution, and washed with hexane to obtain 3.54 g (6.4 mmol) of benzyl trans-4-(4'-benzyloxy-phenyl) cyclohexanecarboxylate, a white solid.

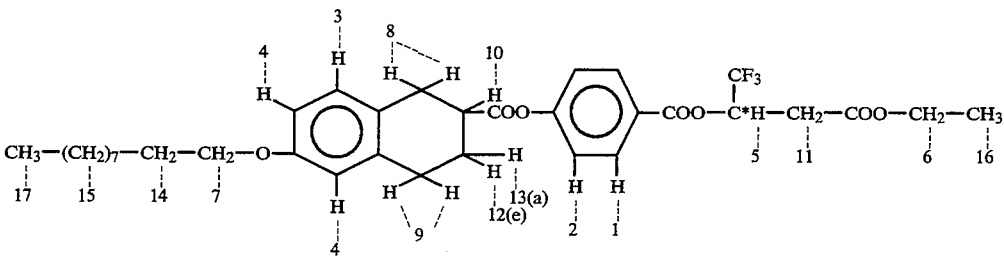

EXAMPLE 23

Synthesis of R-1'''-trifluoromethylheptyl
trans-4-[4'-1'',2'',3'',4''-tetrahydro-6''-n-decyloxy-2''-naphthoyloxy) phenyl]cyclohexanecarboxylate

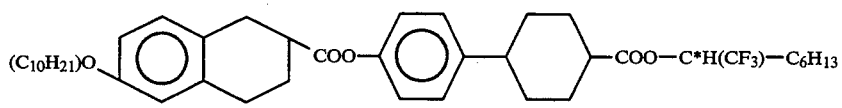

exemplified compound [21]

Third step

There was heated at 120° C. with stirring for 9 hours a mixture of 2.54 g (6.4 mmol) of benzyl trans-4-(4'-benzyloxyphenyl)cyclohexanecarboxylate obtained in the second step, 0.86 g (13 mmol) of 85% potassium hydroxide-containing aqueous solution, a solvent mixture of 30 ml of ethanol and 30 ml of water. The reaction mixture was then poured into 200 ml of water, and the reaction system was acidified by adding dropwise hydrochloric acid thereto to precipitate a white solid. The resultant mixture was filtered to obtain 1.68 g (5.4 mmol) of trans-4-(4'-benzyloxyphenyl)cyclohexane-carboxylic acid, a white solid.

Fourth step

To a mixture of 1.68 g (5.4 mmol) of trans-4-(4'-benzyloxyphenyl)cyclohexanecarboxylic acid obtained in the third step, 0.994 g (5.4 mmol) of R-1-trifluoromethylheptyl alcohol, 0.12 g (1 mmol) of 4-N,N-dimethylaminopyridine and 20 ml of methylene chloride was added dropwise with stirring for 1 hour a methylene chloride solution prepared by dissolving 1.11 g (5.4 mmol) of N,N'-dicyclohexanecarbodiimide in 10.8 ml of methylene chloride.

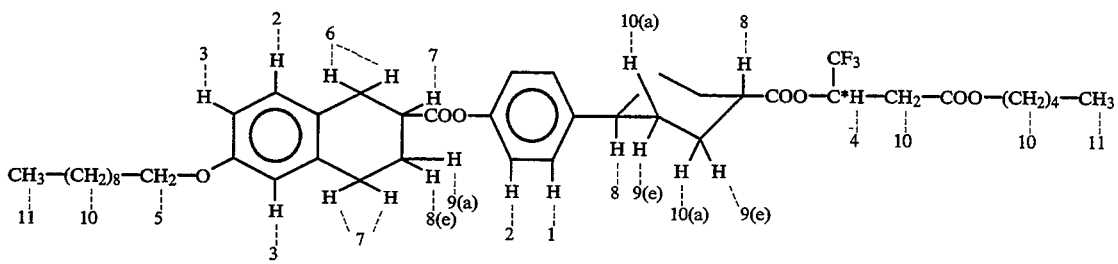

The reaction was further carried out at room temperature for additional 10 hours.

The reaction mixture was then filtered, and the filtrate was concentrated. Using column chromatography, 2.27 g (4.76 mmol) of R-1'-trifluoromethylheptyl trans-4-(4'-benzyloxy-phenyl)cyclohexanecarboxylate as a white solid was separated from the concentrate.

Fifth step

Hydrogen was passed through a mixture of 2.27 g (4.76 mmol) of R-1'-trifluoromethylheptyl trans-4-(4'-benzyloxyphenyl)cyclohexanecarboxylate obtained in the fourth step, 1.6 g of a catalyst containing 5% palladium supported on carbon and 50 ml of tetrahydrofuran at room temperature with stirring for 6.5 hours.

The reaction mixture was then filtered with Celite, a filter aid, and the filtrate was concentrated. Using column chromatography, 1.90 g (4.76 mmol) of R-1''-trifluoromethyl-heptyl trans-4-(4'-hydroxyphenyl) cyclohexanecarboxylate, a colorless viscous material, was separated from the concentrate.

Sixth step

To a mixture of 0.386 g (1 mmol) of R-1''-trifluoromethylheptyl trans-4-(4'-hydroxyphenyl)cyclohexanecarboxylate obtained in the fifth step, 0.328 g (1 mmol) of 1,2,3,4-tetrahydro-6-n-decyloxynaphthalene-2-carboxylic acid obtained in the first step, 0.012 g (0.1 mmol) of 4-N,N-dimethylaminopyridine and 10 ml of methylene chloride was added dropwise a methylene chloride solution prepared by dissolving 0.206 g (1 mmol) of N,N'-dicyclohexylcarbodiimide in 2 ml of methylene chloride with stirring at room temperature over a period of 1 hour.

The reaction was carried out at room temperature for additional 8 hours.

The reaction mixture was filtered, and the filtrate was concentrated. Using column chromatography, 0.628 g of a white solid was separated from the concentrate.

FD-mass spectrum of this semi-solid was measured to obtain an M/e value of 700.

Figure 21:
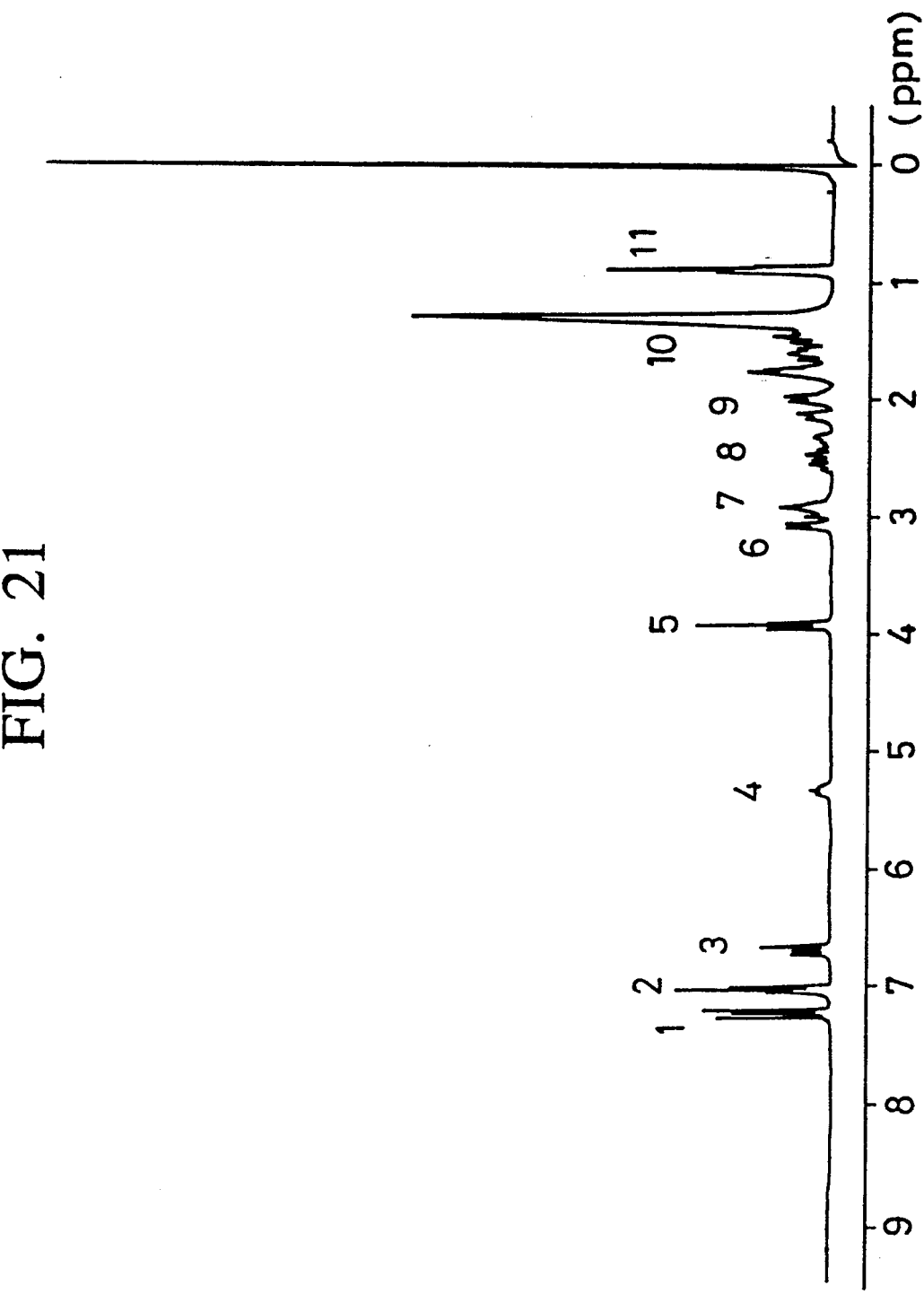
FIG. 21 is a chart showing $^1$H-NMR spectrum of R-1'''-trifluoromethylheptyl trans-4-[4'-(1'',2'',3'',4''-tetrahydro-6''-n-decyloxy-2''-naphthoyloxy)phenyl]cyclohexanecarboxylate.

FIG. 21 shows a chart of $^1$H-NMR spectrum of this compound.

From the results of the analyses, the compound was identified to be R-1'''-trifluoromethylheptyl trans-4-[4'(1'',2'',3'',4''-tetrahydro-6''-n-decyloxy-2''-naphthoyloxy)phenyl]cyclohexanecarboxylate which was the desired compound.

EXAMPLE 24

Synthesis of R-1'''-trifluoromethylheptyl 4-[6'-1'',2'',3'',4''-tetrahydro-6''-n-decyloxy-2''-naphthoyloxy)-1',2',3',4'-tetrahydro-2'-naphthoyloxy]benzoate exemplified compound [39]

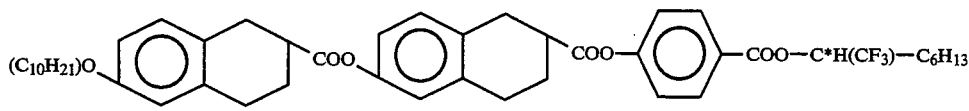

First step

A mixture of 1.44 g (8 mmol) of 1,2,3,4-tetrahydro-6-hydroxynaphthalene-2-carboxylic acid, 5.47 g (32 mmol) of benzyl bromide, 4.42 g (32 mmol) of potassium carbonate and 40 ml of dimethylformamide was heated at 120° C. and stirred for 10 hours.

The reaction mixture was cooled to room temperature, and poured into 100 ml of water. The resulting mixture was acidified with hydrochloric acid, and toluene was added thereto to form an organic layer, which was separated.

The separated organic layer was concentrated under reduced pressure to obtain 3.29 g of a solid. The solid was washed with hexane to obtain 2.91 g (7.82 mmol) of benzyl 1,2,3,4-tetrahydro-6-benzyloxynaphthalene-2-carboxylate.

Second step

A mixture of 2.91 g (7.82 mmol) of benzyl 1,2,3,4-tetrahydro-6-benzyloxynaphthalene-2-carboxylate obtained in the first step, 1.32 g (20 mmol) of 85% potassium hydroxide-containing aqueous solution and a solvent mixture of 30 ml of ethanol and 30 ml of water was stirred at room temperature for 13 hours.

The reaction mixture was poured into 200 ml of water, and the resultant reaction system was acidified by adding dropwise hydrochloric acid to precipitate a solid. The solid was separated by filtering, and washed with hexane to obtain 1.39 g (4.93 mmol) of 1,2,3,4-tetrahydro-6-benzyloxy-naphthalene-2-carboxylic acid.

Third step

To a mixture of 1.128 g (4 mmol) of 1,2,3,4-tetrahydro-6-benzyloxynaphthalene-2-carboxylic acid obtained in the second step, 1.54 g (4 mmol) of R-1'-trifluoromethylheptyl 4-hydroxybenzoate, 0.21 g (1 mmol) of 4-N,N-dimethylamino-pyridine and 20 ml of methylene chloride was added dropwise with stirring for 1 hour a methylene chloride solution prepared by dissolving 0.8 g (4 mmol) of N,N'-dicyclohexane-carbodiimide in 10 ml of methylene chloride.

The reaction was further carried out at room temperature for additional 10 hours.

The reaction mixture was then filtered, and the filtrate was concentrated. Using column chromatography, 2.28 g (3.51 mmol) of R-1''-trifluoromethylheptyl 4'-(1,2,3,4-tetrahydro-6-benzyloxy-2-naphthoyloxy)benzoate, a pale yellow liquid, was separated from the concentrate.

Fourth Step

Hydrogen was passed through a mixture solution of 1.4 g (2.46 mmol) of R-1''-trifluoromethylheptyl 4'-(1,2,3,4-tetrahydro-6-benzyloxy-2-naphthoyloxy)benzoate obtained in the third step, 1.4 g of a catalyst of 5% palladium supported on carbon and 50 ml of tetrahydrofuran for 28 hours.

The reaction mixture was then filtered with Celite, a filter aid, and the filtrate was concentrated. Using column chromatography, 1.05 g (2.16 mmol) of R-1''-trifluoromethyl-heptyl 4'-(1,2,3,4-tetrahydro-6-hydroxynaphthoyloxy)benzoate, a white solid, was separated from the concentrate.

Fifth step

To a mixture of 0.40 g (0.84 mmol) of R-1''-trifluoromethylheptyl 4'-(1,2,3,4-tetrahydro-6-hydroxynaphthoyloxy) benzoate obtained in the fourth step, 0.28 g (0.84 mmol) of 1,2,3,4-tetrahydro-6-n-decyloxy-naphthalene-2-carboxylic acid obtained in the first step in Example 1, 0.012 g (0.1 mmol) of 4-N,N-dimethylaminopyridine and 10 ml of methylene chloride was added dropwise a methylene chloride solution prepared by dissolving 0.206 g (1 mmol) of N,N'-dicyclohexylcarbodiimide into 2 ml of methylene chloride with stirring at room temperature over a period of 1 hour.

The reaction was carried out at room temperature for additional 8 hours.

The reaction mixture was filtered, and the filtrate was concentrated.

Using column chromatography, 0.33 g of a white solid was separated from the concentrate.

FD-mass spectrum of this semi-solid was measured to obtain an M/e value of 792.

Figure 22:
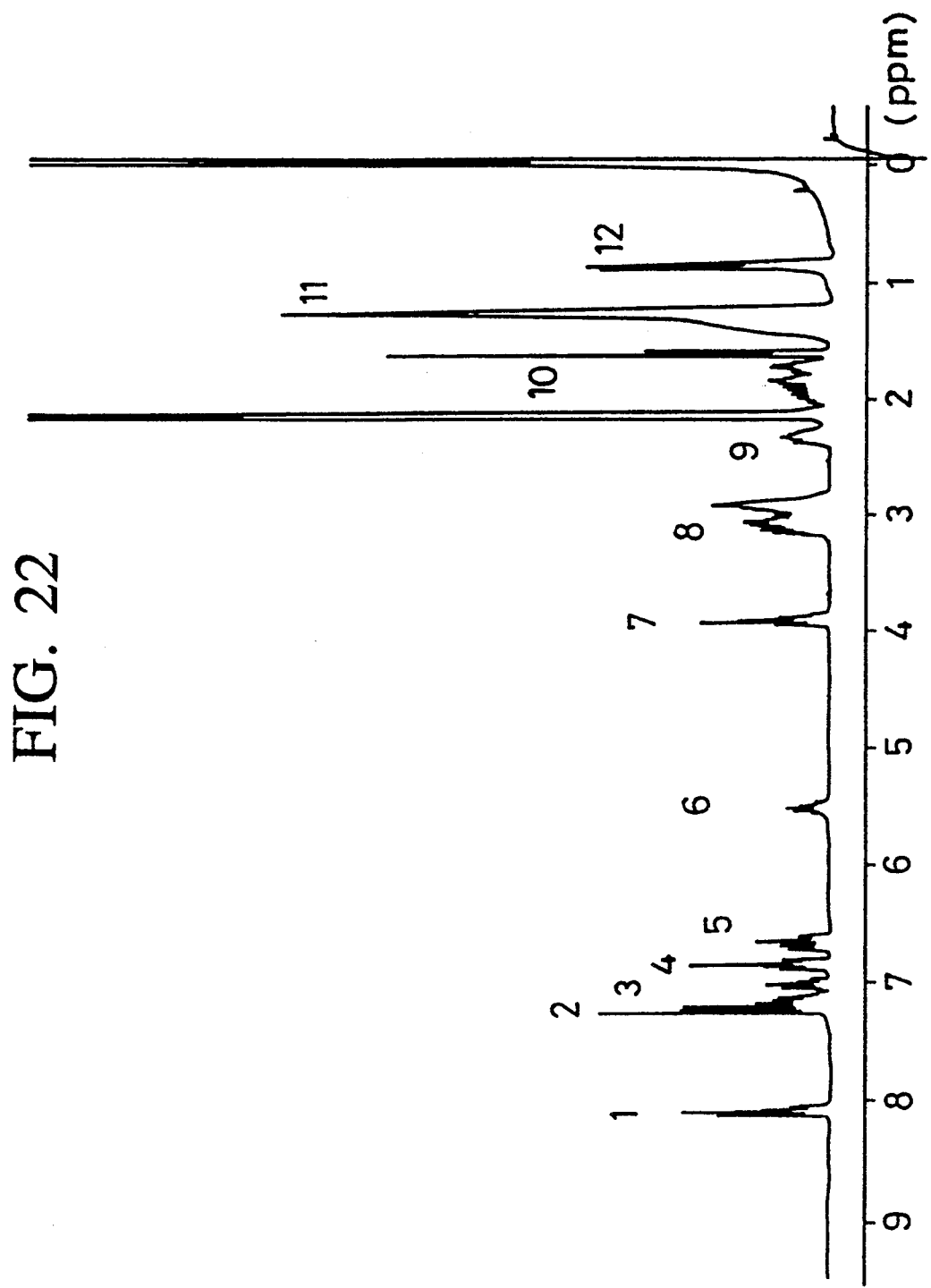
FIG. 22 is a chart showing $^1$H-NMR spectrum of R-1'''-trifluoromethylheptyl 4-[6'-(1'',2'',3'',4''-tetrahydro-6''-n-decyloxy-2''-naphthoyloxy)-1',2',3',4'-tetrahydro-2'-naphthoyloxy]benzoate.

FIG. 22 shows a chart of $^1$H-NMR spectrum of this compound.

From the results of the analyses, the compound was identified to be R-1'''-trifluoromethylheptyl 4-[6'-(1'',2'',3'',4''-tetrahydro-6''-n-decyloxy-2''-naphthoyloxy)-1',2',3',4'-tetrahydro-2'-naphthoyloxy]benzoate which was the desired compound.

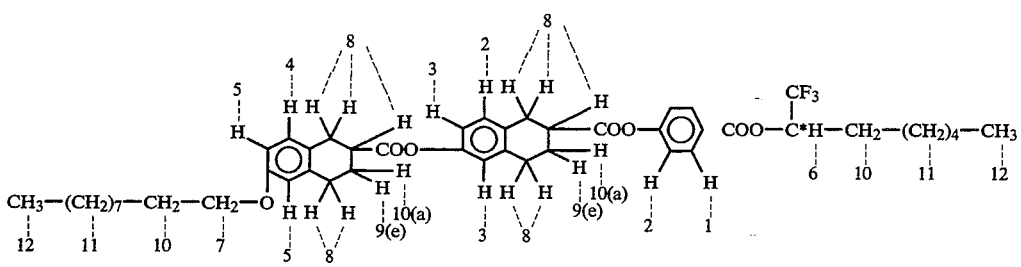

EXAMPLE 25

Synthesis of R-1''-trifluoromethylheptyl 6-(1',2',3',4'-tetrahydro-6'-n-decyloxy-2'-naphthoyloxy)-1,2,3,4-tetrahydronaphtharene-2-carboxylate.

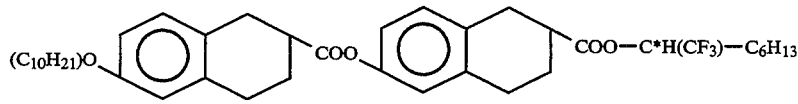

exemplified compound [29]

First step

To a mixture of 0.564 g (2 mmol) of 1,2,3,4-tetrahydro-6-benzyloxynaphthalene-2-carboxylic acid obtained in the second step in Example 24, 0.37 g (2 mmol) of R-1-trifluoromethylheptyl alcohol, 0.024 g (0.2 mmol) of 4-N,N-dimethylaminopyridine and 10 ml of methylene chloride was added dropwise a methylene chloride solution prepared by dissolving 0.453 g (2.2 mmol) of N,N'-dicyclohexanecarbodiimide in 5 ml of methylene chloride with stirring over a period of 1 hour.

The reaction was carried out at room temperature for additional 4 hours.

The reaction mixture was filtered, and filtrate was concentrated.

Using column chromatography, 0.70 g (1.56 mmol) of R-1'-trifluoromethylheptyl 1,2,3,4-tetrahydro-6-benzyloxynaphthalene-2-carboxylate, a pale yellow liquid, was separated from the concentrate.

Second step

Hydrogen was passed through a mixture solution of 0.70 g (1.56 mmol) of R-1'-trifluoromethylheptyl 1,2,3,4-tetrahydro-6-benzyloxynaphthalene-2-carboxylate obtained in the first step, a catalyst of 0.35 g of a catalyst containing 5% palladium supported on carbon and 10 ml of tetrahydrofuran.

The reaction mixture was filtered with Celite, a filter aid, and the filtrate was concentrated. Using column chromatography, 0.56 g (1.56 mmol) of R-1'-trifluoromethyl-heptyl 1,2,3,4-tetrahydro-6-hydroxynaphthalene-2-carboxylate, a white solid, was separated from the concentrate.

Third step

To a mixture of 0.27 g (0.75 mmol) of R-1'-trifluoromethylheptyl 1,2,3,4-tetrahydro-6-hydroxynaphthalene-2-carboxylate obtained in the second step, 0.25 g (0.75 mmol) of 1,2,3,4-tetrahydro-6-n-decyloxy-naphthalene-2-carboxylate, 0.0092 g (0.075 mmol) of 4-N,N-dimethylaminopyridine and 10 ml of methylene chloride was added dropwise a methylene chloride solution prepared by dissolving 0.19 g (0.75 mmol) of N,N'-dicyclohexylcarbodiimide in 5 ml of methylene chloride with stirring at room temperature over a period of 1 hour.

The reaction was carried out at room temperature for additional 5 hours.

The reaction mixture was filtered, and the filtrate was concentrated.

Using column chromatography, 0.35 g of a semi-solid was separated from the concentrate.

FD-mass spectrum of this semi-solid was measured to obtain an M/e value of 672.

Figure 23:
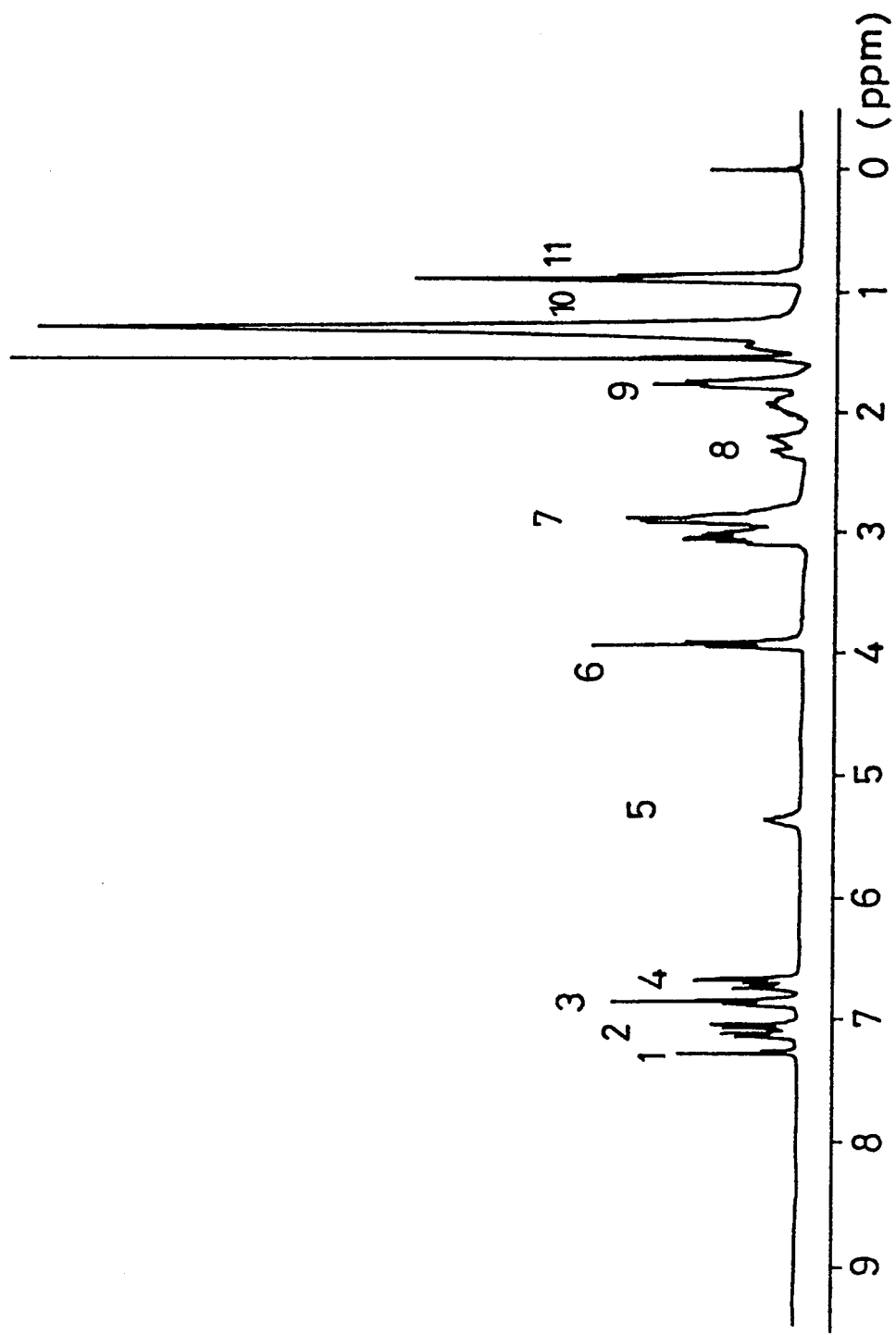
FIG. 23 is a chart showing $^1$H-NMR spectrum of R-1''-trifluoromethylheptyl 6-(1',2',3',4'-tetrahydro-6'-n-decyloxy-2'-naphthoyloxy)-1,2,3,4-tetrahydronaphtharene-2-carboxylate.

FIG. 23 shows a chart of $^1$H-NMR spectrum of the compound.

From the results of these analyses, the compound was identified to be R-1'''-trifluoromethylheptyl 6-(1',2',3',4'-tetrahydro-6'-n-decyloxy-2'-naphthoyloxy)-1,2,3,4-tetrahydronaphtharene-2-carboxylate which was the desired compound.

mixture was allowed to undergo reaction for 11 hours under reflux. After cooling the reaction mixture to room temperature, the metallic sodium remaining in the mixture was changed into sodium alcoholate by the addition of ethanol, and the reaction mixture was acidified with 36% hydrochloric acid.

After addition of 100 ml of water to the reaction mixture, an organic layer was separated therefrom, and washed with water.

The organic layer was concentrated under reduced pressure to obtain 4.25 g of a solid. The solid was recrystallized from toluene to obtain 2.95 g (8.89 mmol) of 1,2,3,4-tetrahydro-6-n-decyloxynaphthalene-2-carboxylic acid.

Second step

In a 1-liter volume of autoclave were mixed 30 g (160 mmol) of 6-hydroxynaphthalene-2-carboxylic acid, 5 g of a catalyst containing 5% palladium supported on carbon and 500 ml of tetrahydrofuran, and the mixture was heated to 105° C. in a nitrogen atmosphere.

The reaction was carried out with stirring at 105° C. for 3 hours while the hydrogen pressure in the autoclave was kept at 20 kg/cm$^2$.

The contents in the autoclave were allowed stand to cool to room temperature, and the hydrogen pressure was depressurized. The resultant reaction mixture was filtered with Celite, a filter aid, and the filtrate was concentrated.

The mixture thus obtained was recrystallized from toluene to obtain 16.1 g of white crystals.

FD-mass spectrum of this compound was measured to obtain an M/e value of 192.

Figure 24:
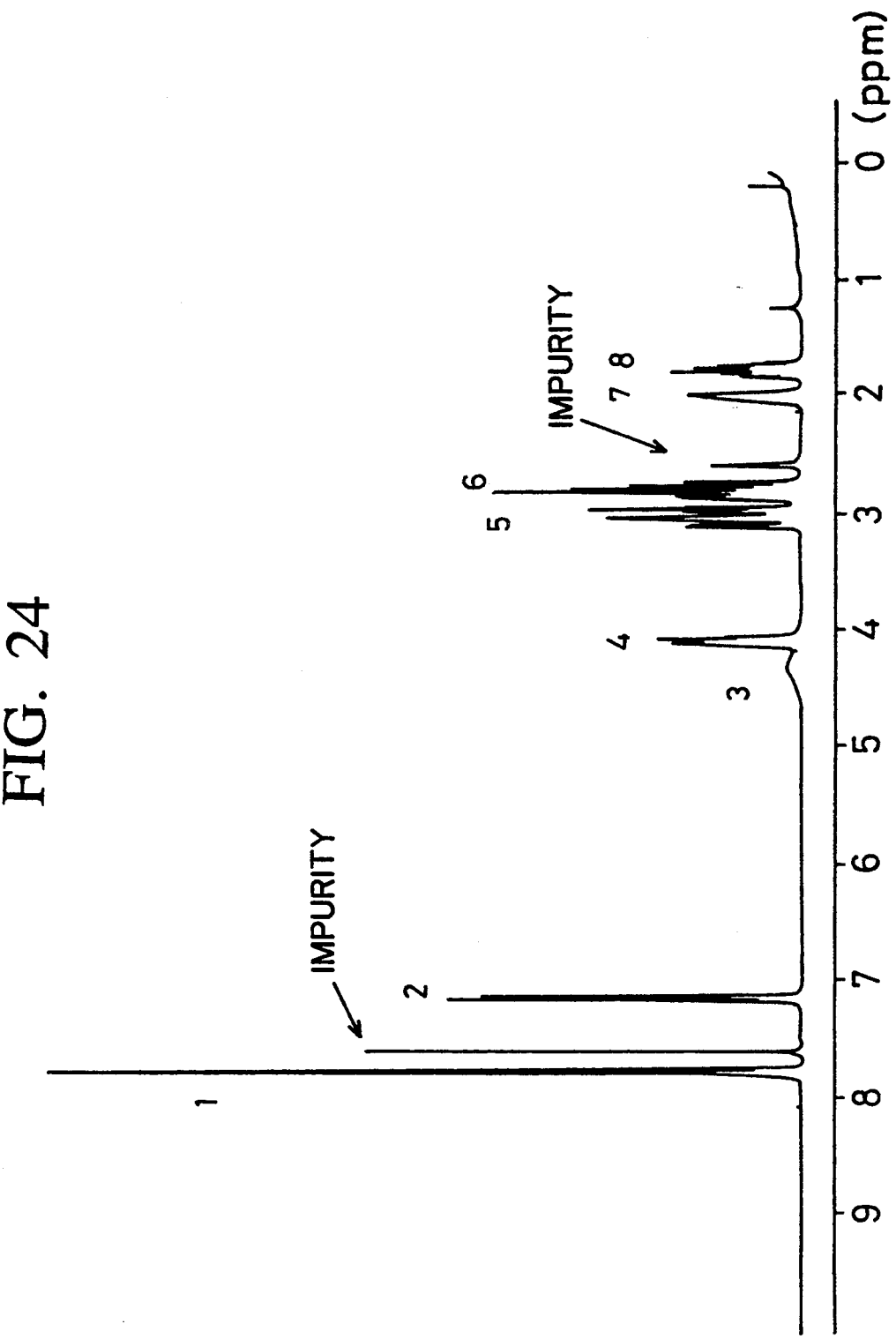
FIG. 24 is a chart showing $^1$H-NMR spectrum 5,6,7,8-tetrahydro-6-hydroxynaphthalene-2-carboxylic acid.

FIG. 24 shows a chart of $^1$H-NMR spectrum on this compound.

From the results of these analyses, the compound was identified to be 5,6,7,8-tetrahydro-6-hydroxynaphthalene-2-carboxylic acid

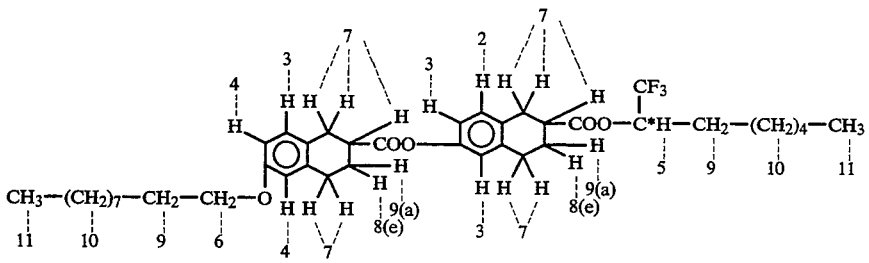

EXAMPLE 26

Synthesis R-1'''-trifluoromethylhepthyl 4-[6'-(1'',2'',3'',4''-tetrahydro-6''-n-decyloxy-2''-naphthoyloxy)-5',6',7',8'-tetrahydro-2'-naphthoyloxy]benzoate

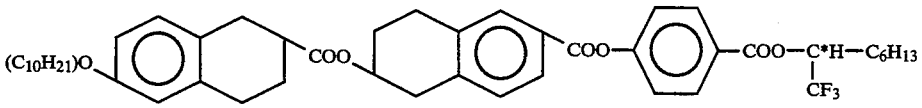

exemplified compound [41]

First step

To a mixture of 3.86 g (11.8 mmol) of 6-n-decyloxynaphthalene-2-carboxylic acid and 130 ml of 1,2-diethoxyethane was added in a nitrogen atmosphere with stirring 3.0 g (130 mg atom) of metallic sodium, and the mixture was then heated to a refluxing temperature.

To this mixture was added dropwise 10 g (114 mmol) of isoamyl alcohol over a period of 1 hour, and the

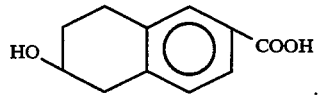

Third step

To a mixture of 0.96 g (5 mmol) of 5,6,7,8-tetrahydro-6-hydroxynaphthalene-2-carboxylic acid obtained in the second step, 1.52 g (5 mmol) of R-1'-trifluoromethylheptyl 4-hydroxybenzoate, 0.061 g (0.5 mmol) of 4-N,N-dimethylaminopyridine and 30 ml of methylene chloride was added dropwise 10 ml of a methylene chloride solution containing 1.13 g (5.5 mmol) of N,N'-dicyclohexylcarbodiimide with stirring at room temperature over a period of 5 hours. The reaction was carried out at room temperature for additional 20 hours.

The reaction mixture was filtered, and the filtrate was concentrated. Using column chromatography, 2.18 g (4.56 mmol) of R-1''-trifluoromethylheptyl 4'-(5,6,7,8-tetrahydro-6-hydroxynaphthoyloxy) benzoate, a colorless viscous liquid, was separated from the concentrate.

Fourth step

To a mixture of 1.48 g (1 mmol) of R-1''-trifluoromethylheptyl 4'-(5,6,7,8-tetrahydro-6-hydroxynaphthoyloxy) benzoate obtained in the third step, 0.33 g (1 mmol) of 1,2,3,4-tetrahydro-6-n-decyloxynaphthalene-2-carboxylic acid, 0.012 g (0.1 mmol) of 4-N,N-dimethylamino-pyridine and 10 ml of methylene chloride was added dropwise a methylene chloride solution prepared by dissolving 0.25 g (1.2 mmol) of N,N'-dicyclohexylcarbodiimide in 5 ml of methylene chloride with stirring at room temperature over a period of 3 hours.

The reaction was carried out at room temperature for additional 24 hours.

The reaction mixture was filtered, and the filtrate was concentrated.

Using column chromatography, 0.55 g (38.2 mmol) of a white solid was separated from the concentrate.

FD-mass spectrum of this white solid was measured to obtain an M/e value of 792.

Figure 25:
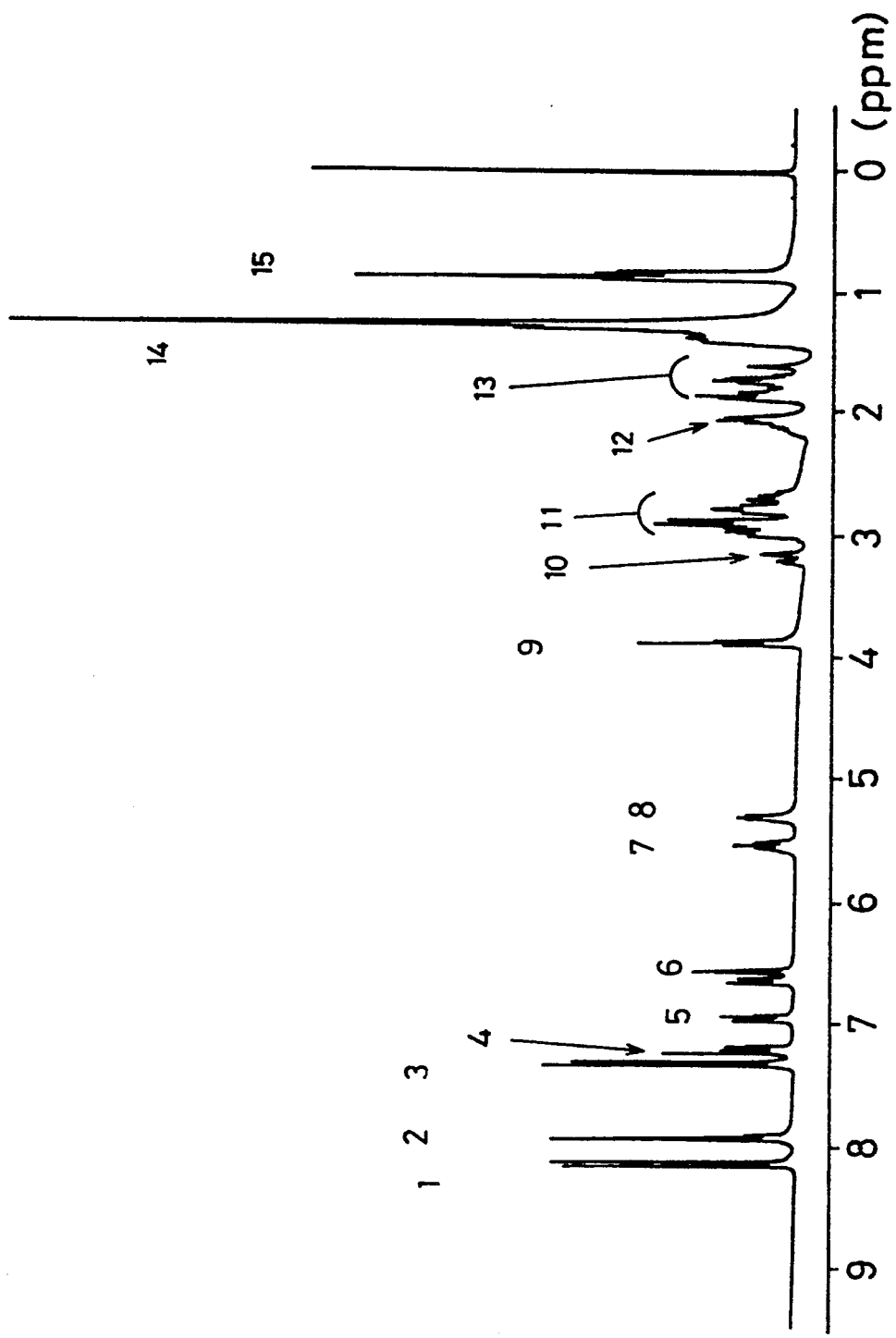
FIG. 25 is a chart showing $^1$H-NMR spectrum of R-1'''-trifluoromethylheptyl 4-[6'-(1'',2'',3'',4''-tetrahydro-6''-n-decyloxy-2''-naphthoyloxy)-5',6',7',8'-tetrahydro-2'-naphthoyloxy]benzoate

FIG. 25 shows a chart of $^1$H-NMR spectrum measured on this compound.

From the results of these analyses, the compound was identified to be R-1'''-trifluoromethylheptyl 4-[6'-(1'',2'',3'',4''-tetrahydro-6''-n-decyloxy-2''-naphthoyloxy)-5',6',7',8'-tetrahydro-2'-naphthoyloxy]benzoate of the following formula which was the desired compound.

EXAMPLE 27

Synthesis of R-1''''-trifluoromethylheptyl 6-[4'-(1'',2'',3'',4''-tetrahydro-6''-n-decyloxy-2''-naphthoyloxy)benzoyloxy]-5,6,7,8-tetrahydronaphthalene-2-carboxylate

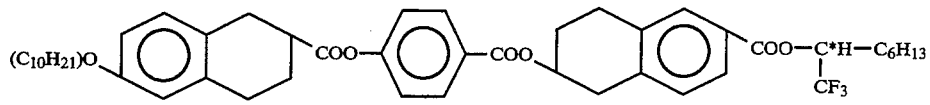

exemplified compound [42]

First step

To a mixture of 1.66 g (5 mmol) of 1,2,3,4-tetrahydro-6-n-decyloxynaphthalene-2-carboxylic acid obtained in the first step in Example 26, 1.14 g (5 mmol) of benzyl 4-hydroxybenzoate, 0.12 g (1 mmol) of 4-N,N-dimethylaminopyridine and 20 ml of methylene chloride was added dropwise 10 ml of a methylene chloride solution containing 1.03 g (5 mmol) of N,N'-dicyclohexylcarbodiimide with stirring at room temperature over a period of 1 hour.

The reaction was carried out at room temperature for additional 10 hours.

The reaction mixture was filtered, and the filtrate was concentrated. Using column chromatography, 2.32 g (4.28 mmol) of benzyl 4-(1',2',3',4'-tetrahydro-6'-n-decyloxy-2'-naphthoyloxy)benzoate, a white solid, was separated from the concentrate.

Second step

Hydrogen was passed through a mixture of 2.17 g (4 mmol) of benzyl 4-(1',2',3',4'-tetrahydro-6'-n-decyloxy-2'-naphthoyloxy)benzoate obtained in the first step, 1 g of a catalyst containing 5% palladium supported on carbon and 30 ml of tetrahydrofuran with stirring at room temperature and atmospheric pressure for 8 hours. The reaction mixture was filtered with Celite, a filter aid, and the filtrate obtained was concentrated to obtain 1.59 g (3.52 mmol) of 4-(1',2',3',4'-tetrahydro-6'-n-decyloxy-2'-naphthoyloxy) benzoic acid, a white solid.

Third Step

To a mixture of 2.88 g (15 mmol) of 5,6,7,8-tetrahydro-6-hydroxynaphthalene-2-carboxylic acid obtained in the second step in Example 26, 2.76 g (15 mmol) of R-1-trifluoromethylheptyl alcohol, 0.18 g (1.5 mmol) of 4-N,N-dimethylaminopyridine and 50 ml of methylene chloride was added a methylene chloride solution pre-

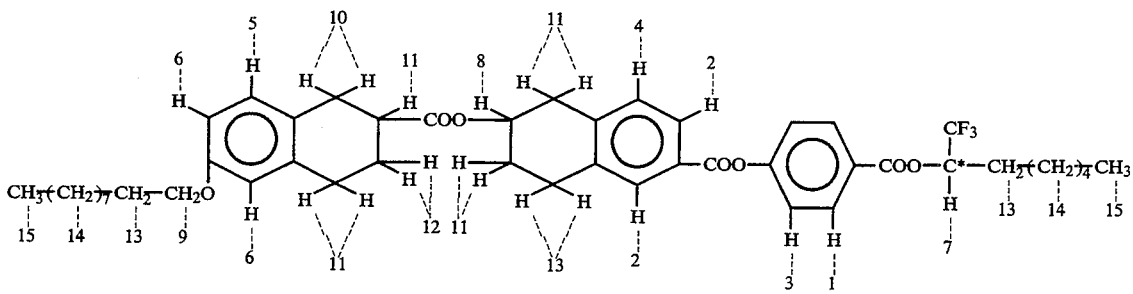

Notes: (a) and (e) being as defined in Example 13.

pared by dissolving 3.40 g (16.5 mmol) of N,N'-dicyclohexylcarbodiimide in 20 ml of methylene chloride with stirring at room temperature over a period of 8 hours.

The reaction was carried out for additional 24 hours.

The reaction mixture was filtered, and the filtrate was concentrated.

Using column chromatography, 3.11 g (8.69 mmol) of R-1'-trifluoromethylheptyl 5,6,7,8-tetrahydro-6-hydroxynaphthalene-2-carboxylate, a colorless viscous liquid, was separated from the concentrate.

Fourth step

To a mixture of 0.36 g (0.8 mmol) of 4-(1',2',3',4'-tetrahydro-6'-n-decyloxy-2'-naphthoyloxy) benzoic acid obtained in the second step, 0.29 g (0.8 mmol) of R-1'-trifluoromethylheptyl 5,6,7,8-tetrahydro-6-hydroxynaphthalene-2-carboxylate obtained in the third step and 0.010 g (0.08 mmol) of 4-N,N-dimethylaminopyridine and 10 ml of methylene chloride was added a methylene chloride solution prepared by dissolving 0.20 g (0.96 mmol) of N,N'-dicyclohexylcarbodiimide in 3 ml of methylene chloride with stirring over a period of 2 hours.

The reaction was carried out at room temperature for additional 20 hours.

The reaction mixture was filtered, and the filtrate was concentrated.

Using column chromatography, 0.29 g of a semi-solid was obtained from the concentrate.

FD-mass spectrum of this semi-solid was measured to obtain an M/e value of 792.

Figure 26:
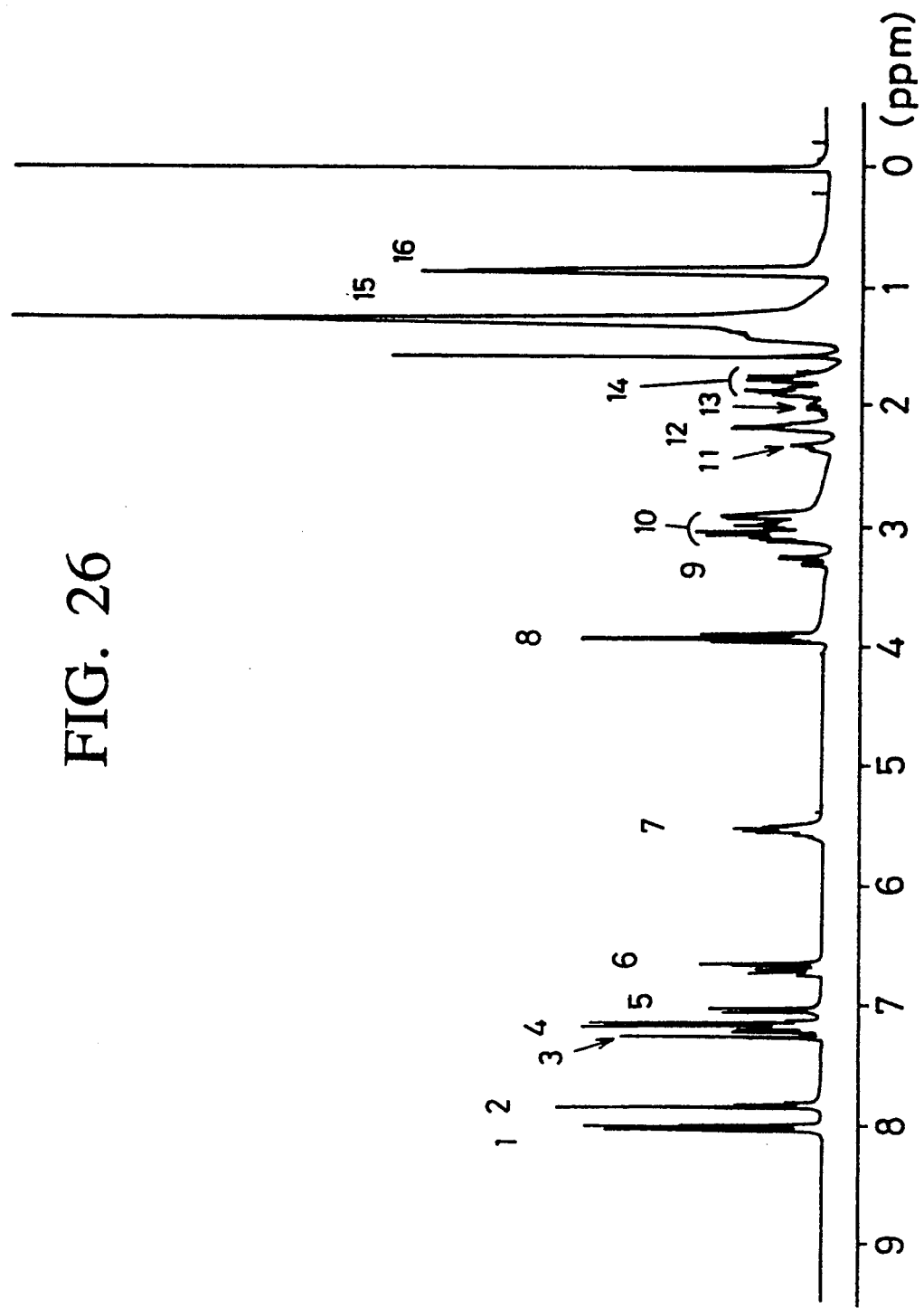
FIG. 26 is a chart showing $^1$H-NMR spectrum of R-1'''-trifluoromethylheptyl 6-[4'-(1'',2'',3'',4''-tetrahydro-6''-n-decyloxy-2''-naphthoyloxy) benzoyloxy]-5,6,7,8-tetrahydronaphthalene-2-carboxylate.

FIG. 26 shows a chart of 1H-NMR spectrum of this compound.

From the results of the analyses, the compound was identified to be R-1'''-trifluoromethylheptyl 6-[4'-(1'',2'',3'',4''-tetrahydro-6''-n-decyloxy-2''-naphthoyloxy) benzoyloxy]-5,6,7,8-tetrahydronaphthalene-2-carboxylate of the following formula which was the desired compound.

exemplified compound [43]

First step

A mixture of 1.92 g (10 mmol) of 1,2,3,4-tetrahydro-6-hydroxynaphthalene-2-carboxylic acid, 2.57 g (15 mmol) of benzyl bromide, 1.32 g (20 mmol) of 85% potassium hydroxide-containing aqueous solution, 0.10 g (0.7 mmol) of sodium iodide, 40 ml of ethanol and 5 ml of water was heated to 100° C., and stirred under reflux for 7 hours To the reaction mixture was added 10 ml of 10% potassium hydroxide-containing aqueous solution, and the mixture was stirred at 100° C. for additional 2 hours.

After cooling to room temperature, the reaction mixture was poured into 100 ml of water, acidified with hydrochloric acid to precipitate crystals, and filtered to obtain the crystals. The crystals were washed at first with water and then with hexane, and dried under reduced pressure to obtain 2.50 g (8.87 mmol) of 1,2,3,4-tetrahydro-6-benzyloxy-naphthalene-2-carboxylic acid, a pale yellow solid.

Second Step

To a mixture of 0.56 g (2 mmol) of 1,2,3,4-tetrahydro-6-benzyloxynaphthalene-2-carboxylic acid, 0.37 g (2 mmol) of R-1-trifluoromethylheptyl alcohol, 0.024 g (0.2 mmol) of 4,N,N-dimethylaminopyridine and 10 ml of methylene chloride was added dropwise a methylene chloride solution prepared by dissolving 0.45 g (2.2 mmol) of N,N'-dicyclohexylcarbodiimide in 5 ml of methylene chloride with stirring over a period of 1 hour.

The reaction was carried out at room temperature for additional 4 hours.

The reaction mixture was filtered, and the filtrate was concentrated.

Using column chromatography, 0.70 g (1.56 mmol) of R-1'-trifluoromethylheptyl 1,2,3,4-tetrahydro-6-benzyloxynaphthalene-2-carboxylate, a white solid, was separated from the concentrate.

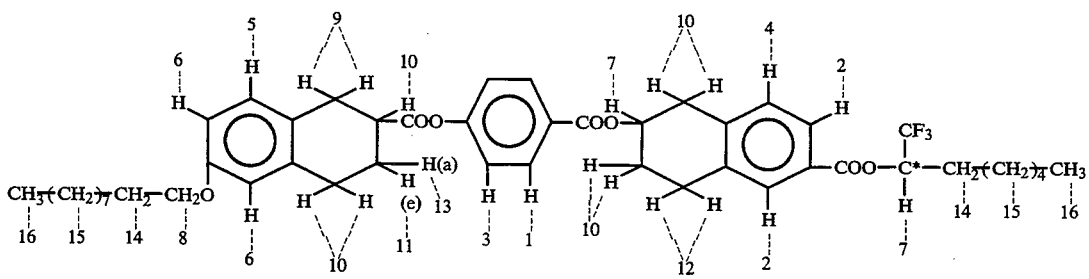

Notes: (a) and (e) being as defined in Example 13.

EXAMPLE 28

Synthesis of R-1'''-trifluoromethylheptyl 6-[4'(1'',2'',3'',4''-tetrahydro-6''-n-decyloxy-2''-naphthoyloxy) benzoyloxy]-1,2,3,4-tetrahydronaphthalene-2-carboxylate Third step Hydrogen was passed through a mixture of 0.70 g (1.56 mmol) of R-1'-trifluoromethylheptyl 1,2,3,4-tetrahydro-6-benzyloxynaphthalene-2-carboxylate obtained in the second step, 0.35 g of a catalyst containing

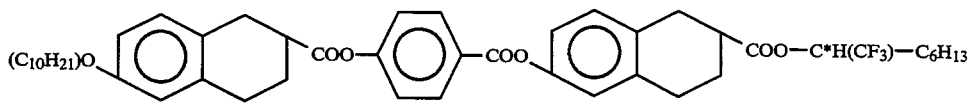

5% palladium supported on carbon and 10 ml of tetrahydrofuran for 36 hours.

Subsequently, the reaction mixture was filtered with Celite, a filter aid, and the filtrate was concentrated to obtain 0.56 g (1.56 mmol) of R-1'-trifluoromethylheptyl 1,2,3,4-tetrahydro-6-hydroxynaphthalene-2-carboxylate, a white solid.

Fourth step

To a mixture of 0.45 g (1 mmol) of 4-(1',2',3',4'-tetrahydro-6'-n-decyloxy-2'-naphthoyloxy) benzoic acid obtained in the second step in Example 27, 0.36 g (1 mmol) of R-1'-trifluoromethylheptyl 1,2,3,4-tetrahydro-6-hydroxynaphthalene-2-carboxylate obtained in the third step, 0.012 g (0.1 mmol) of 4-N,N-dimethylamonopyridine and 10 ml of methylene chloride was added dropwise a methylene chloride solution prepared by dissolving 0.25 g (1.2 mmol) of N,N'-dicyclohexylcarbodiimide in 5 ml of methylene chloride with stirring at room temperature over a period of 1 hour.

The reaction was carried out at room temperature for additional 6 hours.

The reaction mixture was filtered, and the filtrate was concentrated.

Using column chromatography, 0.60 g of a white solid was separated from the concentrate.

FD-mass spectrum of this white solid was measured to obtain an M/e value of 792.

Figure 27:
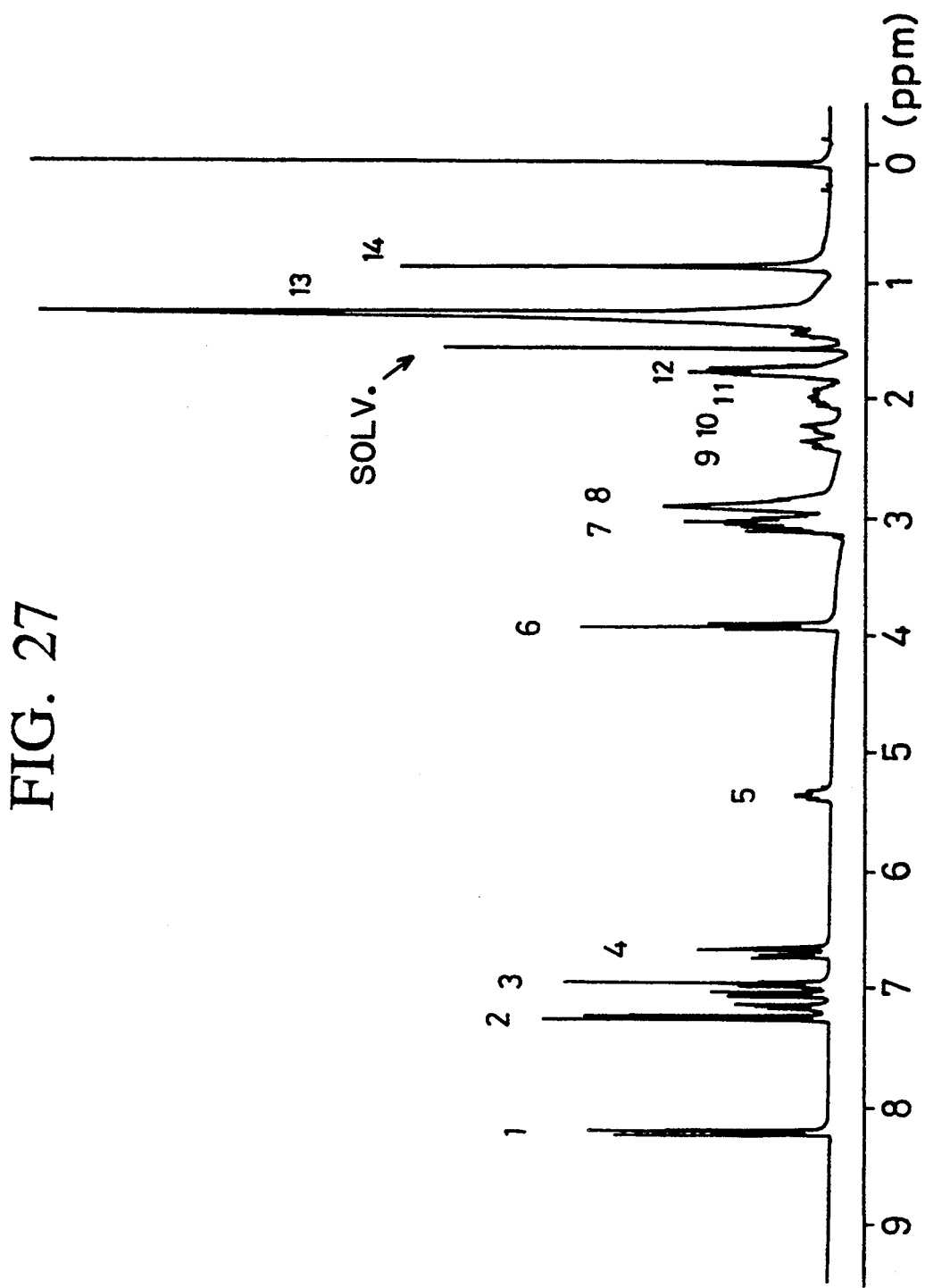
FIG. 27 is a chart showing $^1$H-NMR spectrum of R-1'''-trifluoromethylheptyl 6-[4'-(1'',2'',3'',4''-tetrahydro-6''-n-decyloxy-2''-naphthoyloxy)-benzoyloxy]-1,2,3,4-tetrahydronaphthalene-2-carboxylate.

FIG. 27 shows a chart of $^1$H-NMR spectrum of this compound.

From the results of the analyses, the compound was identified to be R-1'''-trifluoromethylheptyl 6-[4'-(1'',2'',3'',4''-tetrahydro-6''-n-decyloxy-2''-naphthoyloxy) benzoyloxy]-1,2,3,4-tetrahydronaphthalene-2-carboxylate of the following formula which was the desired compound.

First step

To a mixture of 3.32 g (10 mmol) of 5,6,7,8-tetrahydro-6-n-decyloxynaphthalene-2-carboxylic acid obtained by a procedure similar to that in the first step in Example 13, 2.14 g (10 mmol) of 4-[4'hydroxyphenyl]-benzoic acid, 12 g (1.00 mmol) of 4-N,N-dimethylaminopyridine and 50 ml of methylene chloride was added dropwise 15 ml of a methylene chloride solution containing 2.27 g (11 mmol) of N,N'-dicyclohexylcarbodiimide at room temperature with stirring over a period of 1.5 hours. The reaction was carried out at room temperature for additional 2.5 hours. The reaction mixture was filtered, and the precipitate thus obtained was extracted with tetrahydrofuran. The extract was concentrated, and recrystallized with a 1:1 mixture solvent of tetrahydrofuran and methylene chloride to obtain 3.23 g (6:1 mmol) of 4-[4'-(5'',6'',7'',8''-tetrahydro-6''-n-decyloxy-2''-naphthoyloxy) -phenyl]benzoic acid.

Second step

To a mixture of 0.53 g (1 mmol) of 4-[4'-(5'',6'',7'',8''-tetrahydro-6''-n-decyloxy-2''-naphthoyloxy)phenyl]-benzoic acid, 0.18 g (1 mmol) of R-1-trifluoromethylheptyl alcohol, 0.02 g (0.16 mmol) of 4-N,N-dimethylaminopyridine and 15 ml of methylene chloride was added dropwise 3 ml of a methylene chloride solution containing 0.25 g (1.2 mmol) of N,N'-dicyclohexylcarbodiimide at room temperature with stirring over a period of 0.5 hour. The reaction was carried out at room temperature for additional 3 hours. The reaction mixture was filtered, and the filtrate was concentrated. Using column chromatography, 0.40 g of a semi-solid was separated from the concentrate.

FD-mass spectrum of this semi-solid was measured to obtain an M/e value of 694.

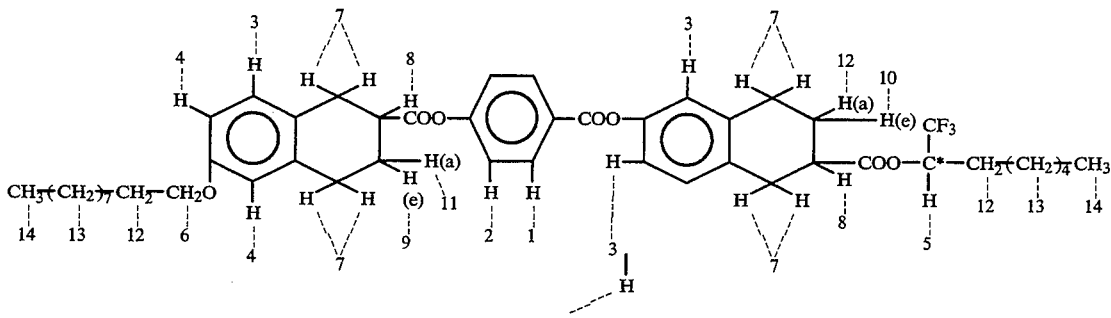

Notes: (a) and (e) being as defined in Example 13.

EXAMPLE 29

Figure 28:
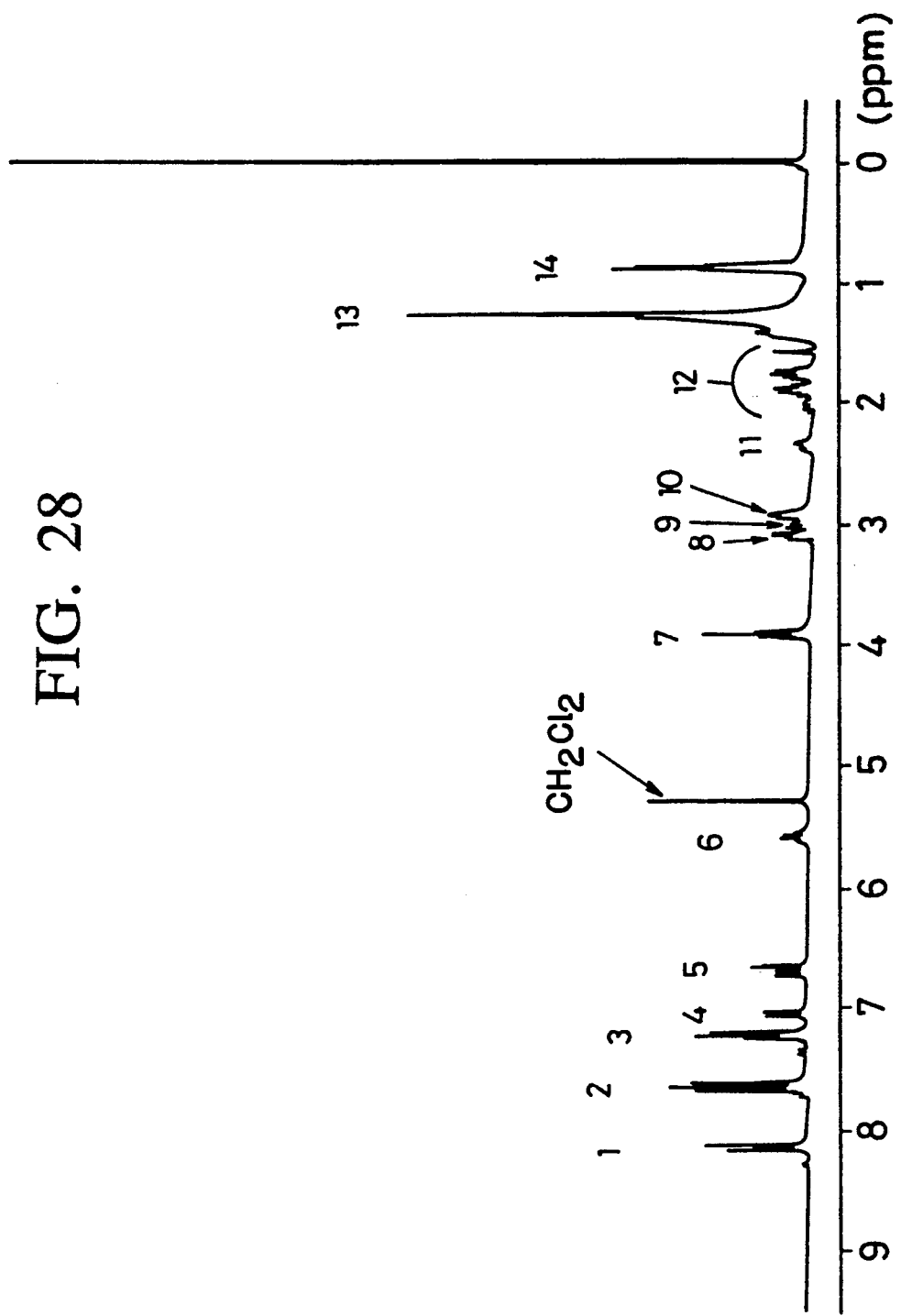
FIG. 28 is a chart showing $^1$H-NMR spectrum of R-1'''-trifluoromethylheptyl 4-[4'-(5'',6'',7'',8''-tetrahydro-6''-n-decyloxy-2''-naphthoyloxy)-phenyl]benzoate.

Synthesis of R-1'''-trifluoromethylheptyl 4-[4'-(5'',6'',7'',8''-tetrahydro-6''-n-decyloxy-2''-naphthoyloxy)phenyl]benzoate FIG. 28 shows a chart of $^1$H-NMR spectrum of the compound.

From the results of these analyses, the compound was identified to be R-1'''-trifluoromethylheptyl 4-[4'-(5'',6'',7'',8''-tetrahydro-6''-n-decyloxy-2''-naphthoyloxy) phenyl]benzoate which was the desired compound.

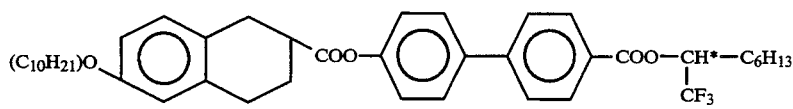

exemplified compound [44]

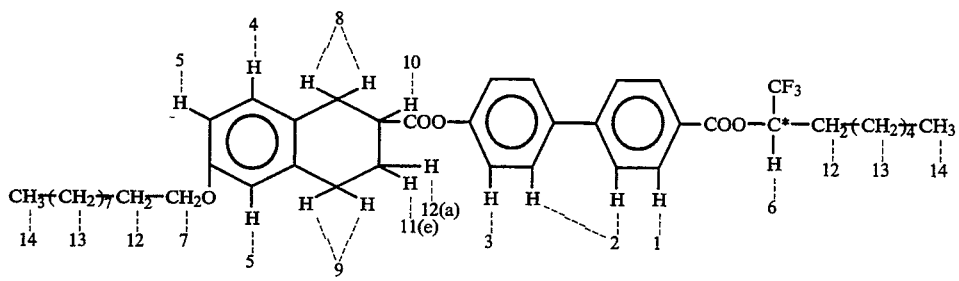

Notes: (a) and (e) being as defined in Example 13.

EXAMPLE 30

Synthesis of R-1″-trifluoromethylheptyl 6-(5′,6′,7′,8′-tetrahydro-6′-n-decyloxy-2′-naphthoyloxy)-1,2,3,4-tetrahydronaphthalene-2-carboxylate From the results of these analyses, the compound was identified to be R-1″-trifluoromethylheptyl 6-(5′,6′,7′,8′-tetrahydro-6′-n-decyloxy-2′-naphthoyloxy)-1,2,3,4-tetrahydronaphthalene-2-carboxylate which was the desired compound.

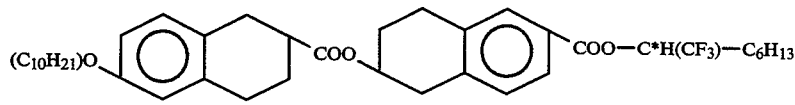

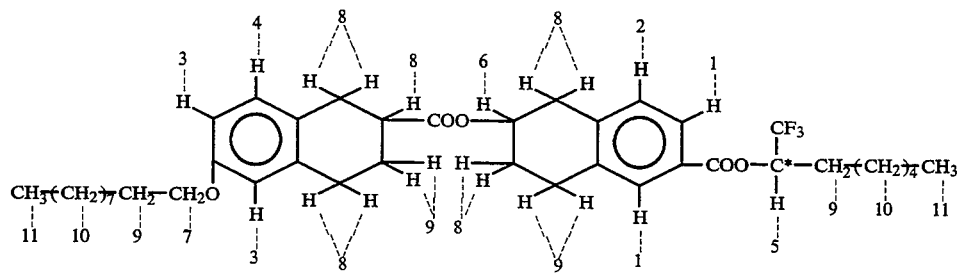

exemplified compound [40]

First step

To a mixture of 0.44 g (1.31 mmol) of 5,6,7,8-tetrahydro-6-n-decyloxynaphthalene-2-carboxylic acid obtained by a procedure similar to that in the first step in Example 13, 0.47 g (1.31 mmol) of R-1′-trifluormethylheptyl 5,6,7,8-tetrahydro-6-hydroxynaphthalene-2-carboxylate obtained by a procedure similar to that in the third step in Example 27, 0.016 g (0.13 mmol) of 4-N,N-dimethylaminopyridine and 10 ml of methylene chloride was added dropwise 5 ml of a methylene chloride solution containing 0.30 g (1.31 mmol) of N,N′-dicyclohexylcarbodiimide at room temperature with stirring over a period of 1 hour. The reaction was carried out at room temperature for additional 3 hours. The reaction mixture was filtered, and the filtrate was concentrated. Using column chromatography, 0.23 g of a viscous liquid was separated from the concentrate.

FD-mass spectrum of this viscous liquid was measured to obtain an M/e value of 672.

Figure 29:
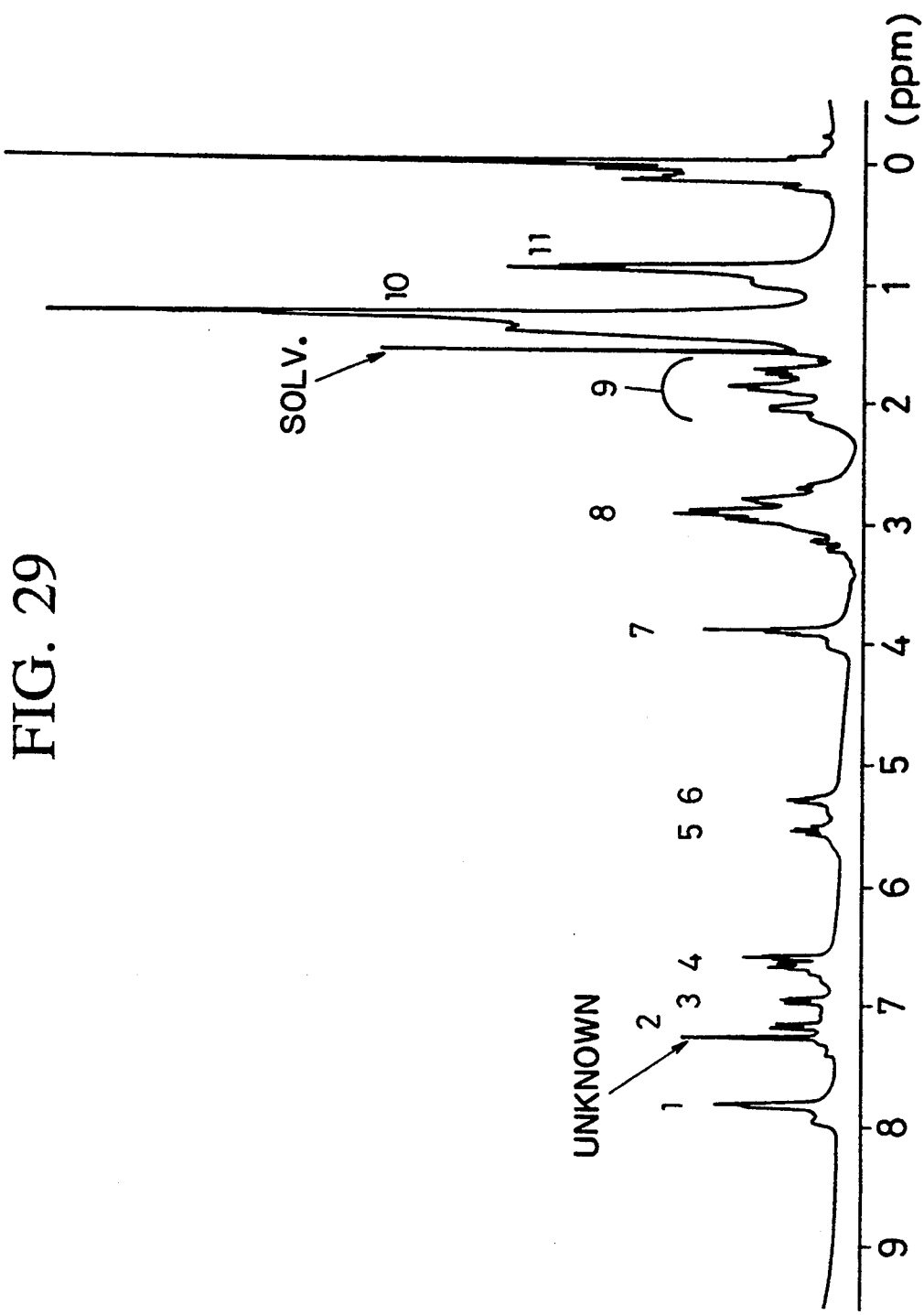
FIG. 29 is a chart showing $^1$H-NMR spectrum of R-1''-trifluoromethylheptyl 6-(5',6',7',8'-tetrahydro-6'-n-decyloxy-2'-naphthoyloxy)-1,2,3,4-tetrahydronaphthalene-2-carboxylate.

FIG. 29 shows a chart of $^1$H-NMR spectrum of the compound.

EXAMPLE 31

Synthesis of R-1‴-trifluoromethylheptyl 4-[4′(1″,2″,3″,4″-tetrahydro-6″-n-decyl-2″-naphthoyloxy) benzoyloxy]benzoate

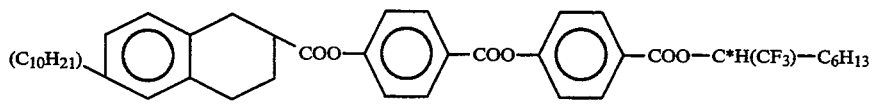

examplified compound [45]

First step

To a mixture of 0.62 g (2 mmol) of 6-n-decylnaphthalene-2-carboxylic acid and 30 ml of 1,2-diethoxyethane was added in a nitrogen atmosphere 0.60 g (26 mg atom) of metallic sodium, and the mixture was then heated to a refluxing temperature with stirring.

To this mixture was added dropwise 2.70 g (30.7 mmol) of isoamyl alcohol over a period of 2 hours, and the mixture was allowed to undergo reaction for 13 hours under reflux. After cooling the reaction mixture to room temperature, the metallic sodium remaining in the mixture was changed into sodium alcoholate by the addition of ethanol, and the reaction mixture was acidified with hydrochloric acid.

After addition of 10 ml of water to the reaction mixture, an organic layer was separated therefrom, and washed with water.

The organic layer was concentrated under reduced pressure to obtain 1.13 g of a solid. Using column chromatography, the solid was separated, and 0.30 g (0.95 mmol) of 1,2,3,4-tetrahydro-6-n-decylnaphthalene-2-carboxylic acid, a white solid, was obtained by recrystallization from hexane.

Second step

To a mixture of 12.34 g (40.6 mmol) of R-1'-trifluoromethylheptyl 4-hydroxybenzoate, 9.26 g (40.6 mmol) of 4-benzyloxybenzoic acid, 0.49 g (4 mmol) of 4-N,N-dimethylaminopyridine and 80 ml of methylene chloride was added dropwise a methylene chloride solution prepared by dissolving 9.20 g (44.7 mmol) of N,N'-dicyclohexylcarbodiimide in 50 ml of methylene chloride with stirring over a period of 2 hours.

The reaction was carried out at room temperature for additional 4 hours.

The reaction mixture was filtered, and the filtrate was concentrated.

Using column chromatography, 19.64 g (38.2 mmol) of R-1''-trifluoromethylheptyl 4-(4'-benzyloxybenzoyl)-benzoate, a white solid, was separated from the concentrate.

Third step

Hydrogen gas was passed through a micture of 19.64 g(38.2 mmol) R-1''-trifluoromethylheptyl 4-(4'-benzyloxybenzoyl)benzoate, obtained in the second step, 3.0 g of a catalyst containing of 5% palladium supported on carbon and 100 ml of tetrahydrofuran with stirring at room temperature and atmospheric pressure for 14 hours. The reaction mixture was filtered with Celite, a filter aid, and the filtrate obtained was concentrated to obtain 16.72 g(38.2 mmol) of R-1''-trifluoromethylheptyl 4-(4''-hydroxybenzoyl)benzoate, a white solid.

Fourth step

To a mixture of 0.27 g (0.85 mmol) of 1,2,3,4-tetrahydro-6-n-decylnaphthalene-2-carboxylic acid obtained in the first step, 0.36 g (0.85 mmol) of R-1''-trifluoromethylheptyl 4-(4'-hydroxybenzoyloxy)benzoate obtained in the third step, 0.010 g (0.085 mmol) of 4-N,N-dimethylaminopyridine and 10 ml of methylene chloride was added dropwise a methylene chloride solution prepared by dissolving 0.21 g (1.02 mmol) of N,N'-dicyclohexylcarbodiimide in 5 ml of methylene chloride with stirring over a period of 1 hour.

The reaction was carried out at room temperature for additional 4 hours.

The reaction mixture was filtered, and the filtrate was concentrated.

Using column chromatography, 0.50 g of a white solid was separated from the concentrate.

FD-mass spectrum of this white solid was measured to obtain an M/e value of 722.

Figure 30:
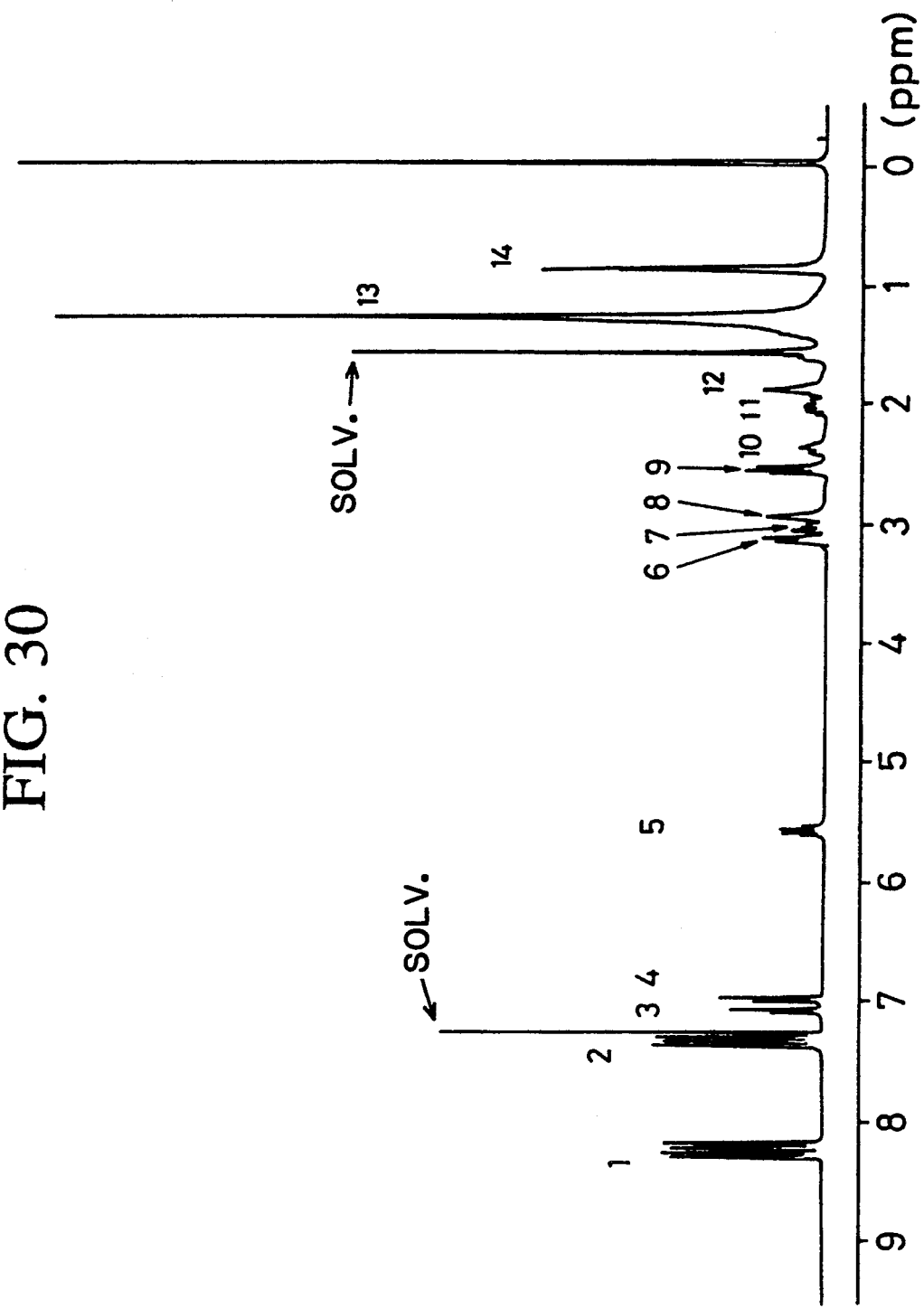
FIG. 30 is a chart showing $^1$H-NMR spectrum of R-1'''-trifluoromethylheptyl 4-[4'-(1'',2'',3'',4''-tetrahydro-6''-n-decyl-2''-naphthoyloxy) benzoyloxy]benzoate.

FIG. 30 shows a chart of $^1$H-NMR spectrum of this compound.

From the results of these analyses, the compound was identified to be R-1'''-trifluoromethylheptyl 4-[4(1'',2'',3'',4''-tetrahydro-6''-n-decyl-2''-naphthoyloxy)benzoyloxy]benzoate of the following formula which was the desired compound.

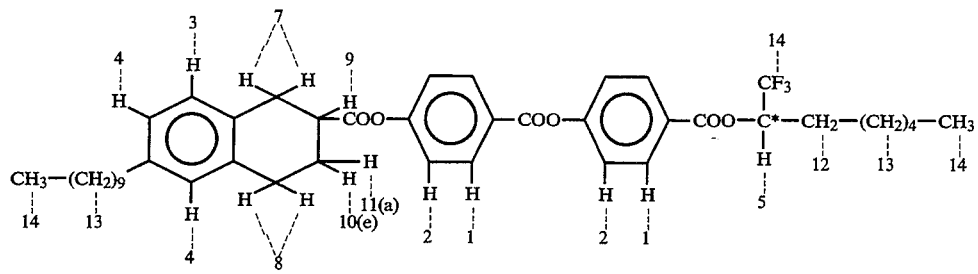

Notes: (a) and (e) being as defined in Example 13.

Measurement of the phase transition temperatures

The phase transition temperatures of the thus obtained compounds were determined by measurement with a DSC and observation of the phases with a polarized microscope under the conditions described below.

Measurement with a DSC instrument used: DSC 220 manufactured by Seiko Denshi Kogyo K.K.

conditions for measurement: rate of heating and cooling of 10° C./min (−150° C.–200° C.)

Observation by polarized microscope instrument used: OPTIPHOTOPOL manufactured by Nikon K.K.

conditions for observation: compounds obtained being observed after pouring each compound into a cell, as described in Example 4.

As to the compound whose phase transition temperature Tc, the critical temperature between crystal and liquid crystal phases, could not be clearly detected by the above-mentioned method of using either DSC or microscope, the compound was cooled at −30° C. for such a long time as 500 hours, and the temperature Tc was then measured by the method of using DSC again. When the temperature Tc could not still be detected again by this method, the compound was evaluated as having the temperature Tc lower than −30° C. The phase transition temperatures of the compounds are listed in Tables 5,6 and 7.

TABLE 5

| Compound | Phase transition temperature | | |
|---|---|---|---|
| | Cry-SmC* or SmA or Iso | SmC*-SmA | SmA-Iso |
| [3] | 45° C. | 84° C. | 95° C. |
| [4] | 50° C. | 82° C. | 95° C. |
| [6] | 43° C. | 80° C. | 92° C. |
| [7] | 41° C. | | 77° C. |
| [45] | 30° C. | 48° C. | 66° C. |

TABLE 6

| Compound | Phase transition temperature | | |
|---|---|---|---|
| | Cry-SmCA* or SmA or Iso | SmC*-SmA | SmA-Iso |
| [33] | 42° C. | – | 125° C. |
| [34] | 55° C. | 68° C. | 101° C. |
| [35] | 60° C. | | 159° C. |
| [36] | 51° C. | | 151° C. |

TABLE 7

| Compound | Phase transition temperature | | |
|---|---|---|---|
| | Cry-SmC* or SmA or Iso | SmC*-SmA or Iso | SmA-Iso |
| [21] | 36° C. | | 68° C. |
| [39] | −26° C. | 39° C. | 101° C. |
| [41] | 32° C. | 42° C. | |
| [42] | 44° C. | 52° C. | |
| [43] | 45° C. | 73° C. | 122° C. |
| [44] | 60° C. | 70° C. | 95° C. |

What is claimed is:

1. A carboxylate compound represented by the following formula (A):

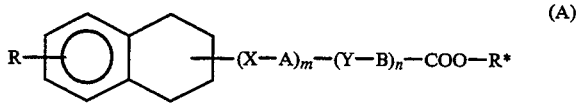

wherein R is a group selected from the group consisting of alkyl of 3–20 carbon atoms, alkoxy of 3–20 carbon atoms and halogenated alkyl of 3–20 carbon atoms, X and Y each represent —COO—, A and B each independently, represent a member selected from the group consisting of

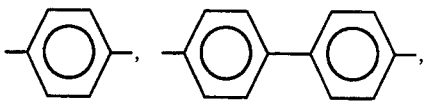

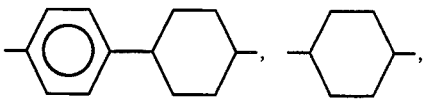

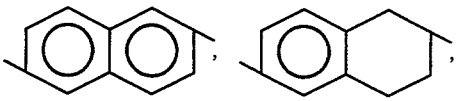

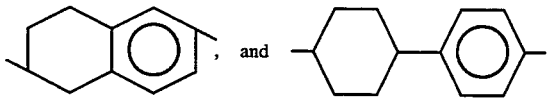

and R* is an optically active group of 4 to 20 carbon atoms containing at least one asymmetric carbon atom, wherein hydrogen atoms attached to the carbon atoms of said optically active group may be substituted with halogen atoms, and m and n are each, independently, an integer of from 0 to 2, with the proviso that both m and n are not both 0 at the same time.

2. The carboxylate compound as claimed in claim 1 wherein R is an alkyl or alkoxy group of 7–16 carbon atoms, X and Y are the same groups of —coo—, A and B independently represent a group selected from the group consisting of

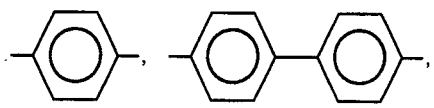

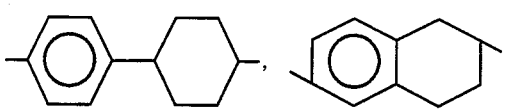

and 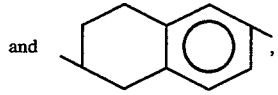

R* is an optically active alkyl or haloalkyl group of 5–9 carbon atoms which may be substituted with —COOC$_2$H$_5$, m is an integer of 0–2, and n is an integer of 0 or 1, with the proviso that both m and n do not become 0 at the same time.

3. The carboxylate compound as claimed in claim 2 wherein R is an alkyl or alkoxy group of 7–12 carbon atoms and R* is a group selected from the group consisting of

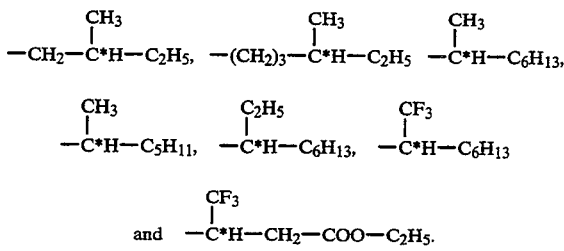

4. A liquid crystal compound which is a carboxylate compound represented by the above-mentioned following formula (A):

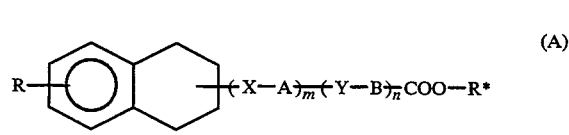

wherein R is selected from the group consisting of linear alkyl of 3–20 carbon atoms, linear alkoxy of 3–20 carbon atoms and halogenated linear alkyl of 3–20 carbon atoms, X and Y each represent —COO—, A and B independently represent a member selected from the group consisting of

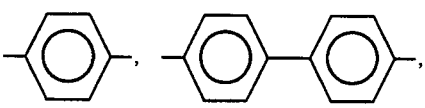

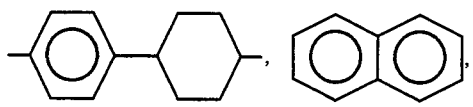

-continued

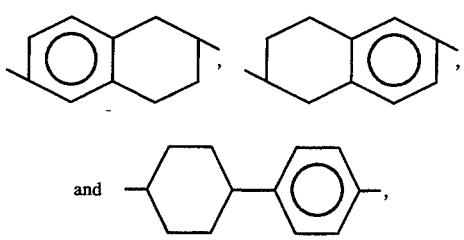

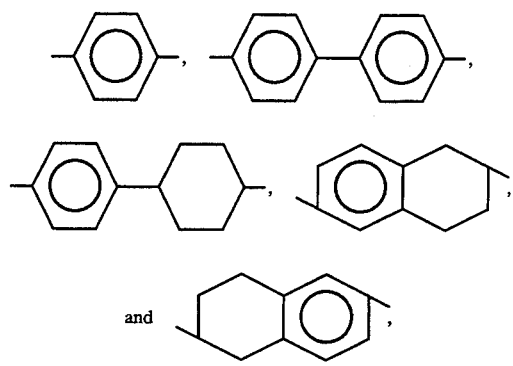

R* is an optically active group of 4–20 carbon atoms having at least one asymmetric carbon atom, wherein hydrogen atoms attached to the carbon atoms of said optically active group can be substituted with halogen atoms, and m and n are each, independently, 0, 1, or 2, with the proviso that m and n are not both 0.

5. The liquid crystal compound of claim 4 wherein R is an alkyl or alkoxy group of 7 to 16 carbon atoms, A and B each, independently, represent a group selected from the group consisting of

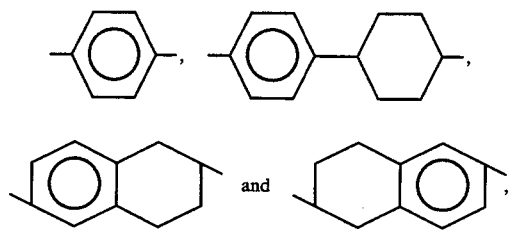

R* is an optically active alkyl or haloalkyl group of 5 to 9 carbon atoms which may be substituted with —COOC$_2$H$_5$, m is an integer of 1–2, and n is 0 or 1, with the proviso that both m and n are not both 0 at the same time.

6. The liquid crystal compound according to claim 5 wherein R is an alkyl or alkoxy group of 7 to 12 carbon atoms, A and B, each independently, represent a member selected from the group consisting of

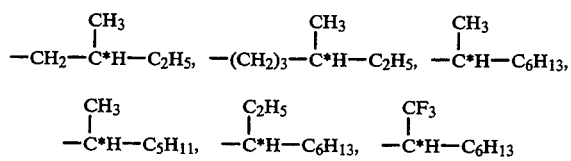

and R* is a member selected from the group consisting of

—CH$_2$—C*H(CH$_3$)—C$_2$H$_5$,  —(CH$_2$)$_3$—C*H(CH$_3$)—C$_2$H$_5$,  —C*H(CH$_3$)—C$_6$H$_{13}$,

—C*H(CH$_3$)—C$_5$H$_{11}$,  —C*H(C$_2$H$_5$)—C$_6$H$_{13}$,  —C*H(CF$_3$)—C$_6$H$_{13}$

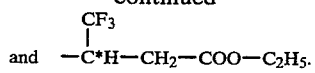

and  —C*H(CF$_3$)—CH$_2$—COO—C$_2$H$_5$.

7. A liquid crystal composition comprising at least one carboxylate compound represented by the following formula

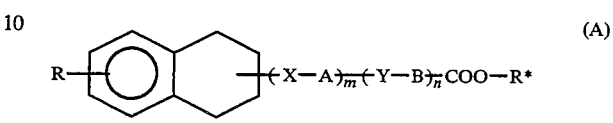
(A)

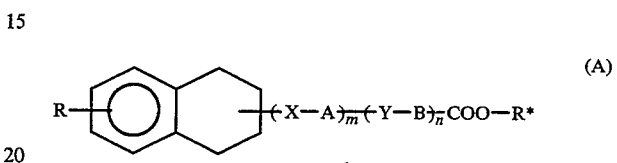
(A)

wherein R is a group selected from the group consisting of alkyl of 3 to 20 carbon atoms, alkoxy of 3 to 20 carbon atoms and halogenated alkyl of 3 to 20 carbon atoms, X and Y each represent —COO—, A and B each, independently, represent a member selected from the group consisting of

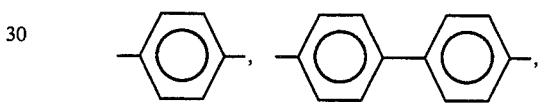

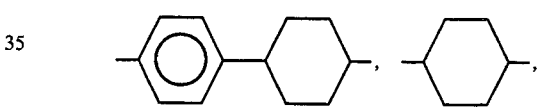

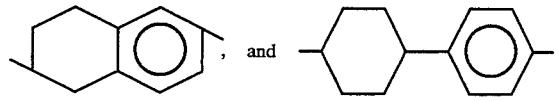

and R* is an optically active group of 4 to 20 carbon atoms containing at least one asymmetric carbon atoms, wherein hydrogen atoms attached to the carbon atoms of said optically active group may be substituted with halogen atoms, and m and n are each an integer of 0 to 2, with the proviso that m and n are not both 0, in an amount of 1 to 99 parts by weight based on 100 parts by weight of the composition, and at least one additional liquid crystal compound.

8. The liquid crystal composition according to claim 7 wherein R is an alkyl or alkoxyl group of 7 to 16 carbon atoms, X and Y each represent —COO—, A and B each, independently, represent a member selected from the group consisting of

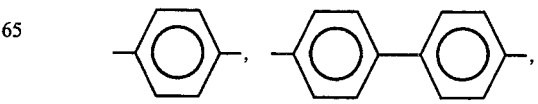

-continued

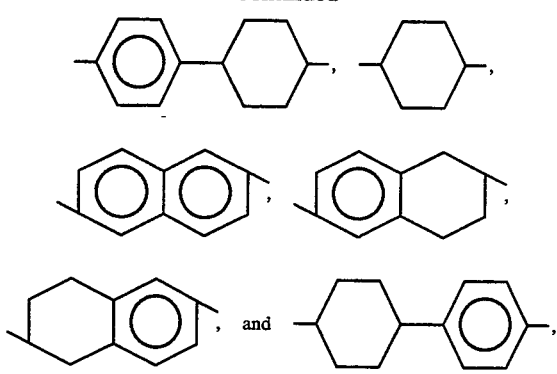

R* is an optically active alkyl or haloalkyl group of 5 to 9 carbon atoms which may be substituted with —COOC$_2$H$_5$, m is an integer of 0 to 2, and n is 0 or 1, with the proviso that both m and n are not both 0 at the same time.

9. A liquid crystal element comprising two substrates which face each other and have a gap therebetween, said gap being filled with a liquid crystal material comprising at least one carboxylate compound represented by the formula (A) as set forth in claim 4.

10. The liquid crystal element according to claim 9 wherein R is an alkyl or alkoxy group of 7 to 16 carbon atoms, A and B each, independently, represent a member selected from the group consisting of

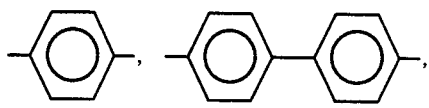

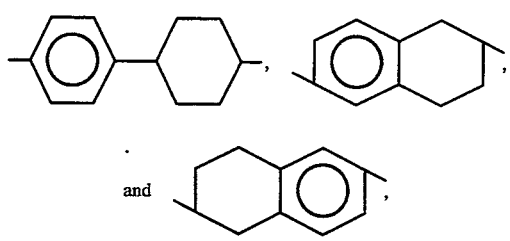

and R* is an optically active alkyl or haloalkyl group of 5 to 9 carbon atoms which may be substituted with —COO—C$_2$H$_5$.

11. The liquid crystal element according to claim 10 wherein R is an alkyl or alkoxy group of 7 to 12 carbon atoms, and R* is a member selected from the group consisting of

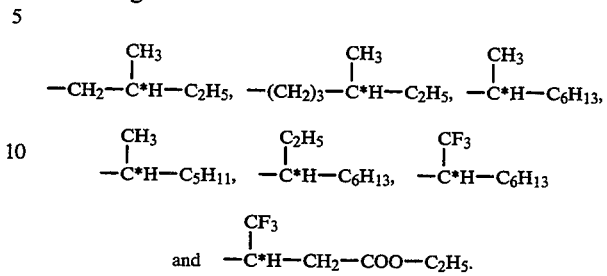

12. The liquid crystal element according to claim 9 wherein the liquid crystal material is a liquid crystal composition containing 1–99% by weight of the at least one carboxylate compound represented by the formula (A).

13. A process for the preparation of a liquid crystal element comprising a cell composed of two substrates which face each other and have a gap therebetween, and said gap being filled with a liquid crystal material, which comprises forming the cell by providing an orientation controlling film on the inner surface of at least one of said two substrates, filling the gap with the liquid crystal material comprising the liquid crystal compound of formula (A) according to claim 4, and heating said liquid crystal material contained in the cell to a temperature not lower than the temperature at which said material exhibits an isotropic liquid, followed by cooling to a temperature not higher than the temperature at which said material exhibits a liquid crystal.

14. The liquid crystal compound according to claim 4 which is selected form the group consisting of

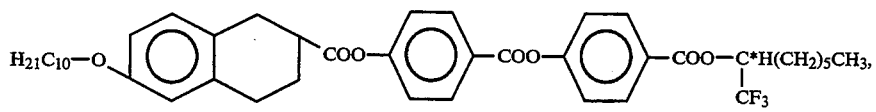

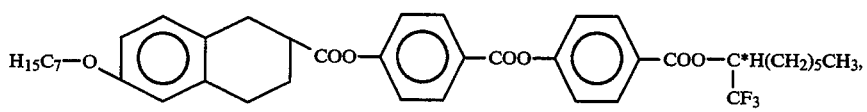

and

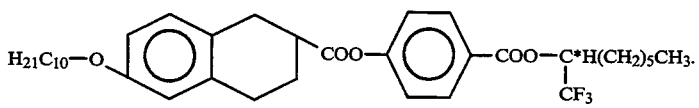

15. The liquid crystal composition as claimed in claim 8 comprising the at least one carboxylate compound represented by the above-mentioned formula [A] wherein R is an alkyl group of 7–12 carbon atoms or an alkoxy group of 7–12 carbon atoms and R* is a group selected from the group consisting of

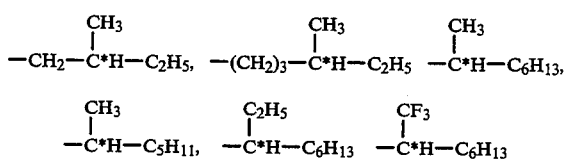

-continued and 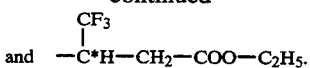

16. The liquid crystal element as claimed in claim 9 wherein an orientation controlling film is provided on the inner surface of at least one substrate.

17. The liquid crystal element as claimed in claim 16 wherein the orientation controlling film is an orientation controlling film that has been subjected to orientation treatment.

18. The process for the preparation of a liquid crystal element as claimed in claim 13 wherein the liquid crystal material is cooled at a cooling rate of not higher than 2° C./min from a temperature higher than the temperature at which said crystal material exhibits an isotropic liquid to a temperature lower than the temperature at which said material exhibits a liquid crystal.

19. The process for the preparation of a liquid crystal element as claimed in claim 13 wherein the orientation controlling film is an orientation controlling film subjected to orientation treatment.

20. A display unit comprising the liquid crystal element as set forth in any one of claims 9, 16, 17, 10, 11 or 12.

21. A liquid crystal display device comprising the liquid crystal element as set forth in any one of claims 9, 16, 17, 10 or 11.

22. An electrooptical display device comprising the liquid crystal element as claimed in any one of claims 9, 16, 17, 10 or 11.

23. A light modulation element comprising the liquid crystal element as claimed in any one of claims 9, 16, 17, 10 or 11.

24. The liquid crystal compound of claim 4 wherein in formula [A] the optically active group R* is

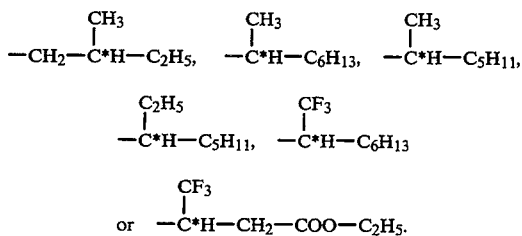

25. The liquid crystal compound of claim 4 wherein R* is

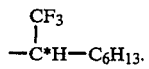

26. The liquid crystal compound of claim 6 wherein in the compound of formula (A) R is an alkoxy group of 7 to 12 carbon atoms, m and n are each 1, and R* is

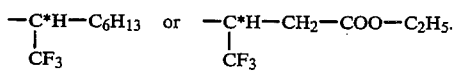

27. The liquid crystal compound of claim 26 wherein A and B are each

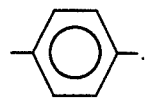

* * * * *